US007125689B2

(12) United States Patent
Carr et al.

(10) Patent No.: US 7,125,689 B2
(45) Date of Patent: Oct. 24, 2006

(54) METHOD FOR RENDERING STREPTOKINASE LESS IMMUNOGENIC TO A HUMAN

(75) Inventors: Francis Joseph Carr, Aberdeen (GB); Fiona Suzanne Adair, Aberdeen (GB); Anita Anne Hamilton, Aberdeen (GB); Graham Carter, Aberdeen (GB)

(73) Assignee: Biovation Limited, Aberdeen (GB)

( * ) Notice: Subject to any disclaimer, the term of this patent is extended or adjusted under 35 U.S.C. 154(b) by 455 days.

(21) Appl. No.: 10/300,215

(22) Filed: Nov. 20, 2002

(65) Prior Publication Data

US 2003/0153043 A1 Aug. 14, 2003

Related U.S. Application Data

(63) Continuation of application No. 09/438,136, filed on Nov. 10, 1999, which is a continuation of application No. PCT/GB98/01473, filed on May 21, 1998, now abandoned.

(60) Provisional application No. 60/067,235, filed on Dec. 2, 1997.

(30) Foreign Application Priority Data

| | | | |
|---|---|---|---|
| May 21, 1997 | (GB) | ................................ | 9710480.6 |
| Jul. 31, 1997 | (GB) | ................................ | 9716197.0 |
| Nov. 28, 1997 | (GB) | ................................ | 9725270.4 |
| Apr. 14, 1998 | (GB) | ................................ | 9807751.4 |

(51) Int. Cl.

| | |
|---|---|
| *C12P 21/06* | (2006.01) |
| *A61K 39/395* | (2006.01) |
| *A61K 38/43* | (2006.01) |
| *C12N 9/00* | (2006.01) |

(52) U.S. Cl. .................... 435/69.1; 435/183; 424/94.1; 424/133.1

(58) Field of Classification Search ............... 435/69.1, 435/69.6, 183; 530/387.1, 387.3, 388.1; 424/94.1, 133.1

See application file for complete search history.

(56) References Cited

U.S. PATENT DOCUMENTS 5,712,120 A * 1/1998 Rodriguez et al.

FOREIGN PATENT DOCUMENTS

| | | | |
|---|---|---|---|
| EP | 0699755 A2 * | 6/1996 | |
| WO | WO 9007861 A1 * | 7/1990 | |
| WO | WO 9109125 A1 * | 6/1991 | |
| WO | WO 9317105 A1 * | 9/1993 | |

OTHER PUBLICATIONS

Altuvia et al. Journal of Molecular Biology, 249:244-250, 1995.*

Rammensee et al. Immunogenetics, 41:178-228, 1995.*

Bruserud et al. Journal of Clinical and Laboratory Immunology 20(2):69-74, 1986.*

Eyerman et al. Journal of immunology 152:1569-1577, 1994.*

* cited by examiner

*Primary Examiner*—Sheela J. Huff
*Assistant Examiner*—David J. Blanhard
(74) *Attorney, Agent, or Firm*—Olson & Hierl, Ltd.

(57) ABSTRACT

Protein, or parts of proteins, may be rendered non-immunogenic, or less immunogenic, to a given species by identifying in their amino acid sequences one or more potential epitopes for T-cells of the given species and modifying the amino acid sequence to eliminate at least one of the T-cell epitopes. This eliminates or reduces the immunogenicity of the protein when exposed to the immune system of the given species. Monoclonal antibodies and other immunoglobulin-like molecules can particularly benefit from being de-immunised in this way: for example, mouse-derived immunoglobulins can be de-immunised for human therapeutic use.

1 Claim, 40 Drawing Sheets

DNA sequences of 340 $V_H$ and $V_L$

340 $V_H$
GAAGTGCAGCTGGTGGAGTCTGGGGGAGGCTTAGTGAAGGCTGGAGGGTCCCTGAAA
CTCTCCTGTGCAGCCCTCTGGATTCGCTTTCGATACCTATGACATGTCTTGGGTTCGC
CAGACTCCGGAGAGAGGCTGGAGTGGGTCGCATACATTGGTAGTGGTGGTGATAGA
ACCTACTATCCAGACACTGTGAAGGGCCGATTCACCATTTCCAGAGACAATGGCAAG
AACACCCTGTATTGCAATTGAACAGTCTGAAGTCTGAGGACACAGCCATGTATTAC
TGTGCAAGACATTAGGTCACTACGTGGACTACTGTGGACTACTGGGGTCAAGGA
ACCTCAGTCACCGTCCCTCA

340 $V_L$
ACATTGTGCTGACACAGTCTCCTGCTTCCCTTAGCTGTGTATCTCTGGGGCAGAGGGCCA
CCATCTCATACAGGGCCAGCAAAAGTGTCAGTACATCTGGCTATAGTTATATGCACT
GGAACCAACAGAAACCAGGACAGCCACCCAGACTCCATCTATCTTGTATCCAACC
TAGAATCTGGGGTCCCTGCCAGGTTCAGTGGCAGTGGATCTGGGACAGAGTTCACCC
TCAACACATCCATCCTGTGCAGGCTGCAACCTATTACTGTCAGCACATTA
GGGAGCTTATCACGTTCGGAGGGGGGACCAAGCTGGAAATAAAA

FIG. 1

Protein sequence of 340 murine VH and VL.

```
Murine 340 VH   EVQLVESGGGLVKAGGSLKLSCAASGFAFDTYDMSWVRQTPEKRLEWVAYI
Murine 340 VL   DIVLTQSPASLAVSLGQRATISYRASKSVSTSGYSYMHWNQQKPGQPPRLL Murine 340 VH   GSGGDRTYYPDTVKGRFTISRDNGKNTLYLQLNSLKSEDTAMYYCARHYGH
Murine 340 VL   IYLVSNLESGVPARFSGSGSGTEFTLNIHPVEEEDAATYYCQHIRELITFG Murine 340 VH   YVDYAVDYWGQGTSVTVSS
Murine 340 VL   GGTKLEIK
```

FIG. 2

Protein sequence of humanised 340 VH and VL

Humanised 340 VH   EVQLVESGGGLVQPGGSLRLSCAASGFAFDTYDMSWVRQAPGKGLEWVAYI
Humanised 340 VL   EIVLTQSPATLSLSPGERATLSYRASKSVSTSGYSYMHWNQQKPGQAPRLL Humanised 340 VH   GSGGDRTYYPDTVKGRFTISRDNAKNSLYLQMNSLRAEDTAVYYCARHYGH
Humanised 340 VL   IYLVSNLESGIPARFSGSGSGTDFTLTISSLEPEDFAVYYCQHIRELITFG Humanised 340 VH   YVDYAVDYWGQGTTVTVSS
Humanised 340 VL   GGTKVEIK

FIG. 3

Oligonucleotides for construction of humanised 340 VH and VK

Long Oligonucleotides:
VH1
5' GACATGTCATAGGTATCGAAAGGCGAATCCAGAGAGGCTGCACAGGAGAGAGTCTCAGGG
ACCCTCCAGGCTGCACTAAGCCTCCCCCAGACTCCACCAGCTGCACTTC 3'
VH2
5' CGATACCTATGACACATGTCTCTTGGGTTCGCCCAGGCTCCGGGGAAGGGGCTGGAGTGG
GTCGCATACATTGGTAGTGGTGGTGATAGAACCTACTATCCAGACACTG 3'
VH3
5' GGCTGTGTCCTCAGCCCTCAGACTGTTCATTTGCAAATACAGGGAGTTCTTGGCA
TTGTCTCTGGAAATGGTGAATCGGCCCTTCACAGTGTCTGGATAGTAGG 3'
VH4
5' AGGGCTGAGGACACAGCCGTGTATTACTGTGCAAGACATTATGTCACTACGTGG
ACTATGCTGTGGACTACTGGGGTCAAGGAACCACAGTCACCGTCTCCTCA 3'
VK1
5' AGATGTACTGACACTTTTGCTGGCCCTGTATGAGAGGGTGGCCCTCTCCCCCGGA
GATAGAGATAAGGTAGCAGGAGACTGTGTCAGCACACAATCTC 3'

FIG. 4A

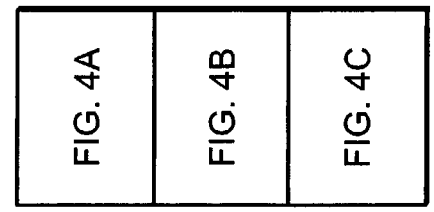

FIG. 4

VK2
5' GCAAAAGTGTCAGTACATCTGGCTATAGTTATATGCACTGGAACCAACAGAAACC
AGGACAGGCACCCAGACTCCTCATCTCTATCTTGTATCCAACCTA 3'
VK3
5' CGGCTCCAGAGAAGATGGTGAGGGTGAAGTCTGTCCCAGACCCCACTGCCACTG
AACCTGGCAGGGATCCCAGATTCTAGGTTGGATACAAGATA 3'
VK4
5' ATCTCTCTCTGGAGCCGGAGGATTTTGCAGTCTATTACTGTCAGCACACATTAGGG
AGCTTATCACGTTCGGAGGGGGACCAAGGTGGAAATAAAA 3'

Short Flanking Primers:
VH5
5' GAAGTGCAGCTGGTGGAGTC 3'
VH6
5' TGAGGAGACGGTGACTGTGG 3'
VK5
5' GAGATTGTGCTGACACAGTC 3'
VK6
5' TTTTATTTCCACCTTGGTCC 3'

FIG. 4B

For 5' flanking sequence from VHPCR1 and VKPCR1:
VH/VK1
5' AAGCTTATGAATATGCAAAT 3'
VH7
5' CACCAGCTGCACTTCGGAGTGGACACCTGTG 3'
VK7
5' TGTCAGCACAATCTCGGAGTGGACACCTGTG 3'

For 3' flanking sequence from VHPCR1 and VKPCR1:
VH8
5' GTCACCGTCTCCTCAGGTGAGTCCTTACAA 3'
VH9
5' GCGGATCCCTATAAATCTCTG 3'
VK8
5' AAGGTGGAAATAAAACGTGAG 3'
VK9
5' GCGGATCCAACTGAGGAAGC 3'

FIG. 4C

Protein sequence of de-immunised 340 VH and VL

340 VH  EVQLVESGGGLVQPGGSLRLSCAASGFTFDTYDMSWVRQAPGKGLEWVAYI
340 VK  EIVLTQSPATLAVSPGEKATISYRASKSVSTSGYSYMHWNQQKPGQPPRLL

340 VH  GSGGDRTYYPDTVKGRFTISRDNAKNTLYLQMNSLRAEDTAVYYCARHYGH
340 VK  IYLVSNLESGVPARFSGSGSGTDFTLTISSVEPEDAATYYCQHIRELITFG

340 VH  YVDYAVDYWGQGTTVTVSS
340 VK  GGTKLEIK

FIG. 5

Oligonucleotides for construction of de-immunised 340 VH and VK

Long Oligonucleotides:
VH1
5′ GACATGTCATAGGTATCGAAAGTGAATCCAGAGGCTGCACAGGAGAGTCTCAGGG
ACCCTCCAGGCTGCACTAAGCCCTCCCCAGACTCCACCAGCTGCACTTC 3′
VH2
5′ CGATACCTATGACATGTCTTGGGTTCGCCAGGCTCCGGGGAAGGGGCTGGAGTGG
GTCGCATACATTGGTAGTGGTGATAGAACCTACTATCCAGACACTG 3′

FIG. 6A

| FIG. 6A |
|---|
| FIG. 6B |

FIG. 6

VH3
5' GGCTGTGTCCTCAGCCCTCAGACTGTTCATTTGCAAATACAGGGTGTTCTTGGCATTGTCTCTGGAAATGGTGAATCGGCCCCTTCACAGTGTCTGGATAGTAGG 3'

VH4
5' AGGGCTGAGGACACAGCCGTGTATTACTGTGCAAGACATTATGGTCACTACGTGGACTATGCTGTGGACTACTGGGGTCAAGGAACCACAGTCACCGTCTCCTCA 3'

VK1
5' AGATGTACTGACACTTTGCTGGCCCTGTATGAGATGGTGGCCTTCTCCCCGGAGATACAGCTAAGGTAGCAGGAGACTGTGTCAGCACAATCTC 3'

VK2
5' GCAAAAGTGTCAGTACATCTGGCTATAGTTATATGCACTGGAACCAACAGAAACCAGGACAGCAGCACCCAGACTCCTCATCTATCCTGTATCCAACCTA 3'

VK3
5' CGGCTCCACAGAACTGATGGTGAGGGTGAAGTCTGTCCCAGACCCACTGCCACTGAACCTGGCAGGGGACCCCAGATTCTAGGTTGGATACAAGATA 3'

VK4
5' ATCAGTTCTGTGGAGCCGGAGGATGCTGCAACCTATTACTGTCAGCACATTAGGGAGCTTATCACGTTCGGAGGGGGACCAAGCTGGAAATAAAA 3'

Other primers are as for the humanised genes apart from:

VK6
5' TTTTATTTCCAGCTTGGTCC 3'

VK8
5' AAGCTGGAAATAAAACGTGAG 3'

FIG. 6B

Protein sequence of humanised 340 VH compared with the sequence with murine epitopes inserted HUMANISED 340 VH    EVQLVESGGGLVQPGGSLRLSCAASGFAFDTYDMSWVRQAPGKGL
ALTERED 340 VH      EVQLVESGGGLVQPGGSLRLSCAASGFAFDTYDMSWVRQAPGKGL HUMANISED 340 VH    EWVAYIGSGGDRTYYPDTVKGRFTISRDNAKNSLYLQMNSLRAED
ALTERED 340 VH      EWVAYIGSGGDRTYYPDTVKGRFTISRDNAKNSLSLQMNSLRAED HUMANISED 340 VH    TAVYYCARHYGHYVDYAVDYWGQGTTVTVSS
ALTERED 340 VH      TAVYYCARHYGHYVDYAVDYWGQGSTVTVSS

FIG. 8

Oligonucleotide primers for insertion of murine epitopes into humanised 340 VH by SOE PCR Mutagenic Oligonucleotides:

5' TCCCTGTCTTTGCAAATGAA3′

5′CATTTGCAAAGACAGGGAGTTCT3′

5′TCAAGGATCCACAGTCACCG3′

5′ACTGTGGATCCTTGACCCCA3′

Flanking Oligonucleotides:

5′AAGCTTATGAATATGCAAAT3′

5′GCGGATCCTATAAATCTCTG3′

FIG. 9

Protein sequence of mouse deimmunised 340 VH

EVQLVESGGGLVKAGGSLKLSCAASGFAFDTYDMSWVRQTPEKRLEWVAYIGSGGDR
TYYPDTVKGRFTISRDNGKNSLYLQMNSLKSEDTAMYYCARHYGHYVDYAVDYWGQG
TSVTVSS

FIG. 10

Oligonucleotide primers for construction of mouse deimmunised VH

VH1
5'GACATGTCATAGGTATCGAAAGGCGAATCCAGAGAGCTGCACAGGAGAGAGTTTCAGGGACCCTCCAGCCCTTCACTAAGCCTCCCCCAGACTCCCACCAGCTGCACTTC3'

VH2
5'CGATACCTATGACATGTCTTGGGTTCGCCAGACTCCGGAGAAGAGGCTGGAGTGGGTCGCATACATTGGTAGTGGTGATAGAACCTACTATCCAGACACACTG3'

VH3
5'GGCTGTGTCCTCAGACTTCAGACTTTCAGACTGTTCATTTGCAAATACAGGGAGTTCTTGCCATTGTCTCTGGAAATGGTAATCGGCCCCTTCACAGTGTCTGGATAGTAGG3'

VH4
5'AAGTCTGAGGACACAGCCATGTATTACTGTGCAAGAGACATTATGTCACTACGTGGACTATGCTGTGGACTACTGGGGTCAAGGAACCTCAGTCACCGTCTCCTCA3'

VH5
5'GAAGTGCAGCTGGTGGAGTC3'
VH6
5'TGAGGAGACGGGTGACTGAGG3'

Other primers are as for Humanised VH

FIG. 11

DNA sequences of murine 708 V_H and V_L

708 V_H
GAGGTCCAGCTGCAACAGTCTGGACCTGAGCTGGTGAAGCCTGGGGCTTCAGTGAAG
ATATCCTGTAAGACTTCTGGACACACATTCACTGAATACAACATGCAGTGGGTGAAG
CAGAGCCTTGGACAGAGCCTTGAGTGGATTGGAGGTATTAATCCTAACAATGTTGGT
TCTATCTACAACCAGAAGTTCAGGGGCAAGGCCACATTGACTGTAGACAAGTCCTCC
AGCACAGCCTACATGGAGCTCCGCAGCCTGACATCTGAGGATTCTGCAGTCTATTAC
TGTGCAAGAGGCTATGTAACTACGTGGCTTACTGGGGCCAAGGGACTCTGGTCACT
GTCTCTGCA

708 V_L
GACATTGTGATGACCCAGTCTCAAAAATTCATGTCCACATCAGTAGGAGACAGGGTC
AGCGTCACCTGCAAGGCCAGTCAGAATGTGAATACTAATGTAGCCTGGTATCAACAG
AAACCAGGGCAATCTCCTAAATCACTGATTTACTCGGCATCCTACGATACAGTGGA
GTCCCTGATCGCTTCACAGGGCAGTGGATCTGGGACAGATTTCACTCTCACCATCAGC
AATGTGCAGTCTGAAGACTTGGCAGAGTTTTTCTGTCAGCAATATAACAGGTATCCG
TTCACGTTCGGTGGTGGGACCAAGCTGGAGCTGAAA

FIG. 13

Protein sequence of murine 708 $V_H$ and $V_L$

Murine 708 VH
EVQLQQSGPELVKPGASVKISCKTSGHTFTEYNMQWVKQSLGQSLEWIGGINPNNVG
SIYNQKFRGKATLTVDKSSSTAYMELRSLTSEDSAVYYCARGYGNYVAYWGQGTLVT
VSA Murine 708 VL
DIVMTQSQKFMSTSVGDRVSVTCKASQNVNTNVAWYQQKPGQSPKSLIYSASYRYSG
VPDRFTGSGSGTDFTLTISNVQSEDLAEFFCQQYNRYPFTFGGGTKLELK

FIG. 14

Protein sequence of de-immunised 708 V$_H$ and V$_L$

De-immunised 708 V$_H$
EVQLVQSGPGLVQPGGSVRISCATSGHTFSEYNMQWVKQAQGKGLEWMGGINPNNVG
SIYNQKFRGRFTLSVEKSKNTAYMQLSSLKSEDSAVYYCARGYGNYVAYWGQGTLVT
VSS De-immunised 708 V$_L$
DIQMTQSPSSMSTSVGDRVTVTCKASQNVNTNVAWYQQKPGKSPQSLIYSASYRYSG
VPSRFSGSGSGTDFTLTISSVQPEDFAEYYCQQYNRYPFTFGGGTKLELK

FIG. 15

Oligonucleotides for construction of De-immunised 708 $V_H$ and $V_L$

Long Oligonucleotides:
DIVH1
5' TGTCCAGAAGTCGCACAGGATATCCTCACTGAACCCCCAGGCTGCACCAGCCCAGGTCCAGACTGTACCAGCTGGACCTC 3'
DIVH2
5' CTGTGCGACTTCTGGACACACATTCTCTGAATACAACATGCAGTGGGTGAAGCAGGCCCAAGGAAAGGGCCTTGAGTGG 3'
DIVH3
5' AACCTGCCCCTGAACTTCTGGTTGTAGATAGAACCAACATTGTTAGGATTAATACCTCCCATCCACTCAAGGCCCTTTCC 3'
DIVH4
5' GAAGTTCAGGGGCAGGTTCACATTGTCTGTAGAGAAGTCCAAGAACACAGCCTACATGCAGCTCAGCAGCCTGAAATCTG 3'
DIVH5
5' TTGGCCCCAGTAAGCCACGTAGTTACCATAGCCCTCTTGCACAGTAATAGACTGCAGAATCCCTCAGATTTCAGGCTGCTGA 3'
DIVH6
5' GTGGCTTACTGGGGCCAAGGGACTCTGGTCACTGTCTCTTCA 3'

FIG. 16A

DIVK1
5' TGACTGGCCTTGCAGGTGACGGTGACCCTGTCTCCTACTGATGTGGACATGGAGCTTGGAGACTGGGTCATCTGAATGTC3'
DIVK2
5' CACCTGCAAGGCCAGTCAGATCAGAATGTGAATACTAATGTAGCCTGGTATCAACAGAAACCAGGGAAATCTCCTCAATCACTGA3'
DIVK3
5' CCCAGATCCACTGCCTGAGAAGCGACTAGGGACTCCACTGTATCGGTAGGATGCCGAGTAAATCAGTGATTGAGGAGATT3'
DIVK4
5' TCAGGCAGTGGATCTGGGACAGATTTCACTCTCACCATCAGCTCTGTGCAGCCTGAAGACTTCGCAGAGTATTACTGTCA3'
DIVK5
5' TTTCAGCTCCAGCTTGGTCCCACCACCGAACGTGAACGGATACCTGTTATATTGCTGACAGTAATACTCTGCG3'

Short Flanking Primers:-
DIVH7
5' GAGGTCCAGCTGGTACAG3'
DIVH8
5' TGAAGAGACAGTGACCAG3'
DIVK6
5' GACATTCAGATGACCCAG3'
DIVK7
5' TTTCAGCTCCAGCTTGGT3'

FIG. 16B

For 5' flanking sequence from VHPCR1 and VKPCR1:

VH/VK1
5' GCAAGCTTATGAATATGCAAAT 3'

DIVH9
5' TACCAGCTGGACCTCGGAGTGGACACCTGT 3'

DIVK8
5' GGTCATCTGAATGTCGGAGTGGACACCTGT 3'

For 3' flanking sequence from VHPCR1 and VKPCR1:

DIVH10
5' GTCACTGTCTCTTCAGGTGAGTCCTTACAA 3'

DIVH11
5' GCGGATCCTATAAATCTCTG 3'

DIVK9
5' AAGCTGGAGCTGAAACGTGAGTAGAATTTA 3'

DIVK10
5' GCGGATCCAACTGAGGAAGC 3'

FIG. 16C

Protein sequence of Vaccine 1 708 $V_H$ and $V_L$.

708 V1 $V_H$
EVQLQQSGPELVKPGASVKISCKTSGYTFTEYNMNWVRQSPGQSLEWIGGINPNNVG
SIYNQKFRGKATLTVDKSSSTAYMELRSLTSEDSAVYYCARGYGNYVAYWGQGTLVT
VSA

708 V1 $V_L$

DIVMTQSQKFVSTSVGDRVSITCKASQNVNTNVAWYQQKPGQSPQSLIYSASYRFSG
VPDRFSGSGSGTDFTLTISNVQSEDFAEYYCQQYNSYPRTFGGGTKLELK

FIG. 17

Oligonucleotides for construction of Vaccine 1 708 $V_H$ and $V_L$

Long Oligonucleotides:
VHDT340R
5' TATCCAGAAGTCTTACAGGATATCTTCACTGAAGCCCCAGGCTTCACCAGCTCAG
GTCCAGACTGTTGCAGCTGGACCTC3'
VHDT322F
5' CCTGTAAGACTTCTGGATACACATTCACTGAATACAACATGAACTGGGTGAGGCA
GAGCCCCGGACAGAGCCTTGAGTGG3'
VHDT446F
5' GAAGTTCAGGGGGCAAGGCCACATTGACTGTAGACAAGTCCTCCAGCACAGCCTAC
ATGGAGCTCCGCAGCCTGACATCTG3'
VHDT463R

FIG. 18A

| FIG. 18A |
| FIG. 18B |
| FIG. 18C |

FIG. 18

5'GCCTTGCCCCTGAACTTCTGGTTGTAGATAGAACCAACATTGTTAGGATTAATAC
CTCCAATCCACTCAAGGCTCTGTCC3'
VHDT570F

5'GTGGCTTACTGGGGCCAAGGGACTCTGGTCACTGTCTCTGCA
VHDT587R

5'TTGGCCCCAGTAAGCCACGTAGTTACCATAGCCCTCTTGCACAGTAATAGACTGCA
GAATCCCTCAGATGTCAGGCTGCGGGA
VKDT322F

5'TAACCTGCAAGGCCAGTCAGAATGTGAATACTAATGTAGCCTGGTATCAACAGAA
ACCAGGGCAATCTCCCTCAATCACTG3'
VKDT340R

5'TGACTGGCCTTGCAGGTTATGCTGACCCTGTCTCCCTACTGATGTGGACACGAATT
TTTGAGACTGGGTCATCACAATGTC3'
VKDT446F

5'CTCAGGCAGTGGGATCTGGGACAGATTTCACTCTCACCATCAGCAATGTGCAGTCT
GAAGACTTTGCAGAGTATTACTGTC3'
VKDT463R

5'CCAGATCCACTGCCTGAGAAGGCGATCAGGAGACTCCACTGAATCGGTAGGATGCCG
AGTAAATCAGTGATTGAGGAGATTG3'
VKDT570F

5'CTGGAGCTGAAACGTGAGTAGAATTTAAACTTGCTTCCCTCAGTTGGATCCGC3'
VKDT587R

5'CTCACGTTCAGCTCCAGCTTGGTCCCACCACCGAACGTGCGCGGATAGCTGTTA
TATTGCTGACAGTAATACTCTGCAA3'

FIG. 18B

Short Flanking Primers:-
VH261F
5' GAGGTCCAGCTGCAACAGTC 3'
VH611R
5' TGCAGAGACAGTGACCAGA 3'
VK261F
5' GACATTGTGATGACCCAGT 3'
VK12
5' GCGGGATCCAACTGAGGAAGCA 3'

For 5' flanking sequence from VHPCR1 and VKPCR1:
VH/VK1
5' GCAAGCTTATGAATATGCAAAT 3'
VH276R
5' GTTGCAGCTGGACCTCGGAGTGGACACCTGTG 3'
VK275R
5' GGTCATCACAATGTCGGAGTGGACACCTGT 3'

For 3' flanking sequence from VHPCR1:
VH597F
5' GTCACTGTCTCTGCAGGTGAGTCCTTACAAC 3'
VH12
5' GCGGGATCCTATAAATCTCTG 3'

FIG. 18C

Protein sequence of Vaccine 2 708 $V_H$ and $V_L$.

708 V2 $V_H$
EVQLQQSGPELVKPGASVKISCKTSGYTFTEYNMNWVRQSPGQSLEWNGGRNNSIVK
SITVSASGTKATLTVDKSSSTAYMELRSATSEDSAGIYISPSYTYYRPGVGQGTLGT
VSA

708 V2 $V_L$
DIVMTQSQKFVSTSVGDSASVTCTLLSVTRNDVSRYQQSPGQWPQSLIYSASYRFSG
VPDRFSGSGSGTDFTLTISNVQSEDLAEFMCYLSGANLNLTGGGTKLEVR

FIG. 19

Oligonucleotides for construction of Vaccine 2 708 $V_H$ and $V_L$

Long Oligonucleotides:
VHDT340R
5' TATCCAGAAGTCTTACAGGATATCTTCACTGAAGCCCCAGGCTTCACCAGCTCAG
GTCCAGACTGTTGCAGCTGGACCTC3′

VHDT322F

5′CCTGTAAGACTTCTGGATACACATTCACTGAATACAACATGAACTGGGTGAGGCA
GAGCCCCGGACAGAGCCTTGAGTGG3′

VHCEA447F

5′GCCTCCGGCACCAAGGCCACATTGACTGTAGACAAGTCCTCCAGCACAGCCTACA
TGGAGCTCCGCAGCGCCACATCTGA3′

FIG. 20A

VHCEA463R
5' GCCTTGGTGCCGGAGGCGGACACGGTGATAGACTTAACGATGGAGTTATTGCGAC
CTCCGTTCCACTCAAGGCTCTGTCC3'
VHCEA570F
5' CGCCCCGGCGTGGGCCAAGGGACTCTGGGCACTGTCTCTGCA3'
VHCEA586R
5' TGGCCCACGCCGGGGCGGGTAGTAGGTATAGGAGGGGAGATGTAGATGCCTGCAG
AATCCTCAGATGTGGGCGCTGCG3'
VKCEA324F
5' ACCTGCACCCTGCTGTCCGTGACCCGCAACGACGTATCCCGCTATCAACAGTCCC
CAGGGCAATGGCCTCAATCACTGAT3'
VKCEA340R
5' GACAGCAGGTGCAGGTCACGCTGGCGGAGTCTCCTACTGATGTGGACACGAATT
TTTGAGACTGGGTCATCACAATGTC3'
VKCEA450F
5' GGCAGTGGATCTGGGACAGATTTCACTCTCACCATCAGCAATGTGCAGTCTGAAG
ACCTGGCAGAGTTCATGTGTTACCT3'
VKCEA486R
5' GTCCCAGATCCACTGCTGAGAAGCGATCAGGGACTCCACTGAATCGGGTAGGATG
CCGAGTAAATCAGTGATTGAGGCCA3'
VKCEA576F
5' GTGCGACGTGAGTAGAATTTAAACTTTGCTTCCTCAGTTGGATCCGC3'
VKCEA592R
5' TTCTACTCACGTCGCACCTCCAGCTTGGTCCCACCACCGGTTCAGGTTCAGGTTGG
CGCCGGACAGGTAACACATGAACTC3'

FIG. 20B

Short Flanking Primers:
VH261F
5' GAGGTCCAGCTGCAACAGTC 3'
VH611R2
5' TGCAGAGACAGTGCCCAG 3'
VK261F
5' GACATTGTGATGACCCAGT 3'
VK12
5' GCGGATCCAACTGAGGAAGCA 3'

For 5' flanking sequence from VHPCR1:
VH/VK1
5' GCAAGCTTATGAATATGCAAAT 3'
VH276R
5' GTTGCAGCTGGACCTCGGAGTGGACACCTGTG 3'
VK275R
5' GGTCATCACAATGTCGGAGTGGACACCTGT 3'

For 3' flanking sequence from VHPCR1 and VKPCR1:
VH597F
5' GTCACTGTCTCTGCAGGTGAGTCCTTACAAC 3'
VH12
5' GCGGATCCTATAAATCTCTG 3'

FIG. 20C

Protein sequence of Vaccine 3 708 $V_H$

708 V3 $V_H$
EVQLQQSGPELAKFGATISFSCNTGYKLFGSTSMNRLRQSPGQSLEWNGGRNNSIVK
SITVSASGTKATLTVDKSSSTAYMELRSATSEDSAGIYISPSYTYYRPGVGQGTLGT
VSA

FIG. 21

Oligonucleotides for construction of Vaccine 3 708 $V_H$

Long Oligonucleotides:
VHCD340R
5′ TTGTAGCCGGTGTTGCAGGAGAAGGAGATGGTGGCGCCGAACTTCGCCAGCTCGG
GGCCGGACTGCTGCAGCTGCACCTC3′
VHCD322F
5′ CTGCAACACGGCTACAAGCTGTTTCGGCTCCACCTCCATGAACCGACTTCGCCAG
TCCCCGCCAGTCCCTGGAGTGGA3′
VHCD463R
5′ GCCTTGGTGCCGGAGGCGGACACGGTGATAGACTTAACGATGGAGTTATTGCGAC
CTCCGTTCCACTCCAGGGACTGGCC3′

FIG. 22A

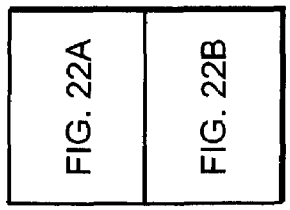

FIG. 22

VHCEA447F
5' GCCTCCGGGCACCAAGGCCCACATTGACTGTAGACAAGTCCTCCAGCACACAGCCTACA
TGGAGCTCCGCAGCCGCCACATCTGA3'

VHCEA570F
5' CGCCCCGGCGTGGGCCAAGGACTCTGGGCACTGTCTCTGCA3'

VHCEA586R
5' TGGCCCACGCCCGGGGCGGGTAGTAGGTATAGGAGGGGAGATGTAGATGCCTGCAG
AATCCTCAGATGTGGCGCTGCG3'

Short Flanking Primers:-

VH261F
5' GAGGTCCAGCTGCAACAGTC3'

VH611R2
5' TGCAGAGACAGTGCCCAG3'

For 5' flanking sequence from VHPCR1:

VH/VK1
5' GCAAGCTTATGAATATGCAAAT3'

VH276R
5' GTTGCAGCTGGACCTCGGAGTGGACACCTGTG3'

For 3' flanking sequence from VHPCR1:

VH597F
5' GTCACTGTCTCTGCAGGTGAGTCCTTACAAC3'

VH12
5' GCGGATCCTATAAATCTCTG3'

FIG. 22B

Oligonucleotides for construction of Chimaeric 708 $V_H$ and $V_L$

Long Oligonucleotides:

VHCH355R
5'TATTCAGTGAATGTGTCCAGAAGTCTTACAGGATATCTTCACTGAAGCCCCAGGCTTC ACCAGCTCAGGTCCAGACTGTTGCAGCTGACCCTC3'

VHCH337F
5'GACACACATTCACTGAATACAACATGCAGTGGGTGAAGCAGAGCCTTGGACAGAGCCTTG AGTGGATTGGAGGTATTAATCCTAACAATGTTGGTTCTATCTAC3'

VHCH525R
5'CAGATGTCAGGTGCGGAGCTCCATGTAGGCTGTGTGCTGGAGGACTTGTCTACAGTCAATG TGGCCCTGCCCCTGAACTTCTGTTGTAGATAGAACCAACATT3'

VHCH507F
5'CTCCGCAGCCTGACATCTGAGGATTCTGCAGTCTATTACTGTGCAAGAGGCTATGGTAAC TACGTGGCTTACTGGGGCCAAGGGACCCTCTGGTCACTGTCTCTGCA3'

VKCH345F
5'GTGAATACTAATGTAGCCTGGTATCAACAGAAACCAGGCAATCTCCTAAATCACTGATT TACTCGGCATCCTACCGATACAGTGGAGTCCCTGATCGCTTCAC3'

VKCH364R
5'CAGGCTACATTAGTATTCACATTCTGACTGGCCCTTGCCAGGTGACGCTGACCCTGTCTCCT ACTGATGTGGACATGAATTTTTGAGACTGGGTCATCACAATGTC3'

VKCH518F
5'TTTCTGTCAGCAATATAACAGGTATCCGTTCAGGTCTTCAGACTCTTCAGACTCTGCCAAGTCTTCAGACTGCCAAGTCTGGAGCT GAAACGTGAGTAGAATTTAAACTTTGCTTCCTCAGTTGGATCCGC3'

VKCH533R
5'ATATTGCTGACAGAAAAACTCTGCCAAGTCTCCACTGCCTGTGAAGGCGATCAGGGACTC GAAATCTGTCCCAGATCCCAGATCCACACATTGCTGATGGTGAGAGT

Short Flanking Primers:
VH261F
5' GAGGTCCAGCTGCAACAGTC 3'
VH611R
5' TGCAGAGACAGTGACCAGA 3'
VK261F
5' GACATTGTGATGACCCAGT 3'
VK12
5' GCGGGATCCAACTGAGGAAGCA 3'

For 5' flanking sequence from VHPCR1 and VKPCR1:
VH/VK1
5' GCAAGCTTATGAATATGCAAAT 3'
VH276R
5' GTTGCAGCTGGACCTCGGAGTGGACACCTGTG 3'
VK275R
5' GGTCATCACAATGTCGGAGTGGACACCTGT 3'

For 3' flanking sequence from VHPCR1:
VH597F
5' GTCACTGTCTCTGCAGGTGAGTCCTTACAAC 3'
VH12
5' GCGGGATCCTATAAATCTCTG 3'

FIG. 23B

Protein sequence of humanised A33 V$_H$ and V$_L$

Humanised A33 V$_H$
EVQLLESGGGLVQPGGSLRLRLSCAASGFAFSTYDMSWVRQAPGKGLEWVATIS
SGGSYTYYLDSVKGRFTISRDSSKNTLYLQMNSLQAEDSAIYYCAPTTVVPFA
YWGQGTLVTVSS Humanised A33 V$_L$
DIQMTQSPSSLSVSVGDRVTITCKASQNVRTVVAWYQQKPGLAPKTLIYLASN
RHTGVPSRFSGSGSGTDFTFTISSLQPEDIATYFCQQHWSYPLTFGQGTKVEVK

FIG. 24

Protein sequence of de-immunised humanised A33 $V_H$ and $V_L$

De-Immunised Humanised A33 $V_H$
EVQLLESGGGLVQPGGSLRLSCAASGFTFSTYDMSWVRQAPGKGLEWVATIS
SGGSYTYYLDSVKGRFTISRDSSKNTLYLQMNSLQAEDTALYFCAPTTVVPFA
YWGQGTLVTVSS De-Immunised Humanised A33 $V_L$
DIQMTQSPSSLSVSVGDRVTITCKASQNVRTVVAWYQQKPGLAPKSLIYLASN
RHTGVPSRFSGSGSGTDFTFTISSLQPEDFATYYCQQHWSYPLTFGGGTKVEV
K

FIG. 25

Protein sequence of murine A33 $V_H$ and $V_L$

Murine A33 $V_H$
EVKLVESGGGLVKPGGSLKLSCAASGFAFSTYDMSWVRQTPEKRLEWVATIS
SGGSYTYYLDSVKGRFTISRDSARNTLYLQMSSLRSEDTALYYCAPTTVVPFA
YWGQGTLVTVSA Murine A33 $V_L$
DIVMTQSQKFMSTSVGDRVSITCKASQNVRTVVAWYQQKPGQSPKTLIYLAS
NRHTGVPDRFTGSGSGTDFLTISNVQSEDLADYFCLQHWSYPLTFGSGTKLE
VK

FIG. 26

Protein sequence of de-immunised murine A33 $V_H$ and $V_L$

De-immunised murine A33 $V_H$
EVQLVESGGGEVKKPGATLKLSCKASGFTFTTYDMSWVRQAPGKGLEWVATI
SSGGSYTYYLDSVKGRFTITRDSSTNTLYLEMSSLRSEDTALYFCAPTTVVPFA
YWGQGTLVTVSS De-immunised murine A33 $V_L$
DIQMTQSPSSMSTSVGDRVSITCKASQNVRTVVAWYQQKPGKSPKSLIYLAS
NRHTGVPSRFSGSGSGTDFLTISSVQPEDFADYFCLQHWSYPLTFGGGTKLE
VK

FIG. 27

Protein sequence of streptokinase from *Streptococcus equisimilis*

IAGPEWLLDRPSVNNSQLVVSVAGTVEGTNQDISLKFFEIDLTSRPAHGGKTEQGLSPKS
KPFATDSGAMPHKLEKADLLKAIQEQLIANVHSNDDYFEVIDFASDATITDRNGKVYFAD
KDGSVTLPTQPVQEFLLSGHVRVRPYKEKPIQNQAKSVDVEYTVQFTPLNPDDDFRPGLK
DTKLLKTLAIGDTITSQELLAQAQSILNKTHPGYTIYERDSSIVTHDNDIFRTILPMDQE
FTYHVKNREQAYEINKKSGLNEEINNTDLISEKYYVLKKGEKPYDPFDRSHLKLFTIKYV
DVNTNELLKSEQLLTASERNLDFRDLYDPRDKAKLLYNNLDAFGIMDYTLTGKVEDNHDD
TNRIITVYMGKRPEGENASYHLAYDKDRYTEEREVYSYLRYTGTPIPDNPNDK

FIG. 28

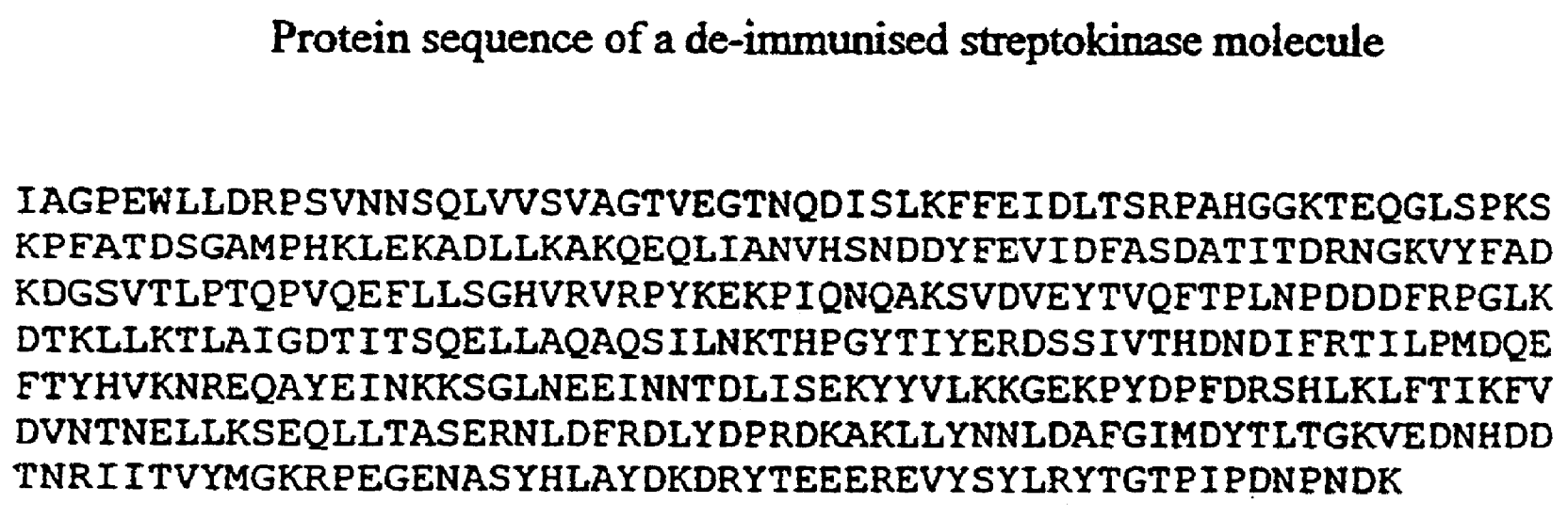

Protein sequence of a de-immunised streptokinase molecule

IAGPEWLLDRPSVNNSQLVVSVAGTVEGTNQDISLKFFEIDLTSRPAHGGKTEQGLSPKS
KPFATDSGAMPHKLEKADLLKAKQEQLIANVHSNDDYFEVIDFASDATITDRNGKVYFAD
KDGSVTLPTQPVQEFLLSGHVRVRPYKEKPIQNQAKSVDVEYTVQFTPLNPDDDFRPGLK
DTKLLKTLAIGDTITSQELLAQAQSILNKTHPGYTIYERDSSIVTHDNDIFRTILPMDQE
FTYHVKNREQAYEINKKSGLNEEINNTDLISEKYYVLKKGEKPYDPFDRSHLKLFTIKFV
DVNTNELLKSEQLLTASERNLDFRDLYDPRDKAKLLYNNLDAFGIMDYTLTGKVEDNHDD
TNRIITVYMGKRPEGENASYHLAYDKDRYTEEEREVYSYLRYTGTPIPDNPNDK

FIG. 29

METHOD FOR RENDERING STREPTOKINASE LESS IMMUNOGENIC TO A HUMAN

This application is a continuation of U.S. Ser. No. 09/438,136, filed Nov. 10, 1999; this application claims the benefit of U.S. provisional application Ser. No. 60/067,235, filed Dec. 2, 1997 under 35 U.S.C. §119(e). This application also claims priority under 35 U.S.C. 119 (a)–(d) to PCT application number GB98/01473, filed on May 21, 1998, foreign application number GB 9710480.6, filed on May 21, 1997, foreign application number GB 9716197.0, filed on May 31, 1997 in Great Britain, foreign application number GB 9725270.4, filed on Nov. 28, 1997 in Great Britain, and foreign application number GB9807751.4, filed on Apr. 14, 1998 in Great Britain.

The present invention relates to the production of substantially non-immunogenic proteins, especially antibodies, and their uses. The invention uses a combination of recombinant DNA and monoclonal antibody technology for the generation of novel therapeutic and in vivo diagnostic agents for particular use in man.

The use of rodent, especially mouse, monoclonal antibodies for therapeutic and in vivo diagnostic applications in man was found to be limited by immune responses made by patients to the rodent antibody. The development of so-called "HAMA" (human anti-mouse antibody) responses in patients was shown to limit the ability of antibodies to reach their antigenic targets resulting in a reduced effectiveness of the antibodies. In order to reduce the HAMA response, chimaeric antibodies were developed (see, for example, WO-A-8909622) in which the mouse variable (V) regions were joined to human constant (C) regions. Such antibodies have proved clinically useful although the mouse V region component still provides the basis for generating immunogenicity in patients (see, for example, LoBuglio et al., *Proc. Nat'l. Acad. Sci. USA* 86 4220–4224 (1989)). Therefore, technology for humanised antibodies were developed whereby the complementarity determining regions or "CDRs" from the rodent antibody were transplanted onto human V regions and joined to human C regions to create humanised antibodies whereby the only non-human components were the CDRs which were adjacent to human V region "frameworks". The transplanted CDRs corresponded either to hypervariable regions as defined by Kabat et al. ("Sequences of Proteins of Immunological Interest", Kabat E., et al. , US Dept. of Health and Human Services, 1983) or to the hypervariable loops in 3-dimensional structures of antibodies (Chothia and Lesk, *J. Mol. Biol.* 196 901–917 (1987)). One of the first examples of such humanised antibodies by Riechmann et al. (*Nature* 332 323–326 (1988)) illustrated, however, that simple transplantation of CDRs often resulted in reduced affinity of the humanised antibody and consequently that the introduction of certain non-human amino acids (i.e. from the corresponding position in the rodent sequence) in the human V region framework as required in order to restore affinity. A number of methods have been proposed for the substitution of human framework residues in order to restore affinity including those disclosed in EP-A-0239400, EP-A-0438310, WO-A-9109967 and WO-A-9007861. In particular, patent publications by Protein Design Labs., Inc. (e.g. WO-A-9007861 and related EP-B-0451216) purport to provide a general method for producing humanised antibodies in which one or more human framework residues are altered in order to restore binding affinity.

A common aspect of all of the above mentioned methods for production of chimeric or humanised antibodies is that the objective of these methods was to create antibodies which are substantially non-immunogenic in humans (e.g. EP-B-0451216, p3, line 6). However, the means for achieving this objective has been the introduction into the rodent antibody of as much human sequence as possible and it has been assumed that such a general introduction of human sequence will render the antibodies non-immunogenic. It is known that certain short peptide sequences ("epitopes") can be immunogenic in humans and none of the methods for chimaeric or humanised antibodies have considered how to eliminate or avoid such epitopes in the resultant antibody. Furthermore, most of the methods (e.g. EP-B-0451216) have advocated the introduction of non-human amino acids into human V region frameworks without considering the possible creation of immunogenic epitopes, and none of the methods has provided any means for avoiding or eliminating immunogenic epitopes at framework:CDR junctions and, where practical, within CDRs themselves. Thus, of the methods devised with the objective of creating substantially non-immunogenic antibodies, none can be considered as actually achieving the creation of such substantially non-immunogenic antibodies. The same can be said of proteins (especially therapeutic proteins) other than antibodies.

The present invention provides, for the first time, a general method for creating substantially non-immunogenic proteins such as antibodies and also provides antibodies and other proteins created by this method.

According to a first aspect of the invention, there is provided a method of rendering a protein, or part of a protein, non-immunogenic, or less immunogenic, to a given species, the method comprising:

(a) determining at least part of the amino acid sequence of the protein;

(b) identifying in the amino acid sequence one or more potential epitopes for T-cells ("T-cell epitopes") of the given species; and (c) modifying the amino acid sequence to eliminate at least one of the T-cell epitopes identified in step (b) thereby to eliminate or reduce the immunogenicity of the protein or part thereof when exposed to the immune system of the given species.

The term "T-cell epitopes" refers to specific peptide sequences which either bind with reasonable efficiency to MHC class II molecules or which, from previous or other studies, show the ability to stimulate T-cells via presentation on MHC class II. However, it will be understood that not all such peptide sequences will be delivered into the correct MHC class II cellular compartment for MHC class II binding or will be suitably released from a larger cellular protein for subsequent MHC class II binding. It will also be understood that even such peptides which are presented by MHC class II on the surface of antigen-presenting cells will elicit a T cell response for reasons including a lack of the appropriate T cell specificity and tolerance by the immune system to the particular peptide sequence.

Potential epitopes for B-cells of the given species may additionally be compromised in a similar manner.

The invention has particular application to rendering regions of immunoglobulins non-immunogenic (which term will be used in this specification to include less immunogenic, unless the context dictates otherwise): constant or, especially, variable regions of immunoglobulins (or of course natural or artificial molecules containing both such regions) constitute proteins, or parts of proteins, to which the invention is well suited to being applied.

However, it will be understood to those skilled in the art that the present invention could also be applied to produce therapeutic proteins other than immunoglobulins or antibodies. As with antibodies, proteins which would otherwise be immunogenic in man could be de-immunised by removal of T cell epitopes. In addition, if a reference human protein is available with similar secondary structure and identifiable surface amino acids, the B cell epitopes could additionally be removed from the protein by substituting surface amino from the reference human protein in place of the corresponding amino acids in the non-human or potentially immunogenic protein. For example, clinical use of the thrombolytic agent bacterial streptokinase is limited by human immune responses against the molecule; such molecules could be engineered to remove potential T cell epitopes in order to remove the immunogenicity.

Generally, the invention will be used to reduce the immunogenicity of a protein or part thereof (exemplified by a V region of an immunoglobulin) of a first species in relation to the immune system of a second species. The first species may be non-human, and the second species may be human. Examples of typical non-human species useful in relation to embodiments of the invention relating to immunoglobulins include mammals, especially rodents such as rats and, in particular, mice, and farm animals such as sheep and cattle. However, as made clear above in relation to bacterial streptokinase, the first species may be taxonomically far removed from the second species; when the first species is non-human, it may be non-mammalian and even non-eukaryotic. In much of the following description of preferred embodiments of the invention, reference will be made to humanising antibodies, but it is to be understood that the invention also relates to species other than man and to proteins, particularly therapeutic proteins, generally, including specific binding molecules other than whole antibodies.

The method of the invention is based on the consideration of how an immune response against a monoclonal is usually created in humans as the basis for avoiding or eliminating sequences within the antibody which are involved in this immune response. When a therapeutic antibody or other immunoglobulin, or partial immunoglobulin, molecule ("antibody", for short) is administered to a human patient, the antibody is subjected to surveillance by both the humoral and cellular arms of the immune system which will respond to the antibody if it is recognised as foreign and if the immune system is not already tolerant to the immunogenic sequence within the antibody. For the humoral immune response, immature B-cells displaying surface immunoglobulins (sIg) can bind to one or more sequences within the therapeutic antibody ("B-cell epitopes") if there is an affinity fit between the an individual sIg and the B-cell epitope and if the B-cell epitope is exposed such that sIg can access the B-cell epitope. The process of sIg binding to the therapeutic antibody can, in the presence of suitable cytokines, stimulate the B-cell to differentiate and divide to provide soluble forms of the original sIg which can complex with the therapeutic antibody to limit its effectiveness and facilitate its clearance from the patient. However, for an effective B-cell response, a parallel T-cell response is required in order to provide the cytokines and other signals necessary to give rise to soluble antibodies. An effective T-cell response requires the uptake of the therapeutic antibody by antigen-presenting cells (APCs) which can include B-cells themselves or other professional APCs such as macrophages, dendritic cells and other monocytes. In addition, non-professional APCs such as the cells to which the antibody binds can take up the therapeutic antibody and provide intermediate processing of the antibody such that professional APCs can then absorb the antibody components. Having taken up the therapeutic antibody, APCs can then present suitable peptides from the therapeutic antibody ("T-cell epitopes") complexed with MHC class II molecules at the cell surface. Such peptide-MHC class II complexes can be recognised by helper T-cells via the T-cell receptor and this results in stimulation of the T-cells and secretion of cytokines which provides "help" for B-cells in their differentiation to full antibody producing cells. In addition, the T-cell response can also result in deleterious effects on the patient for example through inflammation and allergic reactions.

An effective primary immunogenic response to a therapeutic antibody therefore usually requires a combination of B- and T-cell responses to B- and T-cell epitopes. Therefore, avoidance of a primary immunogenic response requires the avoidance or elimination of both B- and T-cell epitopes within the therapeutic antibody. Without either the B- or T-cell response, the primary immunogenic response to a therapeutic antibody is likely to be muted or absent. The present invention therefore provides methods for avoiding or eliminating T-cell epitopes, or a combination of both B- and T-cell epitopes, from therapeutic antibodies in order to create substantially non-immunogenic antibodies with particular emphasis on avoiding such epitopes in the V region of the therapeutic antibody. For B-cell epitopes, the method takes advantage of the fact sIg can only bind to accessible regions of the therapeutic antibody, ie. sequences of exposed surface amino acids. For a starting mouse antibody for subsequent human use, the method then incorporates into the V region of the therapeutic antibody, human amino acids at positions corresponding to those of the exposed mouse amino acids. For T-cell epitopes, sequences of overlapping peptides within the therapeutic antibody are analysed, with particular emphasis on the V region, in order to identify putative peptides suitable for presentation by MHC class II molecules. By scanning the V region of a potential therapeutic antibody and, where T-cell epitopes are identified, changing one or more individual amino acids to eliminate the T-cell epitope, then an antibody can be created devoid of T-cell epitopes. For the C regions of the therapeutic antibody or other immunoglobulin molecule, contiguous natural C regions from human antibodies can be used, although the invention also encompasses the identification and elimination of T-cell epitopes in the C regions if desirable or necessary.

It will be understood that the invention is not just applicable to whole antibodies, but rather to any specific binding molecule comprising a V region of an immunoglobulin, including without limitation whole Ig light ($\kappa$ and $\lambda$) and heavy ($\gamma$, $\alpha$, $\mu$, $\delta$ and $\epsilon$) chains, light/heavy chain dimers, SCAs (single-chain antibodies), and antibody or immunoglobulin fragments including those designated Fab, F(ab')$_2$, Fab', Fd and Fv.

While the usefulness of the invention is not confined to making an antibody or other V region-containing molecule of one particular species therapeutically or diagnostically administrable to any other particular species, the most significant utility of the invention will be in "humanising" non-human antibodies, particularly rodent antibodies such as murine antibodies (or parts of them). In that case, the "first species" referred to above will be a mouse, and the "second species" will be a human.

Therefore, a particular embodiment of the present invention comprises the following key steps:

(a) determining the amino acid sequence of the V region of a starting antibody, which will usually be non-human, e.g. mouse;

(b) optionally modifying the amino acid sequence, for example by recombinant DNA techniques, to change those non-CDR residues on the exposed surface of the antibody structure to the corresponding human amino acids taken from a reference (e.g. closely matched) human V region sequence (which may be a human germ-line V region sequence);

(c) analysing the amino acid sequence to identify potential T-cell epitopes and modifying the amino acid sequence, for example by recombinant DNA techniques, to change one or more residues in order to eliminate at least some, and preferably all, of the T-cell epitopes, particularly framework epitopes but including those within CDRs if this does not undesirably reduce or eliminate binding affinity or undesirably alter specificity; and (d) optionally adding human C regions via recombinant DNA to create a complete antibody which is substantially non-immunogenic.

A preferred method of the present invention therefore combines the removal of both B- and T-cell epitopes from a therapeutic antibody, a process which is termed "de-immunisation". For removal of human B-cell epitopes from the V region of a therapeutic antibody, the method of Padlan (Padlan E. A., *Molecular Immunology* 28 489–498 (1991) and EP-A-0519596) provides a suitable procedure whereby surface amino acids in a particular antibody sequence are identified with reference to 3-dimensional structures or models of antibody V regions and are converted to the corresponding human residues in a process which has been called "veneering". A derivative of this method (EP-A-0592106) models the V regions of the therapeutic antibody itself in order to identify surface amino acids in a process which has been called "resurfacing".

The present invention provides for removal of human (or other second species) T-cell epitopes from the V regions of the therapeutic antibody (or other molecule) whereby the sequences of the V region can be analysed for the presence of MHC class II-binding motifs by any suitable means. For example, a comparison may be made with databases of MHC-binding motifs such as, for example by searching the "motifs" database at the world-wide web site of the Walter and Eliza Hall Institute of Medical Research. Alternatively, MHC class II-binding peptides may be identified using computational threading methods such as those devised by Altuvia et al. (*J. Mol. Biol.* 249 244–250 (1995)) whereby consecutive overlapping peptides from the V region sequences are testing for their binding energies to MIC class II proteins. In order to assist the identification of MHC class II-binding peptides, associated sequence features which relate to successfully presented peptides such as amphipathicity and Rothbard motifs, and cleavage sites for cathepsin B and other processing enzymes can be searched for.

Having identified potential second species (e.g. human) T-cell epitopes, these epitopes are then eliminated by alteration of one or more amino acids, as required to eliminate the T-cell epitope. Usually, this will involve alteration of one or more amino acids within the T-cell epitope itself This could involve altering an amino acid adjacent the epitope in terms of the primary structure of the protein or one which is not adjacent in the primary structure but is adjacent in the secondary structure of the molecule. The usual alteration contemplated will be amino acid substitution, but it is possible that in certain circumstances amino acid addition or deletion will be appropriate. All alterations can for preference be accomplished by recombinant DNA technology, so that the final molecule may be prepared by expression from a recombinant host, for example by well established methods, but the use of protein chemistry or any other means of molecular alteration is not ruled out in the practice of the invention.

In practice, it has been recognised that potential human T-cell epitopes can be identified even in human germ-line V region framework sequences when comparison is made with databases of MHC-binding motifs. As humans do not generally mount an ongoing immune response against their own antibodies, then either humans are tolerant to these epitopes or these potential epitopes cannot be presented by human APCs because they are not processed appropriately. Therefore, such potential T-cell epitopes which are represented in germ-line V region sequences may, in practice, be retained in the de-immunised antibody. In order to minimise the creation of additional T-cell epitopes during the elimination of potential T-cell epitopes from the therapeutic antibody sequence, the elimination of T-cell epitopes is preferably (but not necessarily) achieved by conversion to second species (usually human) germ-line amino acids at positions corresponding to those of the first species (usually mouse) amino acids within T-cell epitopes. Once initially identified T-cell epitopes are removed, the de-immunised sequence may be analysed again to ensure that new T-cell epitopes have not been created and, if they have, the epitope(s) can be deleted, as described above; or the previous conversion to a corresponding human germ-line amino acid is altered by conversion of the murine (or other first species) amino acid to a similar non-human (or non-second species) amino acid (i.e. having similar size and/or charge, for example) until all T-cell epitopes are eliminated.

For the C region of a therapeutic de-immunised antibody or other molecule subjected to the method of the invention, it is not necessary to systematically eliminate potential B- and T-cell epitopes as the use of contiguous natural human C region domains has so far proved safe and substantially non-immunogenic in patients; thus the combination of de-immunised V regions and human C regions is sufficient for creation of a substantially non-immunogenic antibody or other immunoglobulin V region-containing molecule. However, as human C regions have sites of amino acid allotypic variation which might create potential T-cell epitopes for some allotypes, then the method of Lynxvale Ltd. (Clark) published in WO-A-9216562 and EP-A-0575407 might be useful. Equally, the method of the invention may be applied to a C region in a similar manner as it is applied to a V region.

For the CDRs of a therapeutic antibody, it is common for one or more potential T-cell epitopes to overlap or fall within the CDRs whereby removal of the epitopes requires alteration of residues within the CDRs. In order to eliminate the induction of a T-cell response to such epitopes, it is desirable to eliminate these although this may reduce the binding affinity of the resultant antibody and thus any potential alteration of CDRs may need to be tested for any alteration of resultant antigen binding.

A typical therapeutic de-immunised antibody from the present invention will comprise heavy and light chain V region sequences ($V_H$, $V_L$) with several amino acid substitutions which constitute departures from the prototype rodent sequence. Typically, for a $V_H$ or $V_L$ region, there will be 10 to 15 substitutions with human residues to eliminate B-cell epitopes and 1 to 10 human or non-human substitutions to eliminate T-cell epitopes. The typical therapeutic de-immunised antibody will also comprise human C regions for the heavy and light chains.

EP-B-0451216 discloses the use of at least one amino acid substitution outside of complementarity determining regions (CDRs) as defined . . . in the production of a humanized immunoglobulin, wherein said amino acid substitution is from the non-CDR variable region of a non-human donor immunoglobulin, and in which humanized immunoglobulin the variable region amino acid sequence other than the CDRs comprises at least 70 amino acid residues identical to an acceptor human immunoglobulin variable region amino acid sequence, and the CDRs are from the variable region of said non-human donor immunoglobulin.

In certain preferred de-immunised antibodies of the present invention, the variable region amino acid sequence other than the CDRs comprises fewer than 70 amino acid residues identical to an acceptor human immunoglobulin variable region amino acid sequence (ie. a reference human variable region sequence such as a germ-line variable region sequence).

EP-B-0451216 also discloses a method of producing a humanized immunoglobulin chain having a framework region from a human acceptor immunoglobulin and complementarity determining regions (CDR's) from a donor immunoglobulin capable of binding to an antigen, said method comprising substituting at least one non-CDR framework amino acid of the acceptor immunoglobulin with a corresponding amino acid from the donor immunoglobulin at a position in the immunoglobulins where:
(a) the amino acid in the human framework region of the acceptor immunoglobulin is rare for said position and the corresponding amino acid of the donor immunoglobulin is common for said position in human immunoglobulin sequences; or
(b) the amino acid is immediately adjacent to one of the CDR's; or
(c) the amino acid is predicted to have a side chain capable of interacting with the antigen or with the CDR's of the humanized immunoglobulin.

In the present invention, preferred de-immunised antibody variable region amino acid sequence other than CDRs would exclude amino acids from the starting antibody which are rare at the corresponding position in human immunoglobulins or which are adjacent to CDRs or which have a side-chain capable of interacting with the antigen or with the CDRs of the de-immunised antibody.

It will be understood by those skilled in the art that there can be several variations of the method of the present invention which will fall within the scope of the present invention. Whilst the present invention relates principally to therapeutic antibodies from which human B- and T-cell epitopes have been deleted, it will be recognised that the removal of T-cell epitopes alone might, in some cases, also be effective in avoiding an immunogenic response in patients. As an alternative to the de-immunised antibodies of the present invention, part of the method of the first aspect of the present invention may be used to analyse pre-existing antibodies in therapeutic use in order to predict the basis for immunogenic responses to these antibodies and to eliminate them by induction of B- or T-cell tolerance to the appropriate B- and T-cell epitopes or by other methods for ablating the immune response. In addition, it should be considered within the scope of the present invention to redesign a pre-existing therapeutic antibody to which a human immune response has been detected and characterised to delete the epitopes relating to the observed immune response in humans. Additionally, as discussed above, therapeutic and other proteins apart from antibodies may benefit from the application of the invention.

It should be understood that the method of the present invention could be used to render a V region of an immunoglobulin either wholly non-immunogenic or partially immunogenic, whereby certain B- or T-cell epitopes may be left within the final molecule in order to elicit an immune reaction in patients, for example with an anti-idiotype antibody where only usually part of the V region is involved in mimicking the original antigen. It should also be understood that the present invention can apply to the production of antibodies for uses other than in human medicine and that de-immunised antibodies could be produced for specific therapeutic or diagnostic use in animals whereby de-immunisation eliminates the specific animal's B- and T-cell epitopes.

As indicated above, the method of the present invention may also be used to render constant regions of immunoglobulins non-immunogenic. For example, in a typical humanisation of a non-human antibody, instead of incorporating a human constant region into the final molecule, the non-human constant region could be screened for the presence of T cell epitopes which would then be eliminated preferably without altering any of the biochemical properties of the constant region such as the ability to fix complement. Alternatively, the equivalent human biological properties could be deliberately incorporated into the de-immunised constant regions by incorporating corresponding human residues, for example for binding to efficient binding to human Fc receptors. If required, certain properties of non-human constant regions could be retained in the de-immunised constant regions, for example to retain the co-operative binding effect of mouse IgG3 antibodies.

According to a second aspect of the invention, there is provided a molecule of a first species (such as a non-human species), wherein the variable region is modified to eliminate epitopes for T-cells, and optionally also epitopes for B-cells, of a second species (such as human). The molecule will generally be proteinaceous and may comprising at least a variable region of an immunoglobulin, in which case the first species may be mouse. The variable region may be modified to the minimum extent necessary to eliminate the T-cell epitopes. Alternatively or additionally, it may be modified to eliminate only T-cell epitopes which are non-germ-line.

The invention extends also to a molecule which has been prepared by a method in accordance with the first aspect of the invention.

The invention has particular and widespread application in the field of therapeutic molecules including monoclonal antibodies whereby rodent or other non-human antibodies can be de-immunised for applications in humans and whereby previously humanised or chimaeric antibodies with B- or T-cell epitopes could be converted into a less immunogenic form for use in humans. It will also be understood that even antibodies derived from human immunoglobulin genes such as antibodies derived from bacteriophage-display libraries (Marks et al., *J. Mol. Biol.* 222 581–597 (1991)), transgenic mice with human immunoglobulin genes (Bruggermann et al., *Proc. Nat'l. Acad. Sci. USA* 86 6709–6713 (1989)) and natural human monoclonal antibodies can carry B- and T-cell epitopes especially as somatic mutations are introduced into framework sequences in immunoglobulin genes during the maturation of antibodies.

Therefore, de-immunisation may be required in order to prepare such antibodies for use in humans. Finally, it will be understood that CDRs from any naturally derived antibodies have been subjected to selection by somatic mutation of V region genes and thus might have T-cell epitopes capable of triggering immune responses in humans. The de-immunisation method might be applicable without severe loss of antibody binding affinity (depending on the contribution of particular CDRs to antigen binding).

According to a third aspect of the invention, there is provided a molecule which has been prepared by a method in accordance with the first aspect of the invention, or a molecule in accordance with the second aspect, for use in medicine or diagnosis.

According to a fourth aspect of the invention, there is provided the use of a molecule prepared by a method in accordance with the first aspect of the invention, or a molecule in accordance with the second aspect, in the manufacture of an therapeutic or diagnostic antibody or other specific binding molecule. The invention therefore extends to a method of treating or preventing a disease or condition, the method comprising administering to a subject an effective amount of a molecule prepared by a method in accordance with the first aspect of the invention, or a molecule in accordance with the second aspect. The invention also extends to the use of such molecules in in vivo and in vitro diagnosis.

Preferred features of each aspect of the invention are as for each other aspect, mutatis mutandis.

The invention will now be illustrated, but not limited, by the following examples. The examples refer to the drawings, in which:

FIG. 1 shows the DNA sequences of 340 $V_H$ (SEQ ID NO: 88) and $V_L$ (SEQ ID NO:89);

FIG. 2 shows the protein sequence of 340 murine $V_H$ (SEQ ID NO: 90) and $V_L$ (SEQ ID NO:91);

FIG. 3 shows the protein sequence of humanised 340 $V_H$ (SEQ ID NO: 92) and $V_L$ (SEQ ID NO:93);

FIG. 4A shows oligonucleotides for construction of humanised 340 $V_H$ and $V_K$; VH1 (SEQ ID NO: 94), VH2 (SEQ ID NO: 95), VH3 (SEQ ID NO: 96), VH4 (SEQ ID NO: 97), VK1 (SEQ ID NO: 98);

FIG. 4B shows oligonucleotides for construction of humanised 340 $V_H$ and $V_K$; VK2 (SEQ ID NO: 99), VK3 (SEQ ID NO: 100), VK4 (SEQ ID NO: 101), VH5 (SEQ ID NO: 102), VH6 (SEQ ID NO: 103), VK5 (SEQ ID NO: 104) VK6 (SEQ ID NO: 105);

FIG. 4C shows oligonucleotides for construction of humanised 340 $V_H$ and $V_K$; VH/VK1 (SEQ ID NO: 106), VH7 (SEQ ID NO: 107), VK7 (SEQ ID NO: 108), VH8 (SEQ ID NO: 109), VH9 (SEQ ID NO: 110), VK8 (SEQ ID NO: 111), VK9 (SEQ ID NO: 112);

FIG. 5 shows the protein sequence of de-immunised 340 $V_H$ SEQ ID NO: 113) and $V_L$ (SEQ ID NO: 114);

FIG. 6A shows oligonucleotides for construction of de-immunised 340 $V_H$ and $V_K$; VH1 (SEQ ID NO: 115), VH2 (SEQ ID NO: 116);

FIG. 6B shows oligonucleotides for construction of de-immunised 340 $V_H$ and $V_K$; VH3 (SEQ ID NO: 117), VH4 (SEQ ID NO: 118), VK1 (SEQ ID NO: 119), VK2 (SEQ ID NO: 120), VK3 (SEQ ID NO: 121), VK4 (SEQ ID NO: 122) VK6 (SEQ ID NO: 123), VK8 (SEQ ID NO: 129);

FIG. 7 shows the comparative binding of humanised, de-immunised and chimaeric antibody to an epidermal growth factor receptor (EGFR) preparation from;

FIG. 8 shows the protein sequence of humanized 340 $V_H$ (SEQ ID NO: 125) compared with the sequence with murine epitopes inserted (labeled "altered", SEQ ID NO: 126);

FIG. 9 shows oligonucleotide primers for insertion of murine epitopes into humanized 340 $V_H$ by SOE PCR; sequences numbered from top to bottom being: (SEQ ID NO: 127, 128, 129, 130, 131 and 132);

FIG. 10 shows the protein sequence of mouse de-immunised 340 $V_H$ (SEQ ID NO: 133);

FIG. 11 shows oligonucleotide primers for construction of mouse de-immunised $V_H$; VH1 (SEQ ID NO: 134), VH2 (SEQ ID NO: 135), VH3 (SEQ ID NO: 136), VH4 (SEQ ID NO: 137), VH5 (SEQ ID NO: 138), VH6 (SEQ ID NO: 139);

FIG. 12 shows the primary and secondary immunogenic responses to antibodies in accordance with the invention and contrasts them with immunogenic responses to antibodies not within the scope of the invention;

FIG. 13 shows DNA sequences of murine 708 $V_H$ (SEQ ID NO: 140) and $V_L$ (SEQ ID NO: 141);

FIG. 14 shows protein sequences of murine 708 $V_H$ (SEQ ID NO: 142) and $V_L$ (SEQ ID NO: 143);

FIG. 15 shows DNA sequences of de-immunised 708 $V_H$ (SEQ ID NO: 144) and $V_L$ (SEQ ID NO: 145);

FIG. 16A shows oligonucleotides for construction of de-immunised 708 $V_H$ and $V_L$; DIVH1 (SEQ ID NO: 146), DIVH2 (SEQ ID NO: 147), DIVH3 (SEQ ID NO: 148), DIVH4 (SEQ ID NO: 149), DIVH5 (SEQ ID NO: 150), DIVH6 (SEQ ID NO: 151);

FIG. 16B shows oligonucleotides for construction of de-immunized 708 $V_H$ and $V_L$; DIVK1 (SEQ ID NO: 152), DIVK2 (SEQ ID NO: 153), DIVK3 (SEQ ID NO: 154), DIVK4 (SEQ ID NO: 155), DIVK5 (SEQ ID NO: 156), DIVH7 (SEQ ID NO: 157), DIVH8 (SEQ ID NO: 158), DIVK6 (SEQ ID NO; 159), DIVK7 (SEQ ID NO: 160);

FIG. 16C shows oligonucleotides for construction of de-immunized 708 $V_H$ and $V_L$; VH/VK1 (SEQ ID NO: 161), DIVH9 (SEQ ID NO: 162), DIVK8 (SEQ ID NO: 163), DIVH10 (SEQ ID NO: 164), DIVH11 (SEQ ID NO: 165), DIVK9 (SEQ ID NO: 166), DIVK10 (SEQ ID NO: 167);

FIG. 17 shows protein sequences of Vaccine 1 708 $V_H$ (SEQ ID NO: 168) and $V_L$ (SEQ ID NO: 169);

FIG. 18A shows oligonucleotides for construction of Vaccine 1 708 $V_H$ and $V_L$; VHDT340R (SEQ ID NO: 170), VHDT322F (SEQ ID NO: 171), and VHDT446F (SEQ ID NO: 172)

FIG. 18B shows oligonucleotides for construction of Vaccine 1 708 $V_H$ and $V_L$; top sequence (SEQ ID NO: 173), VHDT570F (SEQ ID NO: 174), VHDT587R (SEQ ID NO: 175), VKDT322F (SEQ ID NO: 176), VKDT340R (SEQ ID NO: 177), VKDT446F (SEQ ID NO: 178), VKDT463R (SEQ ID NO: 179), VKDT570F (SEQ ID NO: 180), VKDT587R (SEQ ID NO: 181);

FIG. 18C shows oligonucleotides for construction of Vaccine 1 708 $V_H$ and $V_L$; VH261F (SEQ ID NO: 182), VH611R (SEQ ID NO: 183), VK261F (SEQ ID NO: 184), VK12 (SEQ ID NO: 185), VH/VK1 (SEQ ID NO: 186), VH276R (SEQ ID NO: 187), VK275R (SEQ ID NO: 188), VH597F (SEQ ID NO: 189), VH12 (SEQ ID NO: 190);

FIG. 19 shows protein sequences of Vaccine 2 708 $V_H$ (SEQ ID NO: 191) and $V_L$ (SEQ ID NO: 192);

FIG. 20A shows oligonucleotides for construction of Vaccine 2 708 $V_H$ and $V_L$; VHDT340R (SEQ ID NO: 193), VHDT322F, (SEQ ID NO: 194), VHCEA447F (SEQ ID NO: 195);

FIG. 20B shows oligonucleotides for construction of Vaccine 2 708 $V_H$ and $V_L$; VHCEA463R (SEQ ID NO: 196), VHCEA570F (SEQ ID NO: 197), VHCEA586R (SEQ ID NO: 198), VKCEA324F (SEQ ID NO: 199), VKCEA340R (SEQ ID NO: 200), VKCEA450F (SEQ ID NO: 201), VKCEA486R (SEQ ID NO: 202), VKCEA576F (SEQ ID NO: 203), VKCEA592R (SEQ ID NO: 204);

FIG. 20C shows oligonucleotides for construction of Vaccine 2 708 $V_H$ and $V_L$; VH261F (SEQ ID NO: 205), VH611R2 (SEQ ID NO: 206), VK261F (SEQ ID NO: 207), VK12 (SEQ ID NO: 185), VH/VK1 (SEQ ID NO: 209), VH276R (SEQ ID NO: 210), VK275R (SEQ ID NO: 211), VH597F (SEQ ID NO: 212), VH12 (SEQ ID NO: 213);

FIG. 21 shows the protein sequence of Vaccine 3 708 $V_H$ (SEQ ID NO: 214);

FIG. 22A shows oligonucleotides for construction of Vaccine 3 708 $V_H$; VHCD340R (SEQ ID NO: 215), VHCD322F (SEQ ID NO: 216), VHCD463R (SEQ ID NO: 217);

FIG. 22B shows oligonucleotides for construction of Vaccine 3 708 $V_H$; VHCEA447F (SEQ ID NO: 218), VHCEA570F (SEQ ID NO: 219), VHCEA586R (SEQ ID NO: 220), VH261F (SEQ ID NO: 221), VH611R2 (SEQ ID NO: 222), VH/VK1 (SEQ ID NO: 223), VH276R (SEQ ID NO: 224), VH597F (SEQ ID NO: 225), VH12 (SEQ ID NO: 226);

FIG. 23A shows oligonucleotides for construction of chimaeric 708 $V_H$ and $V_L$; VHCH355R (SEQ ID NO: 227), VHCH337F (SEQ ID NO: 228), VHCH525R (SEQ ID NO: 229), VHCH507F (SEQ ID NO: 230), VKCH345F (SEQ ID NO: 231), VKCH364R (SEQ ID NO: 232), VKCH518F (SEQ ID NO: 233), VKCH533R (SEQ ID NO: 234);

FIG. 23B shows oligonucleotides for construction of chimaeric 708 $V_H$ and $V_L$; VH261F (SEQ ID NO: 235), VH611R (SEQ ID NO: 236), VK261F (SEQ ID NO: 237), VK12 (SEQ ID NO: 238), VH/VK1 (SEQ ID NO: 239), VH276R (SEQ ID NO: 240), VK275R (SEQ ID NO: 241), VH597F (SEQ ID NO: 242), VH12 (SEQ ID NO: 243);

FIG. 24 shows the protein sequence of humanised A33 $V_H$ (SEQ ID NO: 244) and $V_L$ (SEQ ID NO: 245);

FIG. 25 shows the protein sequence of de-immunised humanised A33 $V_H$ (SEQ ID NO: 246) and $V_L$ (SEQ ID NO: 247);

FIG. 26 shows the protein sequence of murine A33 $V_H$ (SEQ ID NO: 248) and $V_L$ (SEQ ID NO: 249);

FIG. 27 shows the protein sequence of de-immunised murine A33 $V_H$ (SEQ ID NO: 250) and $V_L$ (SEQ ID NO: 251);

FIG. 28 shows the protein sequence of streptokinase (SEQ ID NO: 252) from *Streptococcus equisimililis*; and FIG. 29 shows the protein sequence of a de-immunized streptokinase molecule (SEQ ID NO: 253).

Figure 7:
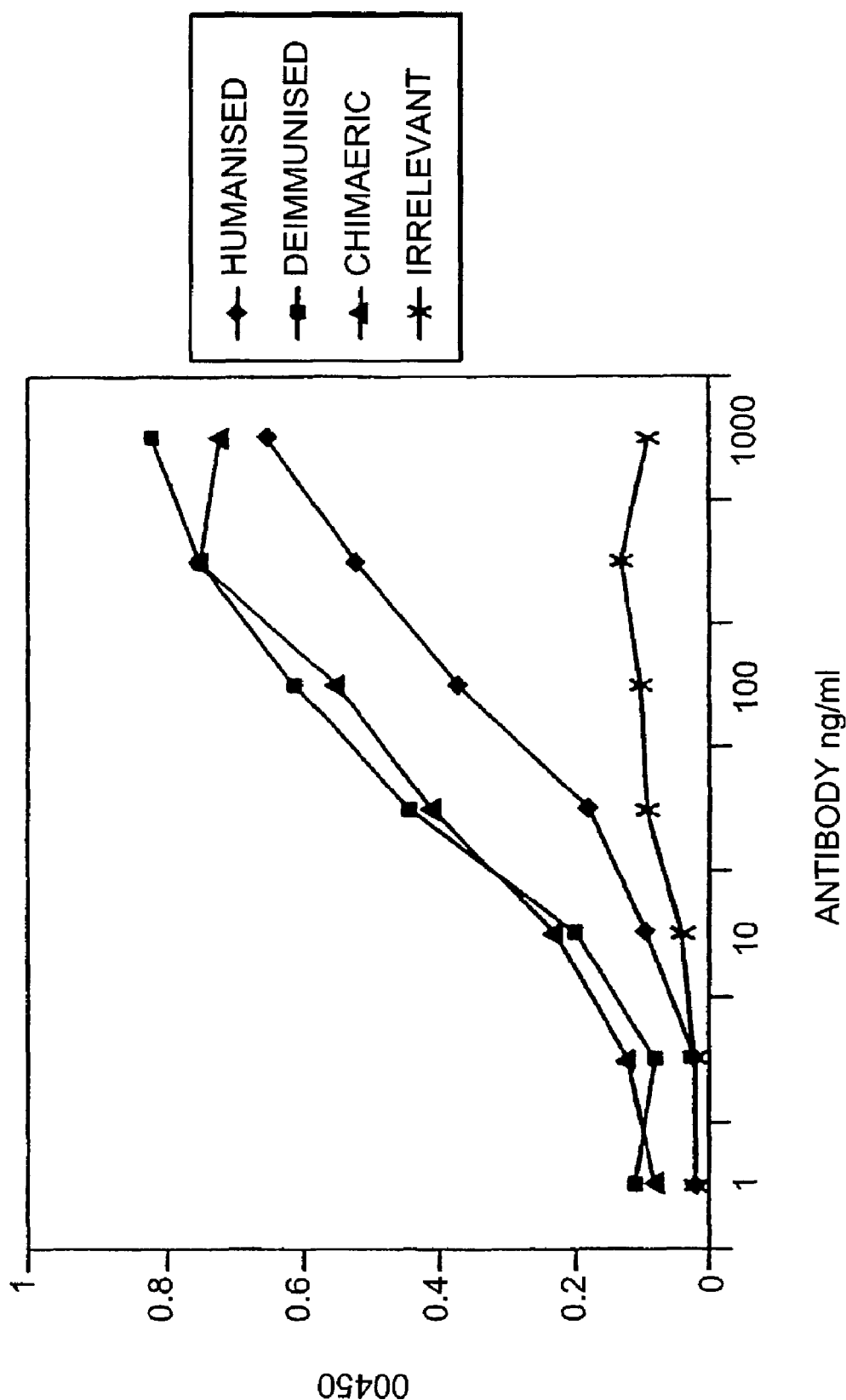
Figure 12:
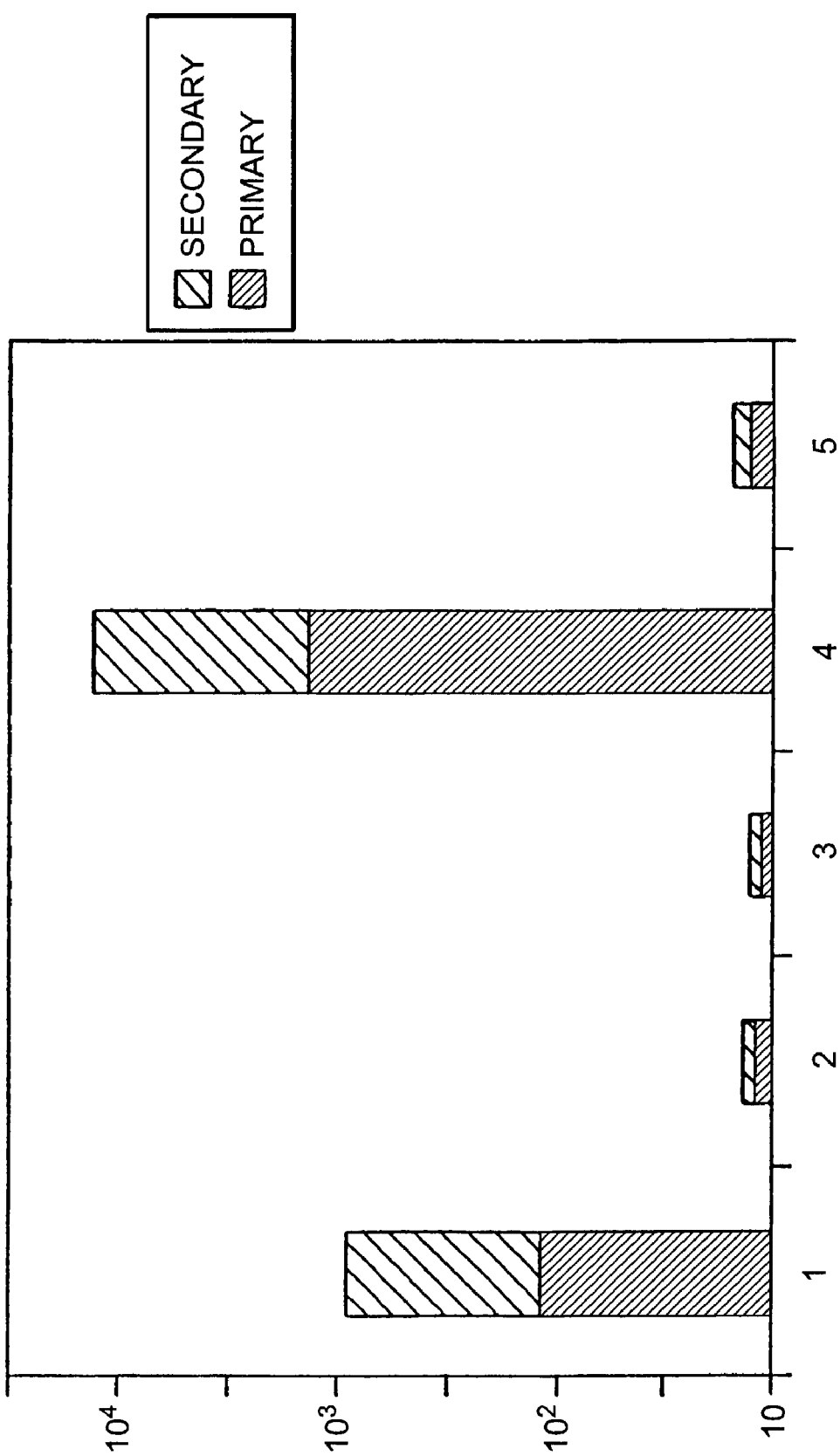

EXAMPLE residues in the frameworks from the human germ-line V region sequences HSIGDP54 (SEQ ID NO: 1) for $V_H$ and HSIGKV38(SEQ ID NO: 2) for $V_L$. Then, the resultant sequences were analysed by searching a database of human MHC class II binding peptides ("motif" at the world-wide web site of the Walter and Ehiza Hall Institute of Medical Research) for motifs present in the veneered $V_H$ and $V_L$ sequences. In parallel, databases of human $V_H$ and $V_L$ germ-line sequences (Tomlinson, et al., ibid.; Cox, et al., *Eur. J. Immunol.,* 24: 827 (1994); other germ-line sequences retrieved from EMBL, GenBank and Swiss Protein databases) were also searched for human MHC class binding motifs. Motifs appearing in the veneered antibody sequence which were also present in the germ-line were not considered further. For motifs present in the veneered $V_H$ and $V_L$ sequences and not present in the germ-line database, single amino acid substitutions to the corresponding human germ-line sequences were made in order to delete the motif unless a substitution was required within a CDR. Following this round of motif deletion, the resultant sequence was checked for generation of new MHC class II binding motifs and these were similarly deleted if present. The resultant de-immunised $V_H$ and $V_L$ sequences are shown in FIG. 5. The de-immunised $V_H$ and $V_L$ regions were constructed as above by the method of Daugherty, et al. (ibid.) using oligonucleotides synthesised with adjacent 18 nucleotide overlaps as detailed in FIG. 6. Cloning, sequencing, addition of C regions and expression in NS0 cells was as for the humanised antibody.

A chimaeric antibody comprising murine 340 $V_H$ and $V_L$ regions and human IgG1/kappa C regions was generated as detailed in Orlandi et al., ibid.

Comparative antibody binding to an epidermal growth factor receptor (EGFR) preparation from placenta. 30–40 g of human placenta was washed in PBS containing phenyl methyl sulphonyl, chopped finely, homogenised, lysed in 1% NP-40 and centrifuged at 10,000 g for 10 minutes. The supernatant was then loaded onto a CNBr-activated antibody 340 column (2 mg antibody per ml of gel) and eluted fractions were monitored by SDS-PAGE and protein analysis. ELISA plates were coated with fractions of EGFR preparation to give OD450 of 1.0 with murine 340 antibody using anti-mouse IgG peroxidase conjugate (Sigma). 1005 μl serial dilutions of the test recombinant antibodies and an irrelevant humanised antibody were incubated overnight in the ELISA plates and detected using peroxidase-labelled gamma chain-specific anti-human IgG antibody (Sigma). Results are shown in FIG. 7 and these show that the de-immunised antibody bound to the EGFR antigen with similar efficiency to the chimaeric antibody with the humanised antibody displaying an approximate five-fold deficit in binding.

EXAMPLE 2

In this example, a range of antibodies were tested in mice to compare immune responses. As a source of antibody to elicit an immune response in mice, the humanised $V_H$ fragment from Example 1 was deliberately altered to insert two murine MHC class II epitopes as shown in FIG. 8. This was undertaken by SOE PCR (Higuchi et al., *Nucleic Acids Research,* 16 7351 (1988)) using primers as detailed in FIG. 9. Using methods as in Example 1, for the murine de-immunised version the MHC class II epitopes were removed from the altered humanised $V_H$ fragment and this was also veneered to substitute exposed residues from the murine 340 sequence. The resultant sequence is shown in FIG. 10 and the synthetic oligonucleotides used shown in FIG. 11.

The murine de-immunised $V_H$ fragment from above and the humanised and murine $V_H$ fragments from Example 1 were joined either to human or murine C region fragments of isotype IgG2. For human, a 7.2 kb HindIII-BamHI genomic fragment from IgG2 C region (Bruggemann et al., *J. Exp. Med.,* 166 1351 (1987)) was used and, for murine, a 4.2 kb EcoRI-BglII fragment from mouse IgG2$b^b$ (Ollo and Rougeon, *Nature,* 296 761 (1982)) was used. Fragments were blunt-ended using the Klenow fragment of DNA polymerase and BglII linkers were added (according to the manufacturer's instructions (New England Biolabs, Beverly, Mass., USA) for cloning into the BamHI site of pSVgpt (Riechmann, ibid.). Recombinant plasmids were transfected by electroporation into J558L cells which secrete lambda light chains. Antibodies were purified from culture supernatants by protein A affinity chromatography as above.

To study immune responses, groups of five 6–8 week-old female BALB/c or C57BL/6 mice were injected intraperitoneally with 40 μg of recombinant antibody or murine 340 antibody in CFA. Serum was taken for analysis after 30 days and mice were boosted with the same antibodies in IFA; serum was again taken 10 days later. Antibody responses were measured in ELISA assays with the immobilised antibody used for immunisation. Dilutions of sera were added and incubated for 2 hrs at 37 c. Binding was then detected using biotinylated anti-mouse kappa chain antibody (Harlan-Seralab, Crawley, UK) and HRP-streptavidin (Pierce and Warriner, Chester, UK) according to the supplier's instructions. Colour was developed with OPD (o-phenylenediamine) substrate (Sigma, Poole, UK). The results were expressed as serial dilutions from an average of 5 mice per group, (SD<20%) which gave half maximum binding to immobilised antibody on the ELISA plate.

The results are shown in FIG. 12 which shows a strong primary and secondary immunogenic response to the antibodies with the humanised but not the De-immunised or murine $V_H$ regions and a murine heavy chain C region (lanes 1, 2 and 3 respectively). For the de-immunised $V_H$ with a human heavy chain C region (lane 4), a considerable primary and secondary immune response was found which was absent with the mouse 340 antibody control (lane 5).

EXAMPLE 3 mRNA was isolated from $5\times10^6$ hybridoma 708 cells (Durrant et al., *Int. J. Cancer,* 50 811 (1992) using TRIZOL™ reagent (Life Technologies, Paisley, UK) according to the manufacturers' instructions. The mRNA was converted to cDNA/mRNA hybrid using READY-TO-GO™ T-primed First Strand Kit (Pharmacia Biotech, St. Albans, UK). Variable region heavy ($V_H$) and light ($V_L$) chain cDNAs were amplified using the primer sets using the method of Jones and Bendig (*Bio/Technology,* 9 188 (1991)). PCR products were cloned into pBLUESCRIPT II SK (Stratagene, Cambridge, UK) or pCRTM 3 (Invitrogen, The Netherlands) and six individual clones each of $V_H$ and $V_L$ were sequenced ion both directions using the Applied Biosystems automated sequencer model 373A (Applied Biosystems, Warrington, UK). Resultant $V_H$ and $V_L$ sequences are shown in FIG. 13 and the corresponding protein sequences in FIG. 14.

A de-immunised antibody was generated by analysis of the sequence of FIG. 14. To remove B cell epitopes, the "veneering" method of Padlan (Padlan E. A., *Molecular Immunology* 28 489 (1991) and EP-A-0519596) was applied whereby exposed (mE or Ex) residues in the murine 708 $V_H$ or $V_L$ sequences were substituted by the corresponding residues in the frameworks from the human germ-line sequences DP-30 for $V_H$ (Tomlinson et al., *J. Mol. Biol.* 227 776 (1992) with human $J_H1$ and DPK-1 (Cox et al., *Eur. J. Immunol.*, 24 827 (1994)) for $V_L$ with human $J_78 4$. Then, the resultant sequences were analysed by searching a database of human MHC Class II binding peptides ("motif" at the World Wide Web site wehil.wehi.edu.ac) for motifs present in the veneered $V_H$ and $V_L$ sequences. In parallel, databases of human $V_H$ and $V_L$ germ-line sequences (Tomlinson et al., ibid.; Cox et al. ibid.; other germ-line sequences retrieved from EMBL, GenBank and Swiss Protein databases) were also searched for human MHC Class H binding motifs. Motifs appearing in the veneered antibody sequence which were also present in the germ-line were not considered further. For motifs present in the veneered $V_H$ and $V_L$ sequences and not present in the germ-line database, single amino acid substitutions were made in order to delete the motifs, using residues found at this position in human germ-line antibody sequences, unless a substitution was required within a CDR. Following this round of motif deletion, the resultant sequences were checked for generation of new MHC Class II motifs which were similarly deleted if present. The resultant de-immunised $V_H$ and $V_L$ sequences are shown in FIG. 15. The de-immunised $V_H$ and $V_L$ were constructed as described for the 340 antibody by the method of Daugherty BL et al. (*Nucleic Acids Research* 19 2471, 1991) using long synthetic oligonucleotides. The required sequence was synthesised as 5 or 6 long oligonucleotides (DIVH1 to DIVH6 and DIVK1 to DIVK5, shown in FIG. 16) with complementary overlapping ends of 18 base pairs. These were used in PCR with two external primers (DIVH7, DIVH8, DIVK6, DIVH7, shown in FIG. 16) resulting in the formation and subsequent amplification of full length V regions (351 bp for $V_H$ and 321 bp for $V_L$). DNAs of the vectors M13-VHPCR1 and M13-VKPCR1 (Orlandi R, Gussow D, Jones P, Winter G. *Proc. Nat'l. Acad. Sci. USA*, 86 3833 (1989)) were used as templates to produce a further two overlapping PCR fragments for each of $V_H$ and $V_L$ including 5' flanking sequence with the murine heavy chain immunoglobulin promoter and encoding the leader signal peptide (primers VHVK1 and DIVH9 for $V_H$, VHVK1 and DIVK8 for $V_L$, shown in FIG. 16) and 3' flanking sequence including a splice site and intron sequences (primers DIVH10 and DIVH11 for $V_H$, DIVK9 and DIVK10 for $V_L$, shown in FIG. 16). The DNA fragments so produced for each of $V_H$ and $V_L$ were combined in a second PCR using outer flanking primers (VHVK1 and DIVH11 for $V_H$, VHVK1 and DIVK10 for $V_L$, shown in FIG. 16) to obtain the required full length DNA sequences. Cloning, sequencing, addition of human C regions and expression in NSO cells was as for the 340 antibody (Example 1).

EXAMPLE 4

A set of vaccine molecules were constructed based on the 708 antibody. As before, the various $V_H$ and $V_L$ molecules were assembled from long synthetic oligonucleotides using the method of PCR recombination (Daugherty et al, ibid.). Cloning, sequencing, addition of human IgG1 and κ constant regions and expression in NS0 cells was as for the 340 antibody (Example 1).

The first antibody vaccine ("Vaccine 1") comprised the 708 heavy and light chains from which all potential human T cell epitopes have been removed from both antibody chains, using the method described in Example 1, including epitopes found in the CDRs, apart from the region encompassing CDRs 2 and 3 and framework 3 of the heavy chain which contains the desired human epitopes. The antibody chains were not "veneered" to remove B cell epitopes. The resultant protein sequences are shown in FIG. 17. The oligonucleotides for assembly of 708 Vaccine 1 $V_H$ and $V_K$ are shown in FIG. 18. The primary PCR used oligonucleotides VHDT322F, VHDT446F, VHDT570F, VHDT340R, VHDT463R, VHDT587R, VKDT570F, VH261F and VH611R for $V_H$ and oligonucleotides VKDT340R, VKDT322F, VKDT463R, VKDT446F, VKDT587R, VKDT570F, VK261F and VK12 resulting in the formation and subsequent amplification of full length V regions (350 bp for $V_H$ and 396 bp for $V_L$). DNAs of the vectors M13-VHPCR1 and M13-VKPCR1 (Orlandi et al., ibid.) were used as templates to produce a further two overlapping PCR fragments for $V_H$ including 5' flanking sequence with the murine heavy chain immunoglobulin promoter and encoding the leader signal peptide (primers VHVK1 and VH276R) and 3' flanking sequence including a splice site and intron sequences (primers VH597F and VH12) and one overlapping PCR fragment for $V_L$ including 5' flanking sequence with the murine heavy chain immunoglobulin promoter and encoding the leader signal peptide (primers VHVK1 and VK275R), the 3' $V_L$ sequences being included in the structural oligonucleotides. The DNA fragments so produced for each of $V_H$ and $V_L$ were combined in a second PCR using outer flanking primers (VHVK1 and VH12 for $V_H$, VHVK1 and VK12 for $V_L$) to obtain the required full length DNA sequences.

The second antibody vaccine ("Vaccine 2") comprised 708 heavy and light chains with epitopes from carcinoembryonic antigen (CEA) inserted into CDRH2 and CDRH3 and CDRL1 and CDRL3. The resultant sequence was checked using the method described in Example 1 for generation of new human T cell epitopes apart from those deliberately inserted. Single amino acid substitutions were made in the framework regions in order to remove any additional epitopes detected. The final protein sequences are shown in FIG. 19. The oligonucleotides for assembly of 708 Vaccine 2 $V_H$ and $V_K$ are shown in FIG. 20. The primary PCR used oligonucleotides VHDT340R, VHDT322F, VHCEA463R, VHCEA447F, VHCEA586R, VHCEA570F, VH261F and VH611R2 for $V_H$ and VKCEA324F, VKCEA340R, VKCEA450F, VKCEA486R, VKCEA576F, VKCEA592R, VK261F and VK12 for $V_L$ 5' and 3' flanking sequences were added as described for the first antibody vaccine constructs.

The third antibody vaccine ("Vaccine 3") comprised 708 antibody with CEA and CD55 epitopes inserted. The heavy chain was as Vaccine 2, with an epitope from CD55 inserted from position 14 to 33 (Framework 1 into CDR1). The resultant sequence was checked using the method described in Example 1 for generation of new human T cell epitopes apart from those deliberately inserted. Single amino acid substitutions were made in the framework regions in order to remove any additional epitopes detected. The final protein sequence is shown in FIG. 21. The light chain is as Vaccine 2. The oligonucleotides for assembly of 708 Vaccine 3 $V_H$ are shown in FIG. 22. The primary PCR used oligonucleotides VHCD322F, VHCD340R, VHCD463R, VHCEA447F, VHCEA570F, VHCEA586R, VH261F and VH6112R2. 5' and 3' flanking sequences were added as described for the first antibody vaccine constructs.

A chimaeric 708 antibody was prepared to provide a control for comparison with the above antibody vaccine constructs. This consisted of 708 murine variable regions combined with human IgG1 and κ constant regions. The oligonucleotides for assembly of 708 chimaeric $V_H$ and $V_K$ are shown in FIG. 23. The primary PCR used oligonucleotides VHCH355R, VHCH337F, VHCH525R, VHCH507F, VH261F and VH611R for $V_H$ and VKCH364R, VKCH345F, VKCH533R, VKCH518F, VK261F and VK12 for $V_L$. 5' and 3' flanking sequences were added as described for the first antibody vaccine constructs.

EXAMPLE 5

The present invention provides a method for the redesign of a pre-existing therapeutic antibody to which a human immune response has been detected. The invention provides the method by which the therapeutic antibody may be characterised to identify epitopes relating to the observed immune response in humans. An example of this is provided in a humanised version of monoclonal antibody A33. The monoclonal antibody (mAb) A33 antigen is a transmembrane glycoprotein expressed in normal colonic and bowel epithelium and >95% of human colon cancers. The A33 antigen has been considered a useful target for colon cancer radioimmunotherapy and encouraging pre-clinical data documented (Heath J. K. et al., *Proc. Nat'l. Acad. Sci. USA* 94 469–474 (1997)). A humanised version of mAb A33 has been produced using the CDR grafting strategy described elsewhere (WO-A-9109967, Adair J. R. et al.). Clinical trials of the humanised antibody were conducted during which a HAMA response to humanised mAb A33 was reported in a number of patients. In the present example, the variable region protein sequences for the humanised A33 antibody (FIG. 24) have been individually analysed by a novel process of peptide threading and by reference to a database of MHC-binding motifs. By these means, potentially immunogenic epitopes have been identified. In this example a method for the elimination and therefore de-immunisation of the potentially immunogenic epitopes is disclosed.

Potential MHC class II binding motifs in the variable region protein sequences of humanised antibody A33 were identified by the following method of peptide threading. The procedure involves computing a score for all possible candidate binding motifs (peptides) by considering the predicted three-dimensional conformations and interactions between an MHC class II molecule and the peptide complex. The computed score indicates the predicted binding affinity for the particular peptide and MHC allele, and is used to predict peptides likely to bind, or not to bind, with the particular MHC allele.

The HLA-DRB1*0101 molecule is currently the only example of a class II MHC molecule for which the structure is available (Stern et al., *Nature* 368 215–221 (1994)). This structure was used to predict peptide binding with HLA-DRB1. To predict peptide binding to other class II MHC alleles, models for particular alleles were constructed based on the known HLA-DRB1 structure. Models were constructed assuming the backbone structure of all class II MHC alleles are identical to HLA-DRB1. This assumption is supported by experimental data (Ghosh P. et al., *Nature* 378 457–462 (1995)) and the high degree of homology between different MHC class II molecules. Models were built by identification of the sequence differences between the known HLA-DRB1 structure and the target allele. Side-chains in the known structure were replaced to match the target allele. The side-chain conformation near the binding groove were adjusted to give favourable steric and electrostatic arrangement whilst maintaining the largest possible binding pocket. The latter feature of the approach is significant in ensuring that modelled peptide side-chains are most readily accommodated within the binding groove, so reducing the number of candidate fragments rejected due to steric overlap with the MHC.

The structural data of HLA-DRB1*0101 was obtained from the Protein Data Bank (Bernstein F. C. et al., *J. Mol. Biol.* 112 535–542 (1977)). The ten most frequent HLA-DRB1 alleles in the human Caucasian population were modelled on the HLA-DRB1*0101 structure. Homology modelling of HLA-DRB1*03011, HLA-DRB1*0302, HLA-DRB1*0401, HLA-DRB1*0801, HLA-DRB1*09011, HLA-DRB1*11011, HLA-DRB1*1201, HLA-DRB1*1301, HLA-DRB1*1401 and HLA-DRB1*15011 was conducted using molecular the modelling package "Quanta" (Molecular Simulations Inc, University of York, England). Side-chain conformations in amino acids differing between a particular target allele and the HLA-DRB1*0101 solved structure were adjusted interactively. In most cases, torsion angles were chosen to result in minimal or nil steric overlap between mutated residues and surrounding atoms. Where non-conserved residues which were either charged, or carry side-chains able to form hydrogen bonds, were required to be inserted into the model, the potential to form favourable interactions was also considered.

All possible overlapping 13 amino-acid peptides from the humanised A33 antibody variable region protein sequences were examined. Each peptide sequence was used to form a three-dimensional model of the candidate peptide in complex with the given MHC allele. Peptide model structures were built assuming a backbone conformation and location relative to the MHC backbone structure identical to that of the previously solved structure for HLA-DRB1 in complex with an influenza haemagglutinin protein (Stem L. J. et al., ibid.). This assumption is supported by available evidence (Jardetzky T. S. et al., *Nature* 368 711–718 (1994); Ghosh P. et al., ibid.). Side-chains in the peptide were modelled automatically to match the sequence of the peptide under investigation, and the conformational space of each side chain was explored automatically to minimise or eliminate steric overlap and unfavourable atomic contacts, whilst also maximising favourable atomic contacts.

A score for each peptide was computed based upon the predicted inter-atomic contacts between peptide and MHC residues. Pair-wise residue-residue interaction scores were used to reward and penalise specific inter-residue contacts. The geometric constraints imposed on the peptide by the shape of the MHC binding groove play an important part of the scoring function. To reflect this, the scoring function awards favourable packing arrangements, whilst interactions involving steric overlap are penalised. Published data (Ghosh P. et al., ibid.; Stern L. J. et al., ibid.; Marshall K. W. et al., *J. Immunol.* 152 4946–4957 (1994); Hammer J. et al., *Cell* 74 197–203 (199); Sinigaglia F. & Hammer J. *Current Opin. Immunol.* 6 52–56 (1994)] indicate that larger pockets within the MHC class II binding groove are more important in determining which peptides can bind compared with smaller pockets., The scores contributed by each pocket are also weighted based on pocket size. Peptides with the highest scores are predicted to be the best binders to the particular MHC allele.

Results from this approach are given by way of examples in Tables 1–4. These tables show output from the peptide threading process for heavy and light chains against HLA-DRB1*0101 and HLA-DRB1*03011 alleles only, although threading was performed using structural models compiled for a total of 11 HLA-DRB1 alleles. Following subtraction of sequence strings in the variable regions which are present in a database of human germline immunoglobulin variable region genes, four regions containing potential MHC class II binding motifs in the heavy and light chain humanised A33 variable regions are identified. This result is concordant with comparative searching of an MHC-binding motif database as resident on the world wide web site wehi1.wehi.edu.au.

The potential MHC class II binding motifs identified by the use of peptide threading and corroborated with MHC-binding motif database searching were eliminated from the humanised A33 variable region protein sequences by amino-acid substitutions at specific residues (FIGS. 24 and 25). For the heavy chain substitution of L for I (amino acid single letter codes) at position 89, T for S at position 87, F for Y at position 91 and T for A at position 28 results in elimination of all but one of the potential epitopes. A single heavy chain epitope remains within CDRH3 as alteration may be prejudicial to the antigen binding function of A33. The method of the present invention allows for substitutions to proceed empirically. For the light chain one potential binding motif falls entirely within CDRL1, remaining potential epitopes are eliminated by substitution of F for I at position 83, S for T at position 46, G for Q at position 105 and Y for F at position 87.

TABLE 1

Peptides from humanised A33 light chain variable region predicted by peptide threading to have the strongest binding interaction with HLA-DRB1*0101. Shaded cells indicate peptides not present in a database of human germline immunoglobulin variable regions and hence peptides with greatest immunogenic potential in HLA-DRB1*0101 individuals.

| Rank | Sequence Position | Peptide Sequence | Score | SEQ ID NO: |
|---|---|---|---|---|
| 1 | 73 | FTISSLQPEDIAT | 2906947 | SEQ ID NO: 3 |
| 2 | 37 | QQKPGLAPKILTY | 2869068 | SEQ ID NO: 4 |
| 3 | 56 | TGVPSRFSGSGSG | 2227314 | SEQ ID NO: 5 |
| 4 | 9 | SSLSVSVGDRVTI | 2151680 | SEQ ID NO: 6 |
| 5 | 76 | SSLQPEDIATYFC | 1981125 | SEQ ID NO: 7 |
| 6 | 11 | LSVSVGDRVTITC | 1851329 | SEQ ID NO: 8 |
| 7 | 91 | HWSYPLTFGQGTK | 1799889 | SEQ ID NO: 9 |
| 8 | 96 | LTFGQGTKVEVKR | 1789663 | SEQ ID NO: 10 |
| 9 | 60 | SRFSGSGSGTDFT | 1781975 | SEQ ID NO: 11 |
| 10 | 45 | KTLIYLASNRHTG | 1665759 | SEQ ID NO: 12 |
| 11 | 34 | AWYQQKPGLAPKT | 1579725 | SEQ ID NO: 13 |
| 12 | 3 | QMTQSPSSLSVSV | 1548170 | SEQ ID NO: 14 |
| 13 | 1 | DIQMTQSPSSLSV | 1523983 | SEQ ID NO: 15 |
| 14 | 27 | QNVRTVVAWYQQK | 1479591 | SEQ ID NO: 16 |
| 15 | 18 | RVTITCKASQNVR | 1404588 | SEQ ID NO: 17 |
| 16 | 33 | VAWYQQKLPGLAPK | 1384902 | SEQ ID NO: 18 |
| 17 | 17 | DRVTITCKASQNV | 1196170 | SEQ ID NO: 19 |
| 18 | 6 | QSPSSLSVSVGDR | 1134256 | SEQ ID NO: 20 |
| 19 | 24 | KASQNVRTVVAWY | 1100038 | SEQ ID NO: 21 |
| 20 | 90 | QHWSYPLTFGQGT | 1045861 | SEQ ID NO: 22 |

TABLE 2

Peptides from humanised A33 light chain variable region predicted by peptide threading to have the strongest binding interaction with HLA-DRB1*03011. Shaded cells indicate peptides not present in a database of human germline immunoglobulin variable regions and hence peptides with greatest immunogenic potential in HLA-DRB1*03011 individuals.

| Rank | Sequence Position | Peptide Sequence | Score | SEQ ID NO: |
|---|---|---|---|---|
| 1 | 27 | QNVRTVVAQYQQK | 4679664 | SEQ ID NO: 23 |
| 2 | 37 | QQKPGLAPKTLLY | 2614050 | SEQ ID NO: 24 |
| 3 | 81 | EDIATYFCQQHWS | 2538553 | SEQ ID NO: 25 |
| 4 | 45 | KTLIYLASNRHTG | 2214414 | SEQ ID NO: 26 |
| 5 | 56 | TGVPSRFSGSGSG | 2152389 | SEQ ID NO: 27 |
| 6 | 17 | DRVTITCKASQNV | 2108642 | SEQ ID NO: 28 |
| 7 | 73 | FTISSEQPEDIAT | 2105806 | SEQ ID NO: 29 |
| 8 | 60 | SRFSGSGSGTDFT | 2097225 | SEQ ID NO: 30 |
| 9 | 54 | RHTGVPSRFSGSG | 2067916 | SEQ ID NO: 31 |
| 10 | 96 | LTFGQGTKVEVKR | 2039455 | SEQ ID NO: 32 |
| 11 | 9 | SSLSVSVGDRVTI | 2020864 | SEQ ID NO: 33 |
| 12 | 8 | PSSLSVSVGDRVT | 1994849 | SEQ ID NO: 34 |
| 13 | 24 | KASQNVRTVVAWY | 1946688 | SEQ ID NO: 35 |
| 14 | 76 | SSLQPEDIARYFC | 1901925 | SEQ ID NO: 36 |
| 15 | 11 | LSVSVGDRVTITC | 1812157 | SEQ ID NO: 37 |
| 16 | 31 | TVVAWYQQKPGLA | 1797465 | SEQ ID NO: 38 |
| 17 | 1 | DIQMTQSPSSLSV | 1638069 | SEQ ID NO: 39 |
| 18 | 6 | QSPSSLSVSVGDR | 1608168 | SEQ ID NO: 40 |
| 19 | 18 | RVTITCKASQNVR | 1322137 | SEQ ID NO: 41 |
| 20 | 51 | ASNRHTGVPSRFS | 1291927 | SEQ ID NO: 42 |

TABLE 3

Peptides from humanised A33 heavy chain variable region predicted by peptide threading to have the strongest binding interaction with HLA-DRB1*0101. Shaded cells indicate peptides not present in a database of human germline immunoglobulin variable regions and hence peptides with greatest immunogenic potential in HLA-DRB1*0101 individuals.

| Rank | Sequence Position | Peptide Sequence | Score | SEQ ID NO: |
|---|---|---|---|---|
| 1 | 78 | TLYLQMNSLQAED | 5662707 | SEQ ID NO: 43 |
| 2 | 3 | QLLESGGGLVQPG | 4552719 | SEQ ID NO: 44 |
| 3 | 35 | SWVRQAPGKGLEW | 3948115 | SEQ ID NO: 45 |
| 4 | 76 | KNTLYLQMNSLQA | 3782821 | SEQ ID NO: 46 |
| 5 | 16 | GSLRLSCAASGFA | 3367975 | SEQ ID NO: 47 |
| 6 | 18 | LRLSCAASGFAFS | 3146731 | SEQ ID NO: 48 |
| 7 | 81 | LQMNSLQAEDSAI | 2880801 | SEQ ID NO: 49 |
| 8 | 71 | SRDSSKNTLYLQM | 2669460 | SEQ ID NO: 50 |
| 9 | 56 | SYTYYLDSVKGRF | 2543939 | SEQ ID NO: 51 |
| 10 | 10 | GLVQPGGSLRLSC | 2520655 | SEQ ID NO: 52 |
| 11 | 84 | NSLQAEDSAIYYG | 2412032 | SEQ ID NO: 53 |
| 12 | 13 | QPGGSLRLSCAAS | 1852553 | SEQ ID NO: 54 |
| 13 | 1 | EVQLLESGGGLVQ | 1831863 | SEQ ID NO: 55 |
| 14 | 6 | ESGGGLVQPGGSL | 1789461 | SEQ ID NO: 56 |
| 15 | 30 | STYDMSWVRQAPG | 1690753 | SEQ ID NO: 57 |
| 16 | 34 | MSWVRQAPGKGLE | 1669184 | SEQ ID NO: 58 |
| 17 | 9 | GGLVQPGGSLRLS | 1635030 | SEQ ID NO: 59 |
| 18 | 46 | EWVATISSGGSYT | 1591661 | SEQ ID NO: 60 |
| 19 | 100 | TVVPFAYWGQGTL | 1587576 | SEQ ID NO: 61 |
| 20 | 62 | DSVKGRFTISRDS | 1521740 | SEQ ID NO: 62 |

TABLE 4

Peptides from humanised A33 heavy chain variable region predicted by peptide threading to have the strongest binding interaction with HLA-DRB1*0311. Shaded cells indicate peptides not present in a database of human germline immunoglobulin variable regions and hence peptides with greatest immunogenic potential in HLA-DRB1*03011 individuals.

| Rank | Sequence Position | Peptide Sequence | Score | SEQ ID NO: |
|---|---|---|---|---|
| 1 | 35 | SWVRQAPGKGLEW | 4151567 | SEQ ID NO: 63 |

TABLE 4-continued

Peptides from humanised A33 heavy chain variable region predicted by peptide threading to have the strongest binding interaction with HLA-DRB1*0311. Shaded cells indicate peptides not present in a database of human germline immunoglobulin variable regions and hence peptides with greatest immunogenic potential in HLA-DRB1*03011 individuals.

| Rank | Sequence Position | Peptide Sequence | Score | SEQ ID NO: |
|---|---|---|---|---|
| 2 | 3 | QLLESGGGLVQPG | 3673867 | SEQ ID NO: 64 |
| 3 | 16 | GSLRLSGAASGFA | 3244475 | SEQ ID NO: 65 |
| 4 | 18 | LRLSCAASGFAFS | 3110036 | SEQ ID NO: 66 |
| 5 | 76 | KNTLYLQMNSLQA | 2937467 | SEQ ID NO: 67 |
| 6 | 46 | EWVATISSGGSYT | 2770382 | SEQ ID NO: 68 |
| 7 | 84 | NSLQAEDSAIYYC | 2282240 | SEQ ID NO: 69 |
| 8 | 10 | GLVQPGGSLRLSC | 2158781 | SEQ ID NO: 70 |
| 9 | 71 | SRDSSKNTLYLQM | 2151419 | SEQ ID NO: 71 |
| 10 | 102 | VPFAYWGQGTLVT | 2015801 | SEQ ID NO: 72 |
| 11 | 43 | KGLEWVATISSGG | 2001944 | SEQ ID NO: 73 |
| 12 | 81 | LQMNSLQAEDSAI | 1971734 | SEQ ID NO: 74 |
| 13 | 99 | TTVVPFAYWGQGT | 1825539 | SEQ ID NO: 75 |
| 14 | 1 | EVQLLESGGGLVQ | 1824590 | SEQ ID NO: 76 |
| 15 | 56 | SYTYYLDSVKGRF | 1698015 | SEQ ID NO: 77 |
| 16 | 59 | YYLDSVKGRFTIS | 1684498 | SEQ ID NO: 78 |
| 17 | 9 | GGLVQPGGSLRLS | 1618110 | SEQ ID NO: 79 |
| 18 | 62 | DSVKGRFRTISRDS | 1601551 | SEQ ID NO: 80 |
| 19 | 100 | TVVPFAYWGQGTL | 1598301 | SEQ ID NO: 81 |
| 20 | 32 | YDMSWVRQAPGKG | 1593906 | SEQ ID NO: 82 |

EXAMPLE 6

In this example the method of the present invention is used to identify and eliminate potential epitopes from the murine sequence of antibody A33 (King D. J. et al., *Brit. J. Cancer* 72 1364–1372 (1995)). The humanised version of A33 was described in example 5, in the present example the starting point is the murine A33 antibody. The sequences of the $V_H$ and $V_L$ of the murine A33 antibody are shown in FIG. 26. A de-immunised antibody was generated by analysis of these sequences. To remove B cell epitopes, the "veneering" method of Padlan (Padlan E. A., 1991, ibid and EP-A-0519596) was applied whereby exposed (mE or mEx) residues in the murine A33 $V_H$ or $V_L$ sequences were substituted by the corresponding residues in the frameworks from the human germ-line sequences DP-3 for $V_H$ (Tomlinson et al., 1992, ibid) with human $J_H1$ and LFVK431 (Cox et al.1994, ibid) for $V_L$ with human $J_K4$ Then, the resultant sequences were analysed by searching a database of human MBC Class II binding peptides ("motif" at the World-Wide Web site wehil.wehi.edu.ac) for motifs present in the veneered $V_H$ and $V_L$ sequences. In parallel, databases of human $V_H$ and $V_L$ germ-line sequences (Tomlinson et al., ibid; Cox et al. ibid; other germ-line sequences retrieved from EMBL, GenBank and Swiss Protein databases) were also searched for human MHC Class II binding motifs. Motifs appearing in the veneered antibody sequence which were also present in the germ-line were not considered further. For motifs present in the veneered $V_H$ and $V_L$ sequences and not present in the germ-line database, single amino acid substitutions were made in order to delete the motifs, using residues found at this position in human germ-line antibody sequences, unless a substitution was required within a CDR. Following this round of motif deletion, the resultant sequences were checked for generation of new MHC Class II motifs which were similarly deleted if present. The resultant de-immunised $V_H$ and $V_L$ sequences are shown in FIG. 27. The de-immunised $V_H$ and $V_L$ sequences were constructed as described for the 340 antibody (Example 1) using long synthetic oligonucleotides. Cloning, sequencing, addition of human C regions and expression in NS0 cells was as for the 340 antibody (Example 1).

EXAMPLE 7

The present invention details a process whereby potentially immunogenic epitopes within a non-autologous protein may be identified and offers methodology whereby such epitopes may be eliminated. There are a number of proven therapeutic proteins for which their therapeutic use is curtailed on account of their immunogenicity in man. In the present example the therapeutic protein streptokinase is analysed for the presence of potential MHC binding motifs and a method disclosed for the removal of a number of these from the molecule.

Streptokinase (SK) is a single chain protein of approximate molecular weight 47 kDa that is produced by certain strains of β-haemolytic streptococci (Huang T. T. et al., *Mol. Biol.* 2 197–205 (1989)). The protein has no inherent enzymatic activity but has considerable clinical importance owing to its ability to efficiently bind human plasminogen, potentiating its activation to plasmin and thereby promoting the dissolution of fibrin filaments in blood clots. Several studies have shown that SK is an effective thrombolytic agent in the treatment of coronary thrombosis, improving survival (ISIS-2 Collaborative Group, *Lancet* 2 349–360 (1988)) and preserving left ventricular function following myocardial infarction [ISAM Study Group, *N. Engl. J. Med.* 314 1465–1471 (1986); Kennedy J. W. et al., *Circulation* 77 345–352 (1988)). Despite the undoubted therapeutic value of SK, the non-autologous origin of the protein is disadvantageous due to its immunogenicity in humans. The production of neutralising antibodies in the patient in generally limits the protein to a single use.

The following method was used to identify potential MHC class II binding motifs in streptokinase. The sequence of streptolinase was identified from the GenBank database. The sequence with accession number S46536 was used throughout (FIG. 28). The sequence was analysed for the presence of potential MHC class II binding motifs by computer aided comparison to a database of MHC-binding motifs as resident on world wide web site wehil-.wehi.edu.au.

Results of the "searching" process indicate the presence of 395 potential MHC class II binding motifs. Of these, 283 matched sequences identified in a database of human germline immunoglobulin variable region protein sequences. These epitopes were not considered further on the basis that immune responses in general are not mounted to autologous circulating proteins such as immunoglobulins. This implies immunological tolerance to the potential T-cell epitopes present in the structure of the immunoglobulins (and indeed the majority of human proteins). Epitopes presented by non-autologous proteins such as SK which are identical or similar to motifs present in immunoglobulin proteins are likely also to be tolerated and in practice may be retained through the de-immunisation process.

Following subtraction of the human immunoglobulin protein germline motifs, the remaining 112 potential epitopes were analysed individually for similarity to non-immunoglobulin protein sequences. In practice, predicted anchor residues for each potential epitope was used in a consensus sequence search of human expressed proteins. The SwissProt and GenBank translated sequence databases were interrogated using commercially available software (DNAstar Madison, Wis., USA), Epitopes identified in known circulating human proteins were not considered further and were therefore allowed to remain unchanged within the SK molecule. An example of one such rejected potential epitope is given by the sequence LLKAIQEQL (SEQ ID NO: 83) at positions 79–87 in the SK protein.

This sequence represents a predicted consensus binding motif for HLA-DR1*0101 with anchor residues underlined. Database searching using the consensus sequence LxxxAxxxxL identifies >4000 entries in a human protein sub-set of the SwissProt database, including serum albumin protein (SwissProt accession number P02768), An example of an epitope where no match to a human protein considered to be in the general circulation was found is provided by sequence YVDVNTN (SEQ ID NO: 84) at position 299–305 in the SK protein. This sequence represents a potential epitope for presentation by HLA-DR4*0401. Consensus sequence searching identifies <50 human proteins containing this motif, of which many are intracellular proteins of differentiated tissues such as brain. These may be considered as not generally available to the immune system to gain tolerance and therefore identify this as a potential epitope for elimination according to the method of the present invention. Similarly, a further potential HLA-DRI*0101 binding motif was identified in the SK peptide sequence KADLLKAI (SEQ ID NO: 85) at positions 76–83 of the SK protein. This motif identifies <150 human proteins in the same data set and was also identified for modification by the method of the present invention.

The net result of these processes was to identify those residues within the SK molecule which should be altered to eliminate potential MHC class II binding motifs. Individual amino acids within the predicted binding motifs were selected for alteration. With the object of maximising the likelihood of maintaining protein functional activity, in all cases conservative amino acid substitutions were chosen at any given site. A new (de-immunised) SK sequence was compiled (FIG. 29) and further analysed by database comparison, as previously, for confirmation of successful elimination of potential MHC class II binding motifs.

The following method was used for the construction of de-immunised SK molecules. PCR primers SKI (5'-ggaat-tcatgattgctggacctgagtggctg) (SEQ ID NO: 86) and SK2 (5'-tggatccttatttgtcgttagggtatc) (SEQ ID NO: 87) were used to amplify the wild-type SK gene from a strain of *Streptococcus equisimililis* group C (ATCC accession number 9542), The resulting 1233bp fragment was cloned into pUC19 as a BamHI-EcoRI restriction fragment using standard techniques (Sambrook J., Fritisch E. F. & Maniatis T. (eds.) in: *"Molecular Cloning: A Laboratory Manual,"* Cold Spring Harbor Laboratory Press, NY, USA (1989). The gene sequence was confirmed to be identical to database entries using commercially available reagent systems and instructions provided by the supplier (Amersham, Little Chalfont, UK), Site directed Mutagenesis was conducted using synthetic oligonucleotides and the "quick-change" procedure and reagents from Stratagene UK Ltd. Mutated (de-immunised) versions of the gene were confirmed by sequencing. Mutated SK genes were sub-cloned as EcoRI-BamHI fragments into the bacterial expression vector pEKG-3 (Estrada M. P., et al., *Bio/Technology* 10: 1138–1142 (1992)) for expression of de-immunised 5K. Recombinant protein was purified using a plasminogen affinity column according to the method of Rodriguez, et a)., *Biotechniques* 7: 638–641 (1992)), Fibrinolytic activity was assessed using the casein/plasminogen plate technique and the in vitro clot lysis assay as described by Estrada, et al., (Estrada, et al., ibid.),

The invention claimed is:

1. A method of rendering streptokinase non-immunogenic or less immunogenic when exposed to the immune system of a human, the method comprising the steps of:

(a) identifying a first set of potential T-cell epitope sequences within the amino acid residue sequence of streptokinase (SEQ ID NO: 252) by (i) analysing said amino acid sequence for the presence of MHC class II binding motifs, and (ii) comparing the MHC class II binding motifs in the streptokinase amino acid residue sequence with human MHC binding motifs available from an MHC database;

(b) comparing the first set of potential T-cell epitope sequences identified in step (a) with human immunoglobulin variable region germ line amino acid residue sequences available from a human germ-line sequence database to identify a subset of potential T-cell epitopes within the streptokinase amino acid residue sequence that are not present in human immunoglobulin variable region germ-line sequences; and (c) preparing a de-immunized streptokinase polypeptide having the amino acid residue sequence of SEQ ID NO: 252 but including at least one amino acid residue substitution that eliminates from the streptokinase amino acid residue sequence at least one epitope sequence from the subset identified in step (b), wherein the de-immunized streptokinase polypeptide has the amino acid residue sequence of SEQ ID NO: 253.

* * * * *

SEQUENCE LISTING

<160> NUMBER OF SEQ ID NOS: 254

<210> SEQ ID NO 1
<211> LENGTH: 6
<212> TYPE: PRT
<213> ORGANISM: Homo sapiens

<400> SEQUENCE: 1

His Ser Ile Gly Asp Pro
1               5

<210> SEQ ID NO 2
<211> LENGTH: 6
<212> TYPE: PRT
<213> ORGANISM: Homo Sapiens

<400> SEQUENCE: 2

His Ser Ile Gly Lys Val
1               5

<210> SEQ ID NO 3
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 3

```
Phe Thr Ile Ser Ser Leu Gln Pro Glu Asp Ile Ala Thr
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 4

Gln Gln Lys Pro Gly Leu Ala Pro Lys Thr Leu Ile Tyr
 1               5                  10

<210> SEQ ID NO 5
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 5

Thr Gly Val Pro Ser Arg Phe Ser Gly Ser Gly Ser Gly
 1               5                  10

<210> SEQ ID NO 6
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 6

Ser Ser Leu Ser Val Ser Val Gly Asp Arg Val Thr Ile
 1               5                  10

<210> SEQ ID NO 7
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 7

Ser Ser Leu Gln Pro Glu Asp Ile Ala Thr Tyr Phe Cys
 1               5                  10

<210> SEQ ID NO 8
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 8

Leu Ser Val Ser Val Gly Asp Arg Val Thr Ile Thr Cys
 1               5                  10

<210> SEQ ID NO 9
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 9
```

```
His Trp Ser Tyr Pro Leu Thr Phe Gly Gln Gly Thr Lys
 1               5                   10
```

```
<210> SEQ ID NO 10
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 10

Leu Thr Phe Gly Gln Gly Thr Lys Val Glu Val Lys Arg
 1               5                   10
```

```
<210> SEQ ID NO 11
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 11

Ser Arg Phe Ser Gly Ser Gly Ser Gly Thr Asp Phe Thr
 1               5                   10
```

```
<210> SEQ ID NO 12
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 12

Lys Thr Leu Ile Tyr Leu Ala Ser Asn Arg His Thr Gly
 1               5                   10
```

```
<210> SEQ ID NO 13
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 13

Ala Trp Tyr Gln Gln Lys Pro Gly Leu Ala Pro Lys Thr
 1               5                   10
```

```
<210> SEQ ID NO 14
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 14

Gln Met Thr Gln Ser Pro Ser Ser Leu Ser Val Ser Val
 1               5                   10
```

```
<210> SEQ ID NO 15
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 15

Asp Ile Gln Met Thr Gln Ser Pro Ser Ser Leu Ser Val
```

```
<210> SEQ ID NO 16
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 16

Gln Asn Val Arg Thr Val Val Ala Trp Tyr Gln Gln Lys
1               5                   10

<210> SEQ ID NO 17
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 17

Arg Val Thr Ile Thr Cys Lys Ala Ser Gln Asn Val Arg
1               5                   10

<210> SEQ ID NO 18
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 18

Val Ala Trp Tyr Gln Gln Lys Pro Gly Leu Ala Pro Lys
1               5                   10

<210> SEQ ID NO 19
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 19

Asp Arg Val Thr Ile Thr Cys Lys Ala Ser Gln Asn Val
1               5                   10

<210> SEQ ID NO 20
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 20

Gln Ser Pro Ser Ser Leu Ser Val Ser Val Gly Asp Arg
1               5                   10

<210> SEQ ID NO 21
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 21

Lys Ala Ser Gln Asn Val Arg Thr Val Val Ala Trp Tyr
1               5                   10
```

<210> SEQ ID NO 22
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 22

Gln His Trp Ser Tyr Pro Leu Thr Phe Gly Gln Gly Thr
1               5                   10

<210> SEQ ID NO 23
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 23

Gln Asn Val Arg Thr Val Val Ala Trp Tyr Gln Gln Lys
1               5                   10

<210> SEQ ID NO 24
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 24

Gln Gln Lys Pro Gly Leu Ala Pro Lys Thr Leu Ile Tyr
1               5                   10

<210> SEQ ID NO 25
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 25

Glu Asp Ile Ala Thr Tyr Phe Cys Gln Gln His Trp Ser
1               5                   10

<210> SEQ ID NO 26
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 26

Lys Thr Leu Ile Tyr Leu Ala Ser Asn Arg His Thr Gly
1               5                   10

<210> SEQ ID NO 27
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 27

Thr Gly Val Pro Ser Arg Phe Ser Gly Ser Gly Ser Gly
1               5                   10

```
<210> SEQ ID NO 28
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 28

Asp Arg Val Thr Ile Thr Cys Lys Ala Ser Gln Asn Val
1               5                   10

<210> SEQ ID NO 29
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 29

Phe Thr Ile Ser Ser Leu Gln Pro Glu Asp Ile Ala Thr
1               5                   10

<210> SEQ ID NO 30
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 30

Ser Arg Phe Ser Gly Ser Gly Ser Gly Thr Asp Phe Thr
1               5                   10

<210> SEQ ID NO 31
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 31

Arg His Thr Gly Val Pro Ser Arg Phe Ser Gly Ser Gly
1               5                   10

<210> SEQ ID NO 32
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 32

Leu Thr Phe Gly Gln Gly Thr Lys Val Glu Val Lys Arg
1               5                   10

<210> SEQ ID NO 33
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 33

Ser Ser Leu Ser Val Ser Val Gly Asp Arg Val Thr Ile
1               5                   10
```

```
<210> SEQ ID NO 34
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 34

Pro Ser Ser Leu Ser Val Ser Val Gly Asp Arg Val Thr
 1               5                  10

<210> SEQ ID NO 35
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 35

Lys Ala Ser Gln Asn Val Arg Thr Val Val Ala Trp Tyr
 1               5                  10

<210> SEQ ID NO 36
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 36

Ser Ser Leu Gln Pro Glu Asp Ile Ala Arg Tyr Phe Cys
 1               5                  10

<210> SEQ ID NO 37
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 37

Leu Ser Val Ser Val Gly Asp Arg Val Thr Ile Thr Cys
 1               5                  10

<210> SEQ ID NO 38
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 38

Thr Val Val Ala Trp Tyr Gln Gln Lys Pro Gly Leu Ala
 1               5                  10

<210> SEQ ID NO 39
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 39

Asp Ile Gln Met Thr Gln Ser Pro Ser Ser Leu Ser Val
 1               5                  10

<210> SEQ ID NO 40
```

```
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 40

Gln Ser Pro Ser Ser Leu Ser Val Ser Val Gly Asp Arg
 1               5                  10

<210> SEQ ID NO 41
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 41

Arg Val Thr Ile Thr Cys Lys Ala Ser Gln Asn Val Arg
 1               5                  10

<210> SEQ ID NO 42
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 42

Ala Ser Asn Arg His Thr Gly Val Pro Ser Arg Phe Ser
 1               5                  10

<210> SEQ ID NO 43
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 43

Thr Leu Tyr Leu Gln Met Asn Ser Leu Gln Ala Glu Asp
 1               5                  10

<210> SEQ ID NO 44
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 44

Gln Leu Leu Glu Ser Gly Gly Gly Leu Val Gln Pro Gly
 1               5                  10

<210> SEQ ID NO 45
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 45

Ser Trp Val Arg Gln Ala Pro Gly Lys Gly Leu Glu Trp
 1               5                  10

<210> SEQ ID NO 46
<211> LENGTH: 13
```

```
<212> TYPE: PRT
<213> ORGANISM: Artificial Sequence
<220> FEATURE:
<223> OTHER INFORMATION: humanized monoclonal antibody fragments

<400> SEQUENCE: 46

Lys Asn Thr Leu Tyr Leu Gln Met Asn Ser Leu Gln Ala
 1               5                  10

<210> SEQ ID NO 47
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 47

Gly Ser Leu Arg Leu Ser Cys Ala Ala Ser Gly Phe Ala
 1               5                  10

<210> SEQ ID NO 48
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 48

Leu Arg Leu Ser Cys Ala Ala Ser Gly Phe Ala Phe Ser
 1               5                  10

<210> SEQ ID NO 49
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 49

Leu Gln Met Asn Ser Leu Gln Ala Glu Asp Ser Ala Ile
 1               5                  10

<210> SEQ ID NO 50
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 50

Ser Arg Asp Ser Ser Lys Asn Thr Leu Tyr Leu Gln Met
 1               5                  10

<210> SEQ ID NO 51
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 51

Ser Tyr Thr Tyr Tyr Leu Asp Ser Val Lys Gly Arg Phe
 1               5                  10

<210> SEQ ID NO 52
<211> LENGTH: 13
<212> TYPE: PRT
```

```
<213> ORGANISM: Artificial Sequence
<220> FEATURE:
<223> OTHER INFORMATION: humanized monoclonal antibody fragments

<400> SEQUENCE: 52

Gly Leu Val Gln Pro Gly Gly Ser Leu Arg Leu Ser Cys
 1               5                  10

<210> SEQ ID NO 53
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 53

Asn Ser Leu Gln Ala Glu Asp Ser Ala Ile Tyr Tyr Cys
 1               5                  10

<210> SEQ ID NO 54
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 54

Gln Pro Gly Gly Ser Leu Arg Leu Ser Cys Ala Ala Ser
 1               5                  10

<210> SEQ ID NO 55
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 55

Glu Val Gln Leu Leu Glu Ser Gly Gly Gly Leu Val Gln
 1               5                  10

<210> SEQ ID NO 56
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 56

Glu Ser Gly Gly Gly Leu Val Gln Pro Gly Gly Ser Leu
 1               5                  10

<210> SEQ ID NO 57
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 57

Ser Thr Tyr Asp Met Ser Trp Val Arg Gln Ala Pro Gly
 1               5                  10

<210> SEQ ID NO 58
<211> LENGTH: 13
<212> TYPE: PRT
<213> ORGANISM: Artificial Sequence
```

-continued

```
<220> FEATURE:
<223> OTHER INFORMATION: humanized monoclonal antibody fragments

<400> SEQUENCE: 58

Met Ser Trp Val Arg Gln Ala Pro Gly Lys Gly Leu Glu
1               5                   10

<210> SEQ ID NO 59
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 59

Gly Gly Leu Val Gln Pro Gly Gly Ser Leu Arg Leu Ser
1               5                   10

<210> SEQ ID NO 60
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 60

Glu Trp Val Ala Thr Ile Ser Ser Gly Gly Ser Tyr Thr
1               5                   10

<210> SEQ ID NO 61
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 61

Thr Val Val Pro Phe Ala Tyr Trp Gly Gln Gly Thr Leu
1               5                   10

<210> SEQ ID NO 62
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 62

Asp Ser Val Lys Gly Arg Phe Thr Ile Ser Arg Asp Ser
1               5                   10

<210> SEQ ID NO 63
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 63

Ser Trp Val Arg Gln Ala Pro Gly Lys Gly Leu Glu Trp
1               5                   10

<210> SEQ ID NO 64
<211> LENGTH: 13
<212> TYPE: PRT
<213> ORGANISM: Artificial Sequence
<220> FEATURE:
```

<223> OTHER INFORMATION: humanized monoclonal antibody fragments

<400> SEQUENCE: 64

Gln Leu Leu Glu Ser Gly Gly Gly Leu Val Gln Pro Gly
1               5                   10

<210> SEQ ID NO 65
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 65

Gly Ser Leu Arg Leu Ser Cys Ala Ala Ser Gly Phe Ala
1               5                   10

<210> SEQ ID NO 66
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 66

Leu Arg Leu Ser Cys Ala Ala Ser Gly Phe Ala Phe Ser
1               5                   10

<210> SEQ ID NO 67
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 67

Lys Asn Thr Leu Tyr Leu Gln Met Asn Ser Leu Gln Ala
1               5                   10

<210> SEQ ID NO 68
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 68

Glu Trp Val Ala Thr Ile Ser Ser Gly Gly Ser Tyr Thr
1               5                   10

<210> SEQ ID NO 69
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 69

Asn Ser Leu Gln Ala Glu Asp Ser Ala Ile Tyr Tyr Cys
1               5                   10

<210> SEQ ID NO 70
<211> LENGTH: 13
<212> TYPE: PRT
<213> ORGANISM: Artificial Sequence
<220> FEATURE:
<223> OTHER INFORMATION: humanized monoclonal antibody fragments -continued

<400> SEQUENCE: 70

Gly Leu Val Gln Pro Gly Gly Ser Leu Arg Leu Ser Cys
1               5                   10

<210> SEQ ID NO 71
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 71

Ser Arg Asp Ser Ser Lys Asn Thr Leu Tyr Leu Gln Met
1               5                   10

<210> SEQ ID NO 72
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 72

Val Pro Phe Ala Tyr Trp Gly Gln Gly Thr Leu Val Thr
1               5                   10

<210> SEQ ID NO 73
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 73

Lys Gly Leu Glu Trp Val Ala Thr Ile Ser Ser Gly Gly
1               5                   10

<210> SEQ ID NO 74
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 74

Leu Gln Met Asn Ser Leu Gln Ala Glu Asp Ser Ala Ile
1               5                   10

<210> SEQ ID NO 75
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 75

Thr Thr Val Val Pro Phe Ala Tyr Trp Gly Gln Gly Thr
1               5                   10

<210> SEQ ID NO 76
<211> LENGTH: 13
<212> TYPE: PRT
<213> ORGANISM: Artificial Sequence
<220> FEATURE:
<223> OTHER INFORMATION: humanized monoclonal antibody fragments

```
<400> SEQUENCE: 76

Glu Val Gln Leu Leu Glu Ser Gly Gly Gly Leu Val Gln
 1               5                   10

<210> SEQ ID NO 77
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 77

Ser Tyr Thr Tyr Tyr Leu Asp Ser Val Lys Gly Arg Phe
 1               5                   10

<210> SEQ ID NO 78
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 78

Tyr Tyr Leu Asp Ser Val Lys Gly Arg Phe Thr Ile Ser
 1               5                   10

<210> SEQ ID NO 79
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 79

Gly Gly Leu Val Gln Pro Gly Gly Ser Leu Arg Leu Ser
 1               5                   10

<210> SEQ ID NO 80
<211> LENGTH: 14
<212> TYPE: PRT
<213> ORGANISM: Artificial Sequence
<220> FEATURE:
<223> OTHER INFORMATION: humanized monoclonal antibody fragments

<400> SEQUENCE: 80

Asp Ser Val Lys Gly Arg Phe Arg Thr Ile Ser Arg Asp Ser
 1               5                   10

<210> SEQ ID NO 81
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 81

Thr Val Val Pro Phe Ala Tyr Trp Gly Gln Gly Thr Leu
 1               5                   10

<210> SEQ ID NO 82
<211> LENGTH: 13
<212> TYPE: PRT
<213> ORGANISM: Artificial Sequence
<220> FEATURE:
<223> OTHER INFORMATION: humanized monoclonal antibody fragments

<400> SEQUENCE: 82
```

-continued

Tyr Asp Met Ser Trp Val Arg Gln Ala Pro Gly Lys Gly
 1               5                   10

<210> SEQ ID NO 83
<211> LENGTH: 9
<212> TYPE: PRT
<213> ORGANISM: Artificial Sequence
<220> FEATURE:
<223> OTHER INFORMATION: streptococcus equisimilis

<400> SEQUENCE: 83

Leu Leu Lys Ala Ile Gln Glu Gln Leu
 1               5

<210> SEQ ID NO 84
<211> LENGTH: 7
<212> TYPE: PRT
<213> ORGANISM: Artificial Sequence
<220> FEATURE:
<223> OTHER INFORMATION: streptococcus equisimilis

<400> SEQUENCE: 84

Tyr Val Asp Val Asn Thr Asn
 1               5

<210> SEQ ID NO 85
<211> LENGTH: 8
<212> TYPE: PRT
<213> ORGANISM: Artificial Sequence
<220> FEATURE:
<223> OTHER INFORMATION: streptococcus equisimilis

<400> SEQUENCE: 85

Lys Ala Asp Leu Leu Lys Ala Ile
 1               5

<210> SEQ ID NO 86
<211> LENGTH: 31
<212> TYPE: DNA
<213> ORGANISM: Artificial Sequence
<220> FEATURE:
<223> OTHER INFORMATION: PCR Primer

<400> SEQUENCE: 86
ggaattcatg attgctggac ctgagtggct g                              31

<210> SEQ ID NO 87
<211> LENGTH: 27
<212> TYPE: DNA
<213> ORGANISM: Artificial Sequence
<220> FEATURE:
<223> OTHER INFORMATION: PCR Primer

<400> SEQUENCE: 87
tggatcctta tttgtcgtta gggtatc                                   27

<210> SEQ ID NO 88
<211> LENGTH: 363
<212> TYPE: DNA
<213> ORGANISM: Artificial Sequence
<220> FEATURE:
<223> OTHER INFORMATION: humanized hybridoma VH

<400> SEQUENCE: 88
gaagtgcagc tggtggagtc tgggggaggc ttagtgaagg ctggagggtc cctgaaactc    60

```
tcctgtgcag cctctggatt cgctttcgat acctatgaca tgtcttgggt tcgccagact    120
ccggagaaga ggctggagtg ggtcgcatac attggtagtg gtggtgatag aacctactat    180
ccagacactg tgaagggccg attcaccatt tccagagaca tggcaagaa cacctgtat     240 ttgcaattga acagtctgaa gtctgaggac acagccatgt attactgtgc aagacattat    300
ggtcactacg tggactatgc tgtggactac tggggtcaag gaacctcagt caccgtctcc    360
tca                                                                   363
```

<210> SEQ ID NO 89
<211> LENGTH: 329
<212> TYPE: DNA
<213> ORGANISM: Artificial Sequence
<220> FEATURE:
<223> OTHER INFORMATION: humanized hybridoma VH
<400> SEQUENCE: 89

```
acattgtgct gacacagtct cctgcttcct tagctgtatc tctggggcag agggccacca     60
tctcatacag ggccagcaaa agtgtcagta catctggcta tagttatatg cactggaacc    120
aacagaaacc aggacagcca cccagactcc tcatctatct tgtatccaac ctagaatctg    180 ggtccctgc caggttcagt ggcagtgggt ctgggacaga gttcaccctc aacatccatc    240
ctgtggagga ggaggatgct gcaacctatt actgtcagca cattagggag cttatcacgt    300 tcggagggg gaccaagctg gaaataaaa                                        329
```

<210> SEQ ID NO 90
<211> LENGTH: 121
<212> TYPE: PRT
<213> ORGANISM: Musmusculus
<400> SEQUENCE: 90

```
Glu Val Gln Leu Val Glu Ser Gly Gly Gly Leu Val Lys Ala Gly Gly
  1               5                  10                  15

Ser Leu Lys Leu Ser Cys Ala Ala Ser Gly Phe Ala Phe Asp Thr Tyr
             20                  25                  30

Asp Met Ser Trp Val Arg Gln Thr Pro Glu Lys Arg Leu Glu Trp Val
         35                  40                  45

Ala Tyr Ile Gly Ser Gly Gly Asp Arg Thr Tyr Tyr Pro Asp Thr Val
     50                  55                  60

Lys Gly Arg Phe Thr Ile Ser Arg Asp Asn Gly Lys Asn Thr Leu Tyr
 65                  70                  75                  80

Leu Gln Leu Asn Ser Leu Lys Ser Glu Asp Thr Ala Met Tyr Tyr Cys
             85                  90                  95

Ala Arg His Tyr Gly His Tyr Val Asp Tyr Ala Val Asp Tyr Trp Gly
            100                 105                 110

Gln Gly Thr Ser Val Thr Val Ser Ser
        115                 120
```

<210> SEQ ID NO 91
<211> LENGTH: 110
<212> TYPE: PRT
<213> ORGANISM: Musmusculus
<400> SEQUENCE: 91

```
Asp Ile Val Leu Thr Gln Ser Pro Ala Ser Leu Ala Val Ser Leu Gly
  1               5                  10                  15

Gln Arg Ala Thr Ile Ser Tyr Arg Ala Ser Lys Ser Val Ser Thr Ser
             20                  25                  30
```

```
Gly Tyr Ser Tyr Met His Trp Asn Gln Gln Lys Pro Gly Gln Pro
            35                  40                  45

Arg Leu Leu Ile Tyr Leu Val Ser Asn Leu Glu Ser Gly Val Pro Ala
     50                  55                  60

Arg Phe Ser Gly Ser Gly Ser Gly Thr Glu Phe Thr Leu Asn Ile His
 65                  70                  75                  80

Pro Val Glu Glu Asp Ala Ala Thr Tyr Tyr Cys Gln His Ile Arg
                 85                  90                  95

Glu Leu Ile Thr Phe Gly Gly Gly Thr Lys Leu Glu Ile Lys
                100                 105                 110

<210> SEQ ID NO 92
<211> LENGTH: 121
<212> TYPE: PRT
<213> ORGANISM: Artificial Sequence
<220> FEATURE:
<223> OTHER INFORMATION: Humanized murine VH

<400> SEQUENCE: 92

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Asp Thr Tyr
             20                  25                  30

Asp Met Ser Trp Val Arg Gln Ala Pro Gly Lys Gly Leu Glu Trp Val
         35                  40                  45

Ala Tyr Ile Gly Ser Gly Gly Asp Arg Thr Tyr Tyr Pro Asp Thr Val
 50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Val Tyr Tyr Cys
             85                  90                  95

Ala Arg His Tyr Gly His Tyr Val Asp Tyr Ala Val Asp Tyr Trp Gly
            100                 105                 110

Gln Gly Thr Thr Val Thr Val Ser Ser
        115                 120

<210> SEQ ID NO 93
<211> LENGTH: 110
<212> TYPE: PRT
<213> ORGANISM: Artificial Sequence
<220> FEATURE:
<223> OTHER INFORMATION: humanized murine VL

<400> SEQUENCE: 93

Glu Ile Val Leu Thr Gln Ser Pro Ala Thr Leu Ser Leu Ser Pro Gly
 1               5                  10                  15

Glu Arg Ala Thr Leu Ser Tyr Arg Ala Ser Lys Ser Val Ser Thr Ser
             20                  25                  30

Gly Tyr Ser Tyr Met His Trp Asn Gln Gln Lys Pro Gly Gln Ala Pro
         35                  40                  45

Arg Leu Leu Ile Tyr Leu Val Ser Asn Leu Glu Ser Gly Ile Pro Ala
     50                  55                  60

Arg Phe Ser Gly Ser Gly Ser Gly Thr Asp Phe Thr Leu Thr Ile Ser
 65                  70                  75                  80

Ser Leu Glu Pro Glu Asp Phe Ala Val Tyr Tyr Cys Gln His Ile Arg
             85                  90                  95

Glu Leu Ile Thr Phe Gly Gly Gly Thr Lys Val Glu Ile Lys
```

-continued

<210> SEQ ID NO 94
<211> LENGTH: 104
<212> TYPE: DNA
<213> ORGANISM: Artificial Sequence
<220> FEATURE:
<223> OTHER INFORMATION: PCR Primer

<400> SEQUENCE: 94
gacatgtcat aggtatcgaa agcgaatcca gaggctgcac aggagagtct cagggaccct        60
ccaggctgca ctaagcctcc cccagactcc accagctgca cttc                        104

<210> SEQ ID NO 95
<211> LENGTH: 104
<212> TYPE: DNA
<213> ORGANISM: Artificial Sequence
<220> FEATURE:
<223> OTHER INFORMATION: PCR primer

<400> SEQUENCE: 95
cgatacctat gacatgtctt gggttcgcca ggctccgggg aagggctgg agtgggtcgc         60 atacattggt agtggtggtg atagaaccta ctatccagac actg                        104

<210> SEQ ID NO 96
<211> LENGTH: 104
<212> TYPE: DNA
<213> ORGANISM: Artificial Sequence
<220> FEATURE:
<223> OTHER INFORMATION: PCR primer

<400> SEQUENCE: 96
ggctgtgtcc tcagccctca gactgttcat ttgcaaatac agggagttct tggcattgtc       60
tctggaaatg gtgaatcggc ccttcacagt gtctggatag tagg                        104

<210> SEQ ID NO 97
<211> LENGTH: 105
<212> TYPE: DNA
<213> ORGANISM: Artificial Sequence
<220> FEATURE:
<223> OTHER INFORMATION: PCR primer

<400> SEQUENCE: 97
agggctgagg acacagccgt gtattactgt gcaagacatt atggtcacta cgtggactat       60
gctgtggact actggggtca aggaaccaca gtcaccgtct cctca                       105

<210> SEQ ID NO 98
<211> LENGTH: 96
<212> TYPE: DNA
<213> ORGANISM: Artificial Sequence
<220> FEATURE:
<223> OTHER INFORMATION: PCR primer

<400> SEQUENCE: 98
agatgtactg acactttgc tggccctgta tgagagggtg ccctctccc ccggagatag         60 agataaggta gcaggagact gtgtcagcac aatctc                                 96

<210> SEQ ID NO 99
<211> LENGTH: 98
<212> TYPE: DNA
<213> ORGANISM: Artificial Sequence
<220> FEATURE:
<223> OTHER INFORMATION: PCR primer

<400> SEQUENCE: 99
gcaaaagtgt cagtacatct ggctatagtt atatgcactg gaaccaacag aaaccaggac    60
aggcacccag actcctcatc tatcttgtat ccaaccta    98

<210> SEQ ID NO 100
<211> LENGTH: 96
<212> TYPE: DNA
<213> ORGANISM: Artificial Sequence
<220> FEATURE:
<223> OTHER INFORMATION: PCR primer

<400> SEQUENCE: 100
cggctccaga gaagagatgg tgagggtgaa gtctgtccca gacccactgc cactgaacct    60
ggcagggatc ccagattcta ggttggatac aagata    96

<210> SEQ ID NO 101
<211> LENGTH: 96
<212> TYPE: DNA
<213> ORGANISM: Artificial Sequence
<220> FEATURE:
<223> OTHER INFORMATION: PCR primer

<400> SEQUENCE: 101
atctcttctc tggagccgga ggattttgca gtctattact gtcagcacat tagggagctt    60
atcacgttcg gagggggac caaggtggaa ataaaa    96

<210> SEQ ID NO 102
<211> LENGTH: 20
<212> TYPE: DNA
<213> ORGANISM: Artificial Sequence
<220> FEATURE:
<223> OTHER INFORMATION: PCR primer

<400> SEQUENCE: 102
gaagtgcagc tggtggagtc    20

<210> SEQ ID NO 103
<211> LENGTH: 20
<212> TYPE: DNA
<213> ORGANISM: Artificial Sequence
<220> FEATURE:
<223> OTHER INFORMATION: PCR primer

<400> SEQUENCE: 103
tgaggagacg gtgactgtgg    20

<210> SEQ ID NO 104
<211> LENGTH: 20
<212> TYPE: DNA
<213> ORGANISM: Artificial Sequence
<220> FEATURE:
<223> OTHER INFORMATION: PCR primer

<400> SEQUENCE: 104
gagattgtgc tgacacagtc    20

<210> SEQ ID NO 105
<211> LENGTH: 20
<212> TYPE: DNA
<213> ORGANISM: Artificial Sequence
<220> FEATURE:
<223> OTHER INFORMATION: PCR primer

```
<400> SEQUENCE: 105
ttttatttcc accttggtcc                                              20

<210> SEQ ID NO 106
<211> LENGTH: 20
<212> TYPE: DNA
<213> ORGANISM: Artificial Sequence
<220> FEATURE:
<223> OTHER INFORMATION: PCR primer

<400> SEQUENCE: 106
aagcttatga atatgcaaat                                              20

<210> SEQ ID NO 107
<211> LENGTH: 31
<212> TYPE: DNA
<213> ORGANISM: Artificial Sequence
<220> FEATURE:
<223> OTHER INFORMATION: PCR primer

<400> SEQUENCE: 107
caccagctgc acttcggagt ggacacctgt g                                 31

<210> SEQ ID NO 108
<211> LENGTH: 31
<212> TYPE: DNA
<213> ORGANISM: Artificial Sequence
<220> FEATURE:
<223> OTHER INFORMATION: PCR primer

<400> SEQUENCE: 108
tgtcagcaca atctcggagt ggacacctgt g                                 31

<210> SEQ ID NO 109
<211> LENGTH: 30
<212> TYPE: DNA
<213> ORGANISM: Artificial Sequence
<220> FEATURE:
<223> OTHER INFORMATION: PCR primer

<400> SEQUENCE: 109
gtcaccgtct cctcaggtga gtccttacaa                                   30

<210> SEQ ID NO 110
<211> LENGTH: 20
<212> TYPE: DNA
<213> ORGANISM: Artificial Sequence
<220> FEATURE:
<223> OTHER INFORMATION: PCR primer

<400> SEQUENCE: 110
gcggatccta taaatctctg                                              20

<210> SEQ ID NO 111
<211> LENGTH: 21
<212> TYPE: DNA
<213> ORGANISM: Artificial Sequence
<220> FEATURE:
<223> OTHER INFORMATION: PCR primer

<400> SEQUENCE: 111
aaggtggaaa taaaacgtga g                                            21

<210> SEQ ID NO 112
<211> LENGTH: 20
```

```
<212> TYPE: DNA
<213> ORGANISM: Artificial Sequence
<220> FEATURE:
<223> OTHER INFORMATION: PCR primer

<400> SEQUENCE: 112
gcggatccaa ctgaggaagc                                                    20

<210> SEQ ID NO 113
<211> LENGTH: 121
<212> TYPE: PRT
<213> ORGANISM: Artificial Sequence
<220> FEATURE:
<223> OTHER INFORMATION: humanized murine VH

<400> SEQUENCE: 113
```

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Asp Thr Tyr
            20                  25                  30

Asp Met Ser Trp Val Arg Gln Ala Pro Gly Lys Gly Leu Glu Trp Val
        35                  40                  45

Ala Tyr Ile Gly Ser Gly Gly Asp Arg Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg His Tyr Gly His Tyr Val Asp Tyr Ala Val Asp Tyr Trp Gly
            100                 105                 110

Gln Gly Thr Thr Val Thr Val Ser Ser
        115                 120

```
<210> SEQ ID NO 114
<211> LENGTH: 110
<212> TYPE: PRT
<213> ORGANISM: Artificial Sequence
<220> FEATURE:
<223> OTHER INFORMATION: humanized murine VL

<400> SEQUENCE: 114
```

Glu Ile Val Leu Thr Gln Ser Pro Ala Thr Leu Ala Val Ser Pro Gly
 1               5                  10                  15

Glu Lys Ala Thr Ile Ser Tyr Arg Ala Ser Lys Ser Val Ser Thr Ser
            20                  25                  30

Gly Tyr Ser Tyr Met His Trp Asn Gln Gln Lys Pro Gly Gln Pro Pro
        35                  40                  45

Arg Leu Leu Ile Tyr Leu Val Ser Asn Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Val Glu Pro Glu Asp Ala Ala Thr Tyr Tyr Cys Gln His Ile Arg
                85                  90                  95

Glu Leu Ile Thr Phe Gly Gly Gly Thr Lys Leu Glu Ile Lys
            100                 105                 110

```
<210> SEQ ID NO 115
<211> LENGTH: 104
<212> TYPE: DNA
<213> ORGANISM: Artificial Sequence
```

```
<220> FEATURE:
<223> OTHER INFORMATION: PCR primer

<400> SEQUENCE: 115
gacatgtcat aggtatcgaa agtgaatcca gaggctgcac aggagagtct cagggaccct      60
ccaggctgca ctaagcctcc cccagactcc accagctgca cttc                     104

<210> SEQ ID NO 116
<211> LENGTH: 104
<212> TYPE: DNA
<213> ORGANISM: Artificial Sequence
<220> FEATURE:
<223> OTHER INFORMATION: PCR primer

<400> SEQUENCE: 116
cgatacctat gacatgtctt gggttcgcca ggctccgggg aagggctgg agtgggtcgc       60 atacattggt agtggtggtg atagaaccta ctatccagac actg                     104

<210> SEQ ID NO 117
<211> LENGTH: 104
<212> TYPE: DNA
<213> ORGANISM: Artificial Sequence
<220> FEATURE:
<223> OTHER INFORMATION: PCR primer

<400> SEQUENCE: 117
ggctgtgtcc tcagccctca gactgttcat ttgcaaatac aggtgttct tggcattgtc      60 tctggaaatg gtgaatcggc ccttcacagt gtctggatag tagg                     104

<210> SEQ ID NO 118
<211> LENGTH: 105
<212> TYPE: DNA
<213> ORGANISM: Artificial Sequence
<220> FEATURE:
<223> OTHER INFORMATION: PCR primer

<400> SEQUENCE: 118
agggctgagg acacagccgt gtattactgt gcaagacatt atggtcacta cgtggactat     60
gctgtggact actggggtca aggaaccaca gtcaccgtct cctca                    105

<210> SEQ ID NO 119
<211> LENGTH: 96
<212> TYPE: DNA
<213> ORGANISM: Artificial Sequence
<220> FEATURE:
<223> OTHER INFORMATION: PCR primer

<400> SEQUENCE: 119
agatgtactg acactttgc tggccctgta tgagatggtg gccttctccc ccggagatac       60
agctaaggta gcaggagact gtgtcagcac aatctc                               96

<210> SEQ ID NO 120
<211> LENGTH: 98
<212> TYPE: DNA
<213> ORGANISM: Artificial Sequence
<220> FEATURE:
<223> OTHER INFORMATION: PCR primer

<400> SEQUENCE: 120
gcaaaagtgt cagtacatct ggctatagtt atatgcactg gaaccaacag aaaccaggac     60
agccacccag actcctcatc tatcttgtat ccaaccta                             98
```

```
<210> SEQ ID NO 121
<211> LENGTH: 96
<212> TYPE: DNA
<213> ORGANISM: Artificial Sequence
<220> FEATURE:
<223> OTHER INFORMATION: PCR primer

<400> SEQUENCE: 121
cggctccaca gaactgatgg tgagggtgaa gtctgtccca gacccactgc cactgaacct     60
ggcagggacc ccagattcta ggttggatac aagata                               96

<210> SEQ ID NO 122
<211> LENGTH: 96
<212> TYPE: DNA
<213> ORGANISM: Artificial Sequence
<220> FEATURE:
<223> OTHER INFORMATION: PCR primer

<400> SEQUENCE: 122
atcagttctg tggagccgga ggatgctgca acctattact gtcagcacat tagggagctt     60
atcacgttcg gagggggggac caagctggaa ataaaa                              96

<210> SEQ ID NO 123
<211> LENGTH: 20
<212> TYPE: DNA
<213> ORGANISM: Artificial Sequence
<220> FEATURE:
<223> OTHER INFORMATION: PCR primer

<400> SEQUENCE: 123
ttttatttcc agcttggtcc                                                 20

<210> SEQ ID NO 124
<211> LENGTH: 21
<212> TYPE: DNA
<213> ORGANISM: Artificial Sequence
<220> FEATURE:
<223> OTHER INFORMATION: PCR primer

<400> SEQUENCE: 124
aagctggaaa taaaacgtga g                                               21

<210> SEQ ID NO 125
<211> LENGTH: 121
<212> TYPE: PRT
<213> ORGANISM: Artificial Sequence
<220> FEATURE:
<223> OTHER INFORMATION: humanized hybridona VH

<400> SEQUENCE: 125
```

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ala Phe Asp Thr Tyr
            20                  25                  30

Asp Met Ser Trp Val Arg Gln Ala Pro Gly Lys Gly Leu Glu Trp Val
        35                  40                  45

Ala Tyr Ile Gly Ser Gly Gly Asp Arg Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg His Tyr Gly His Tyr Val Asp Tyr Ala Val Asp Tyr Trp Gly
            100                 105                 110

Gln Gly Thr Thr Val Thr Val Ser Ser
        115                 120

<210> SEQ ID NO 126
<211> LENGTH: 121
<212> TYPE: PRT
<213> ORGANISM: Artificial Sequence
<220> FEATURE:
<223> OTHER INFORMATION: humanized hybridona VH

<400> SEQUENCE: 126

Glu Val Gln Leu Val Glu Ser Gly Gly Leu Val Gln Pro Gly Gly
  1               5                  10                  15

Ser Leu Arg Leu Ser Cys Ala Ala Ser Gly Phe Ala Phe Asp Thr Tyr
            20                  25                  30

Asp Met Ser Trp Val Arg Gln Ala Pro Gly Lys Gly Leu Glu Trp Val
            35                  40                  45

Ala Tyr Ile Gly Ser Gly Gly Asp Arg Thr Tyr Tyr Pro Asp Thr Val
 50                  55                  60

Lys Gly Arg Phe Thr Ile Ser Arg Asp Asn Ala Lys Asn Ser Leu Ser
65                  70                  75                  80

Leu Gln Met Asn Ser Leu Arg Ala Glu Asp Thr Ala Val Tyr Tyr Cys
            85                  90                  95

Ala Arg His Tyr Gly His Tyr Val Asp Tyr Ala Val Asp Tyr Trp Gly
            100                 105                 110

Gln Gly Ser Thr Val Thr Val Ser Ser
        115                 120

<210> SEQ ID NO 127
<211> LENGTH: 20
<212> TYPE: DNA
<213> ORGANISM: Artificial Sequence
<220> FEATURE:
<223> OTHER INFORMATION: PCR primer

<400> SEQUENCE: 127
tccctgtctt tgcaaatgaa                                          20

<210> SEQ ID NO 128
<211> LENGTH: 23
<212> TYPE: DNA
<213> ORGANISM: Artificial Sequence
<220> FEATURE:
<223> OTHER INFORMATION: PCR primer

<400> SEQUENCE: 128
catttgcaaa gacagggagt tct                                      23

<210> SEQ ID NO 129
<211> LENGTH: 20
<212> TYPE: DNA
<213> ORGANISM: Artificial Sequence
<220> FEATURE:
<223> OTHER INFORMATION: PCR primer

<400> SEQUENCE: 129
tcaaggatcc acagtcaccg                                          20

<210> SEQ ID NO 130

```
<211> LENGTH: 20
<212> TYPE: DNA
<213> ORGANISM: Artificial Sequence
<220> FEATURE:
<223> OTHER INFORMATION: PCR primer

<400> SEQUENCE: 130
actgtggatc cttgacccca                                             20

<210> SEQ ID NO 131
<211> LENGTH: 20
<212> TYPE: DNA
<213> ORGANISM: Artificial Sequence
<220> FEATURE:
<223> OTHER INFORMATION: PCR primer

<400> SEQUENCE: 131
aagcttatga atatgcaaat                                             20

<210> SEQ ID NO 132
<211> LENGTH: 20
<212> TYPE: DNA
<213> ORGANISM: Artificial Sequence
<220> FEATURE:
<223> OTHER INFORMATION: PCR primer

<400> SEQUENCE: 132
gcggatccta taaatctctg                                             20

<210> SEQ ID NO 133
<211> LENGTH: 121
<212> TYPE: PRT
<213> ORGANISM: Artificial Sequence
<220> FEATURE:
<223> OTHER INFORMATION: humanized murine hybridoma VH

<400> SEQUENCE: 133
```

Glu Val Gln Leu Val Glu Ser Gly Gly Gly Leu Val Lys Ala Gly Gly
 1               5                  10                  15

Ser Leu Lys Leu Ser Cys Ala Ala Ser Gly Phe Ala Phe Asp Thr Tyr
            20                  25                  30

Asp Met Ser Trp Val Arg Gln Thr Pro Glu Lys Arg Leu Glu Trp Val
        35                  40                  45

Ala Tyr Ile Gly Ser Gly Gly Asp Arg Thr Tyr Tyr Pro Asp Thr Val
    50                  55                  60

Lys Gly Arg Phe Thr Ile Ser Arg Asp Asn Gly Lys Asn Ser Leu Tyr
65                  70                  75                  80

Leu Gln Met Asn Ser Leu Lys Ser Glu Asp Thr Ala Met Tyr Tyr Cys
                85                  90                  95

Ala Arg His Tyr Gly His Tyr Val Asp Tyr Ala Val Asp Tyr Trp Gly
            100                 105                 110

Gln Gly Thr Ser Val Thr Val Ser Ser
        115                 120

```
<210> SEQ ID NO 134
<211> LENGTH: 104
<212> TYPE: DNA
<213> ORGANISM: Artificial Sequence
<220> FEATURE:
<223> OTHER INFORMATION: PCR primer

<400> SEQUENCE: 134
gacatgtcat aggtatcgaa agcgaatcca gaggctgcac aggagagttt cagggaccct    60
```

```
ccagccttca ctaagcctcc cccagactcc accagctgca cttc                       104

<210> SEQ ID NO 135
<211> LENGTH: 104
<212> TYPE: DNA
<213> ORGANISM: Artificial Sequence
<220> FEATURE:
<223> OTHER INFORMATION: PCR primer

<400> SEQUENCE: 135
ggctgtgtcc tcagacttca gactgttcat ttgcaaatac agggagttct tgccattgtc      60
tctggaaatg gtgaatcggc ccttcacagt gtctggatag tagg                      104

<210> SEQ ID NO 136
<211> LENGTH: 104
<212> TYPE: DNA
<213> ORGANISM: Artificial Sequence
<220> FEATURE:
<223> OTHER INFORMATION: PCR primer

<400> SEQUENCE: 136
ggctgtgtcc tcagacttca gactgttcat ttgcaaatac agggagttct tgccattgtc      60
tctggaaatg gtgaatcggc ccttcacagt gtctggatag tagg                      104

<210> SEQ ID NO 137
<211> LENGTH: 105
<212> TYPE: DNA
<213> ORGANISM: Artificial Sequence
<220> FEATURE:
<223> OTHER INFORMATION: PCR Primer

<400> SEQUENCE: 137
aagtctgagg acacagccat gtattactgt gcaagacatt atggtcacta cgtggactat      60
gctgtggact actggggtca aggaacctca gtcaccgtct cctca                     105

<210> SEQ ID NO 138
<211> LENGTH: 20
<212> TYPE: DNA
<213> ORGANISM: Artificial Sequence
<220> FEATURE:
<223> OTHER INFORMATION: PCR primer

<400> SEQUENCE: 138
gaagtgcagc tggtggagtc                                                  20

<210> SEQ ID NO 139
<211> LENGTH: 20
<212> TYPE: DNA
<213> ORGANISM: Artificial Sequence
<220> FEATURE:
<223> OTHER INFORMATION: PCR primer

<400> SEQUENCE: 139
tgaggagacg gtgactgagg                                                  20

<210> SEQ ID NO 140
<211> LENGTH: 351
<212> TYPE: DNA
<213> ORGANISM: Mus musculus

<400> SEQUENCE: 140
gaggtccagc tgcaacagtc tggacctgag ctggtgaagc ctggggcttc agtgaagata      60
```
tcctgtaaga cttctggaca cacattcact gaatacaaca tgcagtgggt gaagcagagc    120
cttggacaga gccttgagtg gattggaggt attaatccta acaatgttgg ttctatctac    180
aaccagaagt tcaggggcaa ggccacattg actgtagaca gtcctccag cacagcctac     240 atggagctcc gcagcctgac atctgaggat tctgcagtct attactgtgc aagaggctat    300
ggtaactacg tggcttactg gggccaaggg actctggtca ctgtctctgc a              351

<210> SEQ ID NO 141
<211> LENGTH: 321
<212> TYPE: DNA
<213> ORGANISM: Mus musculus

<400> SEQUENCE: 141
gacattgtga tgacccagtc tcaaaaattc atgtccacat cagtaggaga cagggtcagc     60
gtcacctgca aggccagtca gaatgtgaat actaatgtag cctggtatca acagaaacca    120
gggcaatctc ctaaatcact gatttactcg gcatcctacc gatacagtgg agtccctgat    180
cgcttcacag gcagtggatc tgggacagat ttcactctca ccatcagcaa tgtgcagtct    240
gaagacttgg cagagttttt ctgtcagcaa tataacaggt atccgttcac gttcggtggt    300
gggaccaagc tggagctgaa a                                                321

<210> SEQ ID NO 142
<211> LENGTH: 117
<212> TYPE: PRT
<213> ORGANISM: Mus musculus

<400> SEQUENCE: 142

Glu Val Gln Leu Gln Gln Ser Gly Pro Glu Leu Val Lys Pro Gly Ala
 1               5                  10                  15

Ser Val Lys Ile Ser Cys Lys Thr Ser Gly His Thr Phe Thr Glu Tyr
            20                  25                  30

Asn Met Gln Trp Val Lys Gln Ser Leu Gly Gln Ser Leu Glu Trp Ile
        35                  40                  45

Gly Gly Ile Asn Pro Asn Asn Val Gly Ser Ile Tyr Asn Gln Lys Phe
    50                  55                  60

Arg Gly Lys Ala Thr Leu Thr Val Asp Lys Ser Ser Thr Ala Tyr
65                  70                  75                  80

Met Glu Leu Arg Ser Leu Thr Ser Glu Asp Ser Ala Val Tyr Tyr Cys
                85                  90                  95

Ala Arg Gly Tyr Gly Asn Tyr Val Ala Tyr Trp Gly Gln Gly Thr Leu
            100                 105                 110

Val Thr Val Ser Ala
        115

<210> SEQ ID NO 143
<211> LENGTH: 107
<212> TYPE: PRT
<213> ORGANISM: Mus Musculus

<400> SEQUENCE: 143

Asp Ile Val Met Thr Gln Ser Gln Lys Phe Met Ser Thr Ser Val Gly
 1               5                  10                  15

Asp Arg Val Ser Val Thr Cys Lys Ala Ser Gln Asn Val Asn Thr Asn
            20                  25                  30

Val Ala Trp Tyr Gln Gln Lys Pro Gly Gln Ser Pro Lys Ser Leu Ile
        35                  40                  45

```
Tyr Ser Ala Ser Tyr Arg Tyr Ser Gly Val Pro Asp Arg Phe Thr Gly
    50                  55                  60

Ser Gly Ser Gly Thr Asp Phe Thr Leu Thr Ile Ser Asn Val Gln Ser
65                  70                  75                  80

Glu Asp Leu Ala Glu Phe Phe Cys Gln Gln Tyr Asn Arg Tyr Pro Phe
                85                  90                  95

Thr Phe Gly Gly Gly Thr Lys Leu Glu Leu Lys
                100                 105

<210> SEQ ID NO 144
<211> LENGTH: 117
<212> TYPE: PRT
<213> ORGANISM: Artificial Sequence
<220> FEATURE:
<223> OTHER INFORMATION: Murine human hyrid

<400> SEQUENCE: 144

Glu Val Gln Leu Val Gln Ser Gly Pro Gly Leu Val Gln Pro Gly Gly
1               5                   10                  15

Ser Val Arg Ile Ser Cys Ala Thr Ser Gly His Thr Phe Ser Glu Tyr
            20                  25                  30

Asn Met Gln Trp Val Lys Gln Ala Gln Gly Lys Gly Leu Glu Trp Met
        35                  40                  45

Gly Gly Ile Asn Pro Asn Asn Val Gly Ser Ile Tyr Asn Gln Lys Phe
    50                  55                  60

Arg Gly Arg Phe Thr Leu Ser Val Glu Lys Ser Lys Asn Thr Ala Tyr
65                  70                  75                  80

Met Gln Leu Ser Ser Leu Lys Ser Glu Asp Ser Ala Val Tyr Tyr Cys
                85                  90                  95

Ala Arg Gly Tyr Gly Asn Tyr Val Ala Tyr Trp Gly Gln Gly Thr Leu
                100                 105                 110

Val Thr Val Ser Ser
            115

<210> SEQ ID NO 145
<211> LENGTH: 107
<212> TYPE: PRT
<213> ORGANISM: Artificial Sequence
<220> FEATURE:
<223> OTHER INFORMATION: Murine human hybrid

<400> SEQUENCE: 145

Asp Ile Gln Met Thr Gln Ser Pro Ser Ser Met Ser Thr Ser Val Gly
1               5                   10                  15

Asp Arg Val Thr Val Thr Cys Lys Ala Ser Gln Asn Val Asn Thr Asn
            20                  25                  30

Val Ala Trp Tyr Gln Gln Lys Pro Gly Lys Ser Pro Gln Ser Leu Ile
        35                  40                  45

Tyr Ser Ala Ser Tyr Arg Tyr Ser Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Glu Tyr Tyr Cys Gln Gln Tyr Asn Arg Tyr Pro Phe
                85                  90                  95

Thr Phe Gly Gly Gly Thr Lys Leu Glu Leu Lys
                100                 105

<210> SEQ ID NO 146
```

```
<211> LENGTH: 80
<212> TYPE: DNA
<213> ORGANISM: Artificial Sequence
<220> FEATURE:
<223> OTHER INFORMATION: PCR primer

<400> SEQUENCE: 146
tgtccagaag tcgcacagga tatcctcact gaaccccag gctgcaccag cccaggtcca      60
gactgtacca gctggacctc                                                 80

<210> SEQ ID NO 147
<211> LENGTH: 79
<212> TYPE: DNA
<213> ORGANISM: Artificial Sequence
<220> FEATURE:
<223> OTHER INFORMATION: PCR Primer

<400> SEQUENCE: 147
ctgtgcgact tctggacaca cattctctga atacaacatg cagtgggtga agcaggccca     60
aggaaagggc cttgagtgg                                                  79

<210> SEQ ID NO 148
<211> LENGTH: 80
<212> TYPE: DNA
<213> ORGANISM: Artificial Sequence
<220> FEATURE:
<223> OTHER INFORMATION: PCR Primer

<400> SEQUENCE: 148
aacctgcccc tgaacttctg gttgtagata gaaccaacat tgttaggatt aatacctccc     60
atccactcaa ggccctttcc                                                 80

<210> SEQ ID NO 149
<211> LENGTH: 80
<212> TYPE: DNA
<213> ORGANISM: Artificial Sequence
<220> FEATURE:
<223> OTHER INFORMATION: PCR Primer

<400> SEQUENCE: 149
gaagttcagg ggcaggttca cattgtctgt agagaagtcc aagaacacag cctacatgca     60
gctcagcagc ctgaaatctg                                                 80

<210> SEQ ID NO 150
<211> LENGTH: 80
<212> TYPE: DNA
<213> ORGANISM: Artificial Sequence
<220> FEATURE:
<223> OTHER INFORMATION: PCR Primer

<400> SEQUENCE: 150
ttggccccag taagccacgt agttaccata gcctcttgca cagtaataga ctgcagaatc     60
ctcagatttc aggctgctga                                                 80

<210> SEQ ID NO 151
<211> LENGTH: 42
<212> TYPE: DNA
<213> ORGANISM: Artificial Sequence
<220> FEATURE:
<223> OTHER INFORMATION: PCR Primer

<400> SEQUENCE: 151
gtggcttact ggggccaagg gactctggtc actgtctctt ca                        42
```

<210> SEQ ID NO 152
<211> LENGTH: 80
<212> TYPE: DNA
<213> ORGANISM: Artificial Sequence
<220> FEATURE:
<223> OTHER INFORMATION: PCR Primer

<400> SEQUENCE: 152
tgactggcct tgcaggtgac ggtgaccctg tctcctactg atgtggacat ggagcttgga    60
gactgggtca tctgaatgtc                                                80

<210> SEQ ID NO 153
<211> LENGTH: 80
<212> TYPE: DNA
<213> ORGANISM: Artificial Sequence
<220> FEATURE:
<223> OTHER INFORMATION: PCR Primer

<400> SEQUENCE: 153
cacctgcaag gccagtcaga atgtgaatac taatgtagcc tggtatcaac agaaaccagg    60
gaaatctcct caatcactga                                                80

<210> SEQ ID NO 154
<211> LENGTH: 80
<212> TYPE: DNA
<213> ORGANISM: Artificial Sequence
<220> FEATURE:
<223> OTHER INFORMATION: PCR Primer

<400> SEQUENCE: 154
cccagatcca ctgcctgaga agcgactagg gactccactg tatcggtagg atgccgagta    60
aatcagtgat tgaggagatt                                                80

<210> SEQ ID NO 155
<211> LENGTH: 80
<212> TYPE: DNA
<213> ORGANISM: Artificial Sequence
<220> FEATURE:
<223> OTHER INFORMATION: PCR Primer

<400> SEQUENCE: 155
tcaggcagtg gatctgggac agatttcact ctcaccatca gctctgtgca gcctgaagac    60
ttcgcagagt attactgtca                                                80

<210> SEQ ID NO 156
<211> LENGTH: 73
<212> TYPE: DNA
<213> ORGANISM: Artificial Sequence
<220> FEATURE:
<223> OTHER INFORMATION: PCR Primer

<400> SEQUENCE: 156
tttcagctcc agcttggtcc caccaccgaa cgtgaacgga tacctgttat attgctgaca    60
gtaatactct gcg                                                       73

<210> SEQ ID NO 157
<211> LENGTH: 18
<212> TYPE: DNA
<213> ORGANISM: Artificial Sequence
<220> FEATURE:
<223> OTHER INFORMATION: PCR Primer

```
<400> SEQUENCE: 157
gaggtccagc tggtacag                                               18

<210> SEQ ID NO 158
<211> LENGTH: 18
<212> TYPE: DNA
<213> ORGANISM: Artificial Sequence
<220> FEATURE:
<223> OTHER INFORMATION: PCR Primer

<400> SEQUENCE: 158
tgaagagaca gtgaccag                                               18

<210> SEQ ID NO 159
<211> LENGTH: 18
<212> TYPE: DNA
<213> ORGANISM: Artificial Sequence
<220> FEATURE:
<223> OTHER INFORMATION: PCR Primer

<400> SEQUENCE: 159
gacattcaga tgacccag                                               18

<210> SEQ ID NO 160
<211> LENGTH: 18
<212> TYPE: DNA
<213> ORGANISM: Artificial Sequence
<220> FEATURE:
<223> OTHER INFORMATION: PCR Primer

<400> SEQUENCE: 160
tttcagctcc agcttggt                                               18

<210> SEQ ID NO 161
<211> LENGTH: 22
<212> TYPE: DNA
<213> ORGANISM: Artificial Sequence
<220> FEATURE:
<223> OTHER INFORMATION: PCR Primer

<400> SEQUENCE: 161
gcaagcttat gaatatgcaa at                                          22

<210> SEQ ID NO 162
<211> LENGTH: 30
<212> TYPE: DNA
<213> ORGANISM: Artificial Sequence
<220> FEATURE:
<223> OTHER INFORMATION: PCR Primer

<400> SEQUENCE: 162
taccagctgg acctcggagt ggacacctgt                                  30

<210> SEQ ID NO 163
<211> LENGTH: 30
<212> TYPE: DNA
<213> ORGANISM: Artificial Sequence
<220> FEATURE:
<223> OTHER INFORMATION: PCR Primer

<400> SEQUENCE: 163
ggtcatctga atgtcggagt ggacacctgt                                  30

<210> SEQ ID NO 164
<211> LENGTH: 30
```

```
<212> TYPE: DNA
<213> ORGANISM: Artificial Sequence
<220> FEATURE:
<223> OTHER INFORMATION: PCR Primer

<400> SEQUENCE: 164
gtcactgtct cttcaggtga gtccttacaa                                      30

<210> SEQ ID NO 165
<211> LENGTH: 20
<212> TYPE: DNA
<213> ORGANISM: Artificial Sequence
<220> FEATURE:
<223> OTHER INFORMATION: PCR Primer

<400> SEQUENCE: 165
gcggatccta taaatctctg                                                 20

<210> SEQ ID NO 166
<211> LENGTH: 30
<212> TYPE: DNA
<213> ORGANISM: Artificial Sequence
<220> FEATURE:
<223> OTHER INFORMATION: PCR Primer

<400> SEQUENCE: 166
aagctggagc tgaaacgtga gtagaattta                                      30

<210> SEQ ID NO 167
<211> LENGTH: 20
<212> TYPE: DNA
<213> ORGANISM: Artificial Sequence
<220> FEATURE:
<223> OTHER INFORMATION: PCR Primer

<400> SEQUENCE: 167
gcggatccaa ctgaggaagc                                                 20

<210> SEQ ID NO 168
<211> LENGTH: 117
<212> TYPE: PRT
<213> ORGANISM: Artificial Sequence
<220> FEATURE:
<223> OTHER INFORMATION: Modified murine protein

<400> SEQUENCE: 168

Glu Val Gln Leu Gln Gln Ser Gly Pro Glu Leu Val Lys Pro Gly Ala
 1               5                  10                  15

Ser Val Lys Ile Ser Cys Lys Thr Ser Gly Tyr Thr Phe Thr Glu Tyr
             20                  25                  30

Asn Met Asn Trp Val Arg Gln Ser Pro Gly Gln Ser Leu Glu Trp Ile
         35                  40                  45

Gly Gly Ile Asn Pro Asn Asn Val Gly Ser Ile Tyr Asn Gln Lys Phe
     50                  55                  60

Arg Gly Lys Ala Thr Leu Thr Val Asp Lys Ser Ser Ser Thr Ala Tyr
 65                  70                  75                  80

Met Glu Leu Arg Ser Leu Thr Ser Glu Asp Ser Ala Val Tyr Tyr Cys
                 85                  90                  95

Ala Arg Gly Tyr Gly Asn Tyr Val Ala Tyr Trp Gly Gln Gly Thr Leu
            100                 105                 110

Val Thr Val Ser Ala
            115
```

<210> SEQ ID NO 169
<211> LENGTH: 107
<212> TYPE: PRT
<213> ORGANISM: Artificial Sequence
<220> FEATURE:
<223> OTHER INFORMATION: Modified murine protein

<400> SEQUENCE: 169

Asp Ile Val Met Thr Gln Ser Gln Lys Phe Val Thr Ser Val Gly
1               5                   10                  15

Asp Arg Val Ser Ile Thr Cys Lys Ala Ser Gln Asn Val Asn Thr Asn
            20                  25                  30

Val Ala Trp Tyr Gln Gln Lys Pro Gly Gln Ser Pro Gln Ser Leu Ile
        35                  40                  45

Tyr Ser Ala Ser Tyr Arg Phe Ser Gly Val Pro Asp Arg Phe Ser Gly
    50                  55                  60

Ser Gly Ser Gly Thr Asp Phe Thr Leu Thr Ile Ser Asn Val Gln Ser
65                  70                  75                  80

Glu Asp Phe Ala Glu Tyr Tyr Cys Gln Gln Tyr Asn Ser Tyr Pro Arg
                85                  90                  95

Thr Phe Gly Gly Gly Thr Lys Leu Glu Leu Lys
            100                 105

<210> SEQ ID NO 170
<211> LENGTH: 80
<212> TYPE: DNA
<213> ORGANISM: Artificial Sequence
<220> FEATURE:
<223> OTHER INFORMATION: PCR primer

<400> SEQUENCE: 170
tatccagaag tcttacagga tatcttcact gaagccccag gcttcaccag ctcaggtcca    60
gactgttgca gctggacctc                                                80

<210> SEQ ID NO 171
<211> LENGTH: 80
<212> TYPE: DNA
<213> ORGANISM: Artificial Sequence
<220> FEATURE:
<223> OTHER INFORMATION: PCR primer

<400> SEQUENCE: 171
cctgtaagac ttctggatac acattcactg aatacaacat gaactgggtg aggcagagcc    60
ccggacagag ccttgagtgg                                                80

<210> SEQ ID NO 172
<211> LENGTH: 80
<212> TYPE: DNA
<213> ORGANISM: Artificial Sequence
<220> FEATURE:
<223> OTHER INFORMATION: PCR primer

<400> SEQUENCE: 172
gaagttcagg ggcaaggcca cattgactgt agacaagtcc tccagcacag cctacatgga    60
gctccgcagc ctgacatctg                                                80

<210> SEQ ID NO 173
<211> LENGTH: 80
<212> TYPE: DNA
<213> ORGANISM: Artificial Sequence
<220> FEATURE:

<223> OTHER INFORMATION: PCR primer

<400> SEQUENCE: 173
gccttgcccc tgaacttctg gttgtagata gaaccaacat tgttaggatt aatacctcca    60
atccactcaa ggctctgtcc                                                80

<210> SEQ ID NO 174
<211> LENGTH: 42
<212> TYPE: DNA
<213> ORGANISM: Artificial Sequence
<220> FEATURE:
<223> OTHER INFORMATION: PCR primer

<400> SEQUENCE: 174
gtggcttact ggggccaagg gactctggtc actgtctctg ca                       42

<210> SEQ ID NO 175
<211> LENGTH: 80
<212> TYPE: DNA
<213> ORGANISM: Artificial Sequence
<220> FEATURE:
<223> OTHER INFORMATION: PCR primer

<400> SEQUENCE: 175
ttggccccag taagccacgt agttaccata gcctcttgca cagtaataga ctgcagaatc    60
ctcagatgtc aggctgcgga                                                80

<210> SEQ ID NO 176
<211> LENGTH: 80
<212> TYPE: DNA
<213> ORGANISM: Artificial Sequence
<220> FEATURE:
<223> OTHER INFORMATION: PCR primer

<400> SEQUENCE: 176
taacctgcaa ggccagtcag aatgtgaata ctaatgtagc ctggtatcaa cagaaaccag    60
ggcaatctcc tcaatcactg                                                80

<210> SEQ ID NO 177
<211> LENGTH: 80
<212> TYPE: DNA
<213> ORGANISM: Artificial Sequence
<220> FEATURE:
<223> OTHER INFORMATION: PCR primer

<400> SEQUENCE: 177
tgactggcct tgcaggttat gctgaccctg tctcctactg atgtggacac gaatttttga    60
gactgggtca tcacaatgtc                                                80

<210> SEQ ID NO 178
<211> LENGTH: 80
<212> TYPE: DNA
<213> ORGANISM: Artificial Sequence
<220> FEATURE:
<223> OTHER INFORMATION: PCR primer

<400> SEQUENCE: 178
ctcaggcagt ggatctggga cagatttcac tctcaccatc agcaatgtgc agtctgaaga    60 cttttgcagag tattactgtc                                               80

<210> SEQ ID NO 179
<211> LENGTH: 80

<212> TYPE: DNA
<213> ORGANISM: Artificial Sequence
<220> FEATURE:
<223> OTHER INFORMATION: PCR primer

<400> SEQUENCE: 179
ccagatccac tgcctgagaa gcgatcaggg actccactga atcggtagga tgccgagtaa    60
atcagtgatt gaggagattg                                                80

<210> SEQ ID NO 180
<211> LENGTH: 53
<212> TYPE: DNA
<213> ORGANISM: Artificial Sequence
<220> FEATURE:
<223> OTHER INFORMATION: PCR primer

<400> SEQUENCE: 180
ctggagctga acgtgagta gaatttaaac tttgcttcct cagttggatc cgc            53

<210> SEQ ID NO 181
<211> LENGTH: 80
<212> TYPE: DNA
<213> ORGANISM: Artificial Sequence
<220> FEATURE:
<223> OTHER INFORMATION: PCR primer

<400> SEQUENCE: 181
ctcacgtttc agctccagct tggtcccacc accgaacgtg cgcggatagc tgttatattg    60
ctgacagtaa tactctgcaa                                                80

<210> SEQ ID NO 182
<211> LENGTH: 20
<212> TYPE: DNA
<213> ORGANISM: Artificial Sequence
<220> FEATURE:
<223> OTHER INFORMATION: PCR primer

<400> SEQUENCE: 182
gaggtccagc tgcaacagtc                                                20

<210> SEQ ID NO 183
<211> LENGTH: 19
<212> TYPE: DNA
<213> ORGANISM: Artificial Sequence
<220> FEATURE:
<223> OTHER INFORMATION: PCR primer

<400> SEQUENCE: 183
tgcagagaca gtgaccaga                                                 19

<210> SEQ ID NO 184
<211> LENGTH: 19
<212> TYPE: DNA
<213> ORGANISM: Artificial Sequence
<220> FEATURE:
<223> OTHER INFORMATION: PCR primer

<400> SEQUENCE: 184
gacattgtga tgacccagt                                                 19

<210> SEQ ID NO 185
<211> LENGTH: 21
<212> TYPE: DNA
<213> ORGANISM: Artificial Sequence
<220> FEATURE:

```
<223> OTHER INFORMATION: PCR primer

<400> SEQUENCE: 185
gcggatccaa ctgaggaagc a                                              21

<210> SEQ ID NO 186
<211> LENGTH: 22
<212> TYPE: DNA
<213> ORGANISM: Artificial Sequence
<220> FEATURE:
<223> OTHER INFORMATION: PCR primer

<400> SEQUENCE: 186
gcaagcttat gaatatgcaa at                                             22

<210> SEQ ID NO 187
<211> LENGTH: 32
<212> TYPE: DNA
<213> ORGANISM: Artificial Sequence
<220> FEATURE:
<223> OTHER INFORMATION: PCR primer

<400> SEQUENCE: 187
gttgcagctg gacctcggag tggacacctg tg                                  32

<210> SEQ ID NO 188
<211> LENGTH: 30
<212> TYPE: DNA
<213> ORGANISM: Artificial Sequence
<220> FEATURE:
<223> OTHER INFORMATION: PCR primer

<400> SEQUENCE: 188
ggtcatcaca atgtcggagt ggacacctgt                                     30

<210> SEQ ID NO 189
<211> LENGTH: 31
<212> TYPE: DNA
<213> ORGANISM: Artificial Sequence
<220> FEATURE:
<223> OTHER INFORMATION: PCR primer

<400> SEQUENCE: 189
gtcactgtct ctgcaggtga gtccttacaa c                                   31

<210> SEQ ID NO 190
<211> LENGTH: 20
<212> TYPE: DNA
<213> ORGANISM: Artificial Sequence
<220> FEATURE:
<223> OTHER INFORMATION: PCR primer

<400> SEQUENCE: 190
gcggatccta taaatctctg                                                20

<210> SEQ ID NO 191
<211> LENGTH: 117
<212> TYPE: PRT
<213> ORGANISM: Artificial Sequence
<220> FEATURE:
<223> OTHER INFORMATION: Modified murine protein

<400> SEQUENCE: 191

Glu Val Gln Leu Gln Gln Ser Gly Pro Glu Leu Val Lys Pro Gly Ala
 1               5                  10                  15
```

Ser Val Lys Ile Ser Cys Lys Thr Ser Gly Tyr Thr Phe Thr Glu Tyr
            20                  25                  30

Asn Met Asn Trp Val Arg Gln Ser Pro Gly Gln Ser Leu Glu Trp Asn
        35                  40                  45

Gly Gly Arg Asn Asn Ser Ile Val Lys Ser Ile Thr Val Ser Ala Ser
    50                  55                  60

Gly Thr Lys Ala Thr Leu Thr Val Asp Lys Ser Ser Thr Ala Tyr
65                  70                  75                  80

Met Glu Leu Arg Ser Ala Thr Ser Glu Asp Ser Ala Gly Ile Tyr Ile
                85                  90                  95

Ser Pro Ser Tyr Thr Tyr Tyr Arg Pro Gly Val Gly Gln Gly Thr Leu
            100                 105                 110

Gly Thr Val Ser Ala
        115

<210> SEQ ID NO 192
<211> LENGTH: 107
<212> TYPE: PRT
<213> ORGANISM: Artificial Sequence
<220> FEATURE:
<223> OTHER INFORMATION: Modified murine protein

<400> SEQUENCE: 192

Asp Ile Val Met Thr Gln Ser Gln Lys Phe Val Ser Thr Ser Val Gly
1               5                   10                  15

Asp Ser Ala Ser Val Thr Cys Thr Leu Leu Ser Val Thr Arg Asn Asp
            20                  25                  30

Val Ser Arg Tyr Gln Gln Ser Pro Gly Gln Trp Pro Gln Ser Leu Ile
        35                  40                  45

Tyr Ser Ala Ser Tyr Arg Phe Ser Gly Val Pro Asp Arg Phe Ser Gly
    50                  55                  60

Ser Gly Ser Gly Thr Asp Phe Thr Leu Thr Ile Ser Asn Val Gln Ser
65                  70                  75                  80

Glu Asp Leu Ala Glu Phe Met Cys Tyr Leu Ser Gly Ala Asn Leu Asn
                85                  90                  95

Leu Thr Gly Gly Gly Thr Lys Leu Glu Val Arg
            100                 105

<210> SEQ ID NO 193
<211> LENGTH: 80
<212> TYPE: DNA
<213> ORGANISM: Artificial Sequence
<220> FEATURE:
<223> OTHER INFORMATION: PCR primer

<400> SEQUENCE: 193
tatccagaag tcttacagga tatcttcact gaagccccag gcttcaccag ctcaggtcca         60
gactgttgca gctggacctc                                                     80

<210> SEQ ID NO 194
<211> LENGTH: 80
<212> TYPE: DNA
<213> ORGANISM: Artificial Sequence
<220> FEATURE:
<223> OTHER INFORMATION: PCR primer

<400> SEQUENCE: 194
cctgtaagac ttctggatac acattcactg aatacaacat gaactgggtg aggcagagcc         60
ccggacagag ccttgagtgg                                                     80

<210> SEQ ID NO 195
<211> LENGTH: 80
<212> TYPE: DNA
<213> ORGANISM: Artificial Sequence
<220> FEATURE:
<223> OTHER INFORMATION: PCR primer

<400> SEQUENCE: 195
gcctccggca ccaaggccac attgactgta gacaagtcct ccagcacagc ctacatggag    60
ctccgcagcg ccacatctga                                                80

<210> SEQ ID NO 196
<211> LENGTH: 80
<212> TYPE: DNA
<213> ORGANISM: Artificial Sequence
<220> FEATURE:
<223> OTHER INFORMATION: PCR primer

<400> SEQUENCE: 196
gccttggtgc cggaggcgga cacggtgata gacttaacga tggagttatt gcgacctccg    60
ttccactcaa ggctctgtcc                                                80

<210> SEQ ID NO 197
<211> LENGTH: 42
<212> TYPE: DNA
<213> ORGANISM: Artificial Sequence
<220> FEATURE:
<223> OTHER INFORMATION: PCR primer

<400> SEQUENCE: 197
cgccccggcg tgggccaagg gactctgggc actgtctctg ca                       42

<210> SEQ ID NO 198
<211> LENGTH: 77
<212> TYPE: DNA
<213> ORGANISM: Artificial Sequence
<220> FEATURE:
<223> OTHER INFORMATION: PCR primer

<400> SEQUENCE: 198
tggcccacgc cggggcggta gtaggtatag gagggggaga tgtagatgcc tgcagaatcc    60
tcagatgtgg cgctgcg                                                   77

<210> SEQ ID NO 199
<211> LENGTH: 80
<212> TYPE: DNA
<213> ORGANISM: Artificial Sequence
<220> FEATURE:
<223> OTHER INFORMATION: PCR primer

<400> SEQUENCE: 199
acctgcaccc tgctgtccgt gacccgcaac gacgtatccc gctatcaaca gtccccaggg    60
caatggcctc aatcactgat                                                80

<210> SEQ ID NO 200
<211> LENGTH: 80
<212> TYPE: DNA
<213> ORGANISM: Artificial Sequence
<220> FEATURE:
<223> OTHER INFORMATION: PCR primer

<400> SEQUENCE: 200
gacagcaggg tgcaggtcac gctggcggag tctcctactg atgtggacac gaattttga    60 gactgggtca tcacaatgtc                                                80

<210> SEQ ID NO 201
<211> LENGTH: 80
<212> TYPE: DNA
<213> ORGANISM: Artificial Sequence
<220> FEATURE:
<223> OTHER INFORMATION: PCR primer

<400> SEQUENCE: 201
ggcagtggat ctgggacaga tttcactctc accatcagca atgtgcagtc tgaagacctg    60
gcagagttca tgtgttacct                                                80

<210> SEQ ID NO 202
<211> LENGTH: 80
<212> TYPE: DNA
<213> ORGANISM: Artificial Sequence
<220> FEATURE:
<223> OTHER INFORMATION: PCR primer

<400> SEQUENCE: 202
gtcccagatc cactgcctga gaagcgatca gggactccac tgaatcggta ggatgccgag    60
taaatcagtg attgaggcca                                                80

<210> SEQ ID NO 203
<211> LENGTH: 47
<212> TYPE: DNA
<213> ORGANISM: Artificial Sequence
<220> FEATURE:
<223> OTHER INFORMATION: PCR primer

<400> SEQUENCE: 203
gtgcgacgtg agtagaattt aaactttgct tcctcagttg gatccgc                  47

<210> SEQ ID NO 204
<211> LENGTH: 80
<212> TYPE: DNA
<213> ORGANISM: Artificial Sequence
<220> FEATURE:
<223> OTHER INFORMATION: PCR primer

<400> SEQUENCE: 204
ttctactcac gtcgcacctc cagcttggtc ccaccaccgg tcaggttcag gttggcgccg    60
gacaggtaac acatgaactc                                                80

<210> SEQ ID NO 205
<211> LENGTH: 20
<212> TYPE: DNA
<213> ORGANISM: Artificial Sequence
<220> FEATURE:
<223> OTHER INFORMATION: PCR primer

<400> SEQUENCE: 205
gaggtccagc tgcaacagtc                                                20

<210> SEQ ID NO 206
<211> LENGTH: 18
<212> TYPE: DNA
<213> ORGANISM: Artificial Sequence
<220> FEATURE:
<223> OTHER INFORMATION: PCR primer

<400> SEQUENCE: 206
tgcagagaca gtgcccag                                          18

<210> SEQ ID NO 207
<211> LENGTH: 19
<212> TYPE: DNA
<213> ORGANISM: Artificial Sequence
<220> FEATURE:
<223> OTHER INFORMATION: PCR primer

<400> SEQUENCE: 207
gacattgtga tgacccagt                                         19

<210> SEQ ID NO 208
<211> LENGTH: 21
<212> TYPE: DNA
<213> ORGANISM: Artificial Sequence
<220> FEATURE:
<223> OTHER INFORMATION: PCR primer

<400> SEQUENCE: 208
gcggatccaa ctgaggaagc a                                      21

<210> SEQ ID NO 209
<211> LENGTH: 22
<212> TYPE: DNA
<213> ORGANISM: Artificial Sequence
<220> FEATURE:
<223> OTHER INFORMATION: PCR primer

<400> SEQUENCE: 209
gcaagcttat gaatatgcaa at                                     22

<210> SEQ ID NO 210
<211> LENGTH: 32
<212> TYPE: DNA
<213> ORGANISM: Artificial Sequence
<220> FEATURE:
<223> OTHER INFORMATION: PCR primer

<400> SEQUENCE: 210
gttgcagctg gacctcggag tggacacctg tg                          32

<210> SEQ ID NO 211
<211> LENGTH: 30
<212> TYPE: DNA
<213> ORGANISM: Artificial Sequence
<220> FEATURE:
<223> OTHER INFORMATION: PCR primer

<400> SEQUENCE: 211
ggtcatcaca atgtcggagt ggacacctgt                             30

<210> SEQ ID NO 212
<211> LENGTH: 31
<212> TYPE: DNA
<213> ORGANISM: Artificial Sequence
<220> FEATURE:
<223> OTHER INFORMATION: PCR primer

<400> SEQUENCE: 212
gtcactgtct ctgcaggtga gtccttacaa c                           31

<210> SEQ ID NO 213
<211> LENGTH: 20
<212> TYPE: DNA

<213> ORGANISM: Artificial Sequence
<220> FEATURE:
<223> OTHER INFORMATION: PCR primer

<400> SEQUENCE: 213
gcggatccta taaatctctg                                                       20

<210> SEQ ID NO 214
<211> LENGTH: 117
<212> TYPE: PRT
<213> ORGANISM: Artificial Sequence
<220> FEATURE:
<223> OTHER INFORMATION: Modified murine protein

<400> SEQUENCE: 214

Glu Val Gln Leu Gln Gln Ser Gly Pro Glu Leu Ala Lys Phe Gly Ala
 1               5                  10                  15

Thr Ile Ser Phe Ser Cys Asn Thr Gly Tyr Lys Leu Phe Gly Ser Thr
             20                  25                  30

Ser Met Asn Arg Leu Arg Gln Ser Pro Gly Gln Ser Leu Glu Trp Asn
         35                  40                  45

Gly Gly Arg Asn Asn Ser Ile Val Lys Ser Ile Thr Val Ser Ala Ser
     50                  55                  60

Gly Thr Lys Ala Thr Leu Thr Val Asp Lys Ser Ser Ser Thr Ala Tyr
 65                  70                  75                  80

Met Glu Leu Arg Ser Ala Thr Ser Glu Asp Ser Ala Gly Ile Tyr Ile
                 85                  90                  95

Ser Pro Ser Tyr Thr Tyr Tyr Arg Pro Gly Val Gly Gln Gly Thr Leu
            100                 105                 110

Gly Thr Val Ser Ala
        115

<210> SEQ ID NO 215
<211> LENGTH: 80
<212> TYPE: DNA
<213> ORGANISM: Artificial Sequence
<220> FEATURE:
<223> OTHER INFORMATION: PCR primer

<400> SEQUENCE: 215
ttgtagccgg tgttgcagga gaaggagatg gtggcgccga acttcgccag ctcggggccg    60
gactgctgca gctgcacctc                                                80

<210> SEQ ID NO 216
<211> LENGTH: 80
<212> TYPE: DNA
<213> ORGANISM: Artificial Sequence
<220> FEATURE:
<223> OTHER INFORMATION: PCR primer

<400> SEQUENCE: 216
ctgcaacacc ggctacaagc tgttcggctc cacctccatg aaccgacttc gccagtcccc    60
cggccagtcc ctggagtgga                                                80

<210> SEQ ID NO 217
<211> LENGTH: 80
<212> TYPE: DNA
<213> ORGANISM: Artificial Sequence
<220> FEATURE:
<223> OTHER INFORMATION: PCR primer

<400> SEQUENCE: 217
gccttggtgc cggaggcgga cacggtgata gacttaacga tggagttatt gcgacctccg    60
ttccactcca gggactggcc    80

<210> SEQ ID NO 218
<211> LENGTH: 80
<212> TYPE: DNA
<213> ORGANISM: Artificial Sequence
<220> FEATURE:
<223> OTHER INFORMATION: PCR primer

<400> SEQUENCE: 218
gcctccggca ccaaggccac attgactgta gacaagtcct ccagcacagc ctacatggag    60
ctccgcagcg ccacatctga    80

<210> SEQ ID NO 219
<211> LENGTH: 42
<212> TYPE: DNA
<213> ORGANISM: Artificial Sequence
<220> FEATURE:
<223> OTHER INFORMATION: PCR primer

<400> SEQUENCE: 219
cgccccggcg tgggccaagg gactctgggc actgtctctg ca    42

<210> SEQ ID NO 220
<211> LENGTH: 77
<212> TYPE: DNA
<213> ORGANISM: Artificial Sequence
<220> FEATURE:
<223> OTHER INFORMATION: PCR primer

<400> SEQUENCE: 220
tggcccacgc cggggcggta gtaggtatag gaggggggaga tgtagatgcc tgcagaatcc    60
tcagatgtgg cgctgcg    77

<210> SEQ ID NO 221
<211> LENGTH: 20
<212> TYPE: DNA
<213> ORGANISM: Artificial Sequence
<220> FEATURE:
<223> OTHER INFORMATION: PCR primer

<400> SEQUENCE: 221
gaggtccagc tgcaacagtc    20

<210> SEQ ID NO 222
<211> LENGTH: 18
<212> TYPE: DNA
<213> ORGANISM: Artificial Sequence
<220> FEATURE:
<223> OTHER INFORMATION: PCR primer

<400> SEQUENCE: 222
tgcagagaca gtgcccag    18

<210> SEQ ID NO 223
<211> LENGTH: 22
<212> TYPE: DNA
<213> ORGANISM: Artificial Sequence
<220> FEATURE:
<223> OTHER INFORMATION: PCR primer

<400> SEQUENCE: 223

-continued

```
gcaagcttat gaatatgcaa at                                            22
```

<210> SEQ ID NO 224
<211> LENGTH: 32
<212> TYPE: DNA
<213> ORGANISM: Artificial Sequence
<220> FEATURE:
<223> OTHER INFORMATION: PCR primer

<400> SEQUENCE: 224

```
gttgcagctg gacctcggag tggacacctg tg                                 32
```

<210> SEQ ID NO 225
<211> LENGTH: 31
<212> TYPE: DNA
<213> ORGANISM: Artificial Sequence
<220> FEATURE:
<223> OTHER INFORMATION: PCR primer

<400> SEQUENCE: 225

```
gtcactgtct ctgcaggtga gtccttacaa c                                  31
```

<210> SEQ ID NO 226
<211> LENGTH: 20
<212> TYPE: DNA
<213> ORGANISM: Artificial Sequence
<220> FEATURE:
<223> OTHER INFORMATION: PCR primer

<400> SEQUENCE: 226

```
gcggatccta taaatctctg                                               20
```

<210> SEQ ID NO 227
<211> LENGTH: 95
<212> TYPE: DNA
<213> ORGANISM: Artificial Sequence
<220> FEATURE:
<223> OTHER INFORMATION: PCR primer

<400> SEQUENCE: 227

```
tattcagtga atgtgtgtcc agaagtctta caggatatct tcactgaagc cccaggcttc   60
accagctcag gtccagactg ttgcagctgg acctc                              95
```

<210> SEQ ID NO 228
<211> LENGTH: 104
<212> TYPE: DNA
<213> ORGANISM: Artificial Sequence
<220> FEATURE:
<223> OTHER INFORMATION: PCR primer

<400> SEQUENCE: 228

```
gacacacatt cactgaatac aacatgcagt gggtgaagca gagccttgga cagagccttg   60
agtggattgg aggtattaat cctaacaatg ttggttctat ctac                    104
```

<210> SEQ ID NO 229
<211> LENGTH: 103
<212> TYPE: DNA
<213> ORGANISM: Artificial Sequence
<220> FEATURE:
<223> OTHER INFORMATION: PCR primer

<400> SEQUENCE: 229

```
cagatgtcag gctgcggagc tccatgtagg ctgtgctgga ggacttgtct acagtcaatg   60
tggccttgcc cctgaacttc tggttgtaga tagaaccaac att                     103
```

<210> SEQ ID NO 230
<211> LENGTH: 105
<212> TYPE: DNA
<213> ORGANISM: Artificial Sequence
<220> FEATURE:
<223> OTHER INFORMATION: PCR primer

<400> SEQUENCE: 230
ctccgcagcc tgacatctga ggattctgca gtctattact gtgcaagagg ctatggtaac     60
tacgtggctt actggggcca agggactctg gtcactgtct ctgca                   105

<210> SEQ ID NO 231
<211> LENGTH: 104
<212> TYPE: DNA
<213> ORGANISM: Artificial Sequence
<220> FEATURE:
<223> OTHER INFORMATION: PCR primer

<400> SEQUENCE: 231
gtgaatacta atgtagcctg gtatcaacag aaaccagggc aatctcctaa atcactgatt     60
tactcggcat cctaccgata cagtggagtc cctgatcgct tcac                    104

<210> SEQ ID NO 232
<211> LENGTH: 104
<212> TYPE: DNA
<213> ORGANISM: Artificial Sequence
<220> FEATURE:
<223> OTHER INFORMATION: PCR primer

<400> SEQUENCE: 232
caggctacat tagtattcac attctgactg gccttgcagg tgacgctgac cctgtctcct     60
actgatgtgg acatgaattt ttgagactgg gtcatcacaa tgtc                    104

<210> SEQ ID NO 233
<211> LENGTH: 105
<212> TYPE: DNA
<213> ORGANISM: Artificial Sequence
<220> FEATURE:
<223> OTHER INFORMATION: PCR primer

<400> SEQUENCE: 233
tttctgtcag caatataaca ggtatccgtt cacgttcggt ggtgggacca agctggagct     60
gaaacgtgag tagaatttaa actttgcttc ctcagttgga tccgc                   105

<210> SEQ ID NO 234
<211> LENGTH: 104
<212> TYPE: DNA
<213> ORGANISM: Artificial Sequence
<220> FEATURE:
<223> OTHER INFORMATION: PCR primer

<400> SEQUENCE: 234
atattgctga cagaaaaact ctgccaagtc ttcagactgc acattgctga tggtgagagt     60
gaaatctgtc ccagatccac tgcctgtgaa gcgatcaggg actc                    104

<210> SEQ ID NO 235
<211> LENGTH: 20
<212> TYPE: DNA
<213> ORGANISM: Artificial Sequence
<220> FEATURE:
<223> OTHER INFORMATION: PCR primer

```
<400> SEQUENCE: 235
gaggtccagc tgcaacagtc                                                20

<210> SEQ ID NO 236
<211> LENGTH: 19
<212> TYPE: DNA
<213> ORGANISM: Artificial Sequence
<220> FEATURE:
<223> OTHER INFORMATION: PCR primer

<400> SEQUENCE: 236
tgcagagaca gtgaccaga                                                 19

<210> SEQ ID NO 237
<211> LENGTH: 19
<212> TYPE: DNA
<213> ORGANISM: Artificial Sequence
<220> FEATURE:
<223> OTHER INFORMATION: PCR primer

<400> SEQUENCE: 237
gacattgtga tgacccagt                                                 19

<210> SEQ ID NO 238
<211> LENGTH: 21
<212> TYPE: DNA
<213> ORGANISM: Artificial Sequence
<220> FEATURE:
<223> OTHER INFORMATION: PCR primer

<400> SEQUENCE: 238
gcggatccaa ctgaggaagc a                                              21

<210> SEQ ID NO 239
<211> LENGTH: 22
<212> TYPE: DNA
<213> ORGANISM: Artificial Sequence
<220> FEATURE:
<223> OTHER INFORMATION: PCR primer

<400> SEQUENCE: 239
gcaagcttat gaatatgcaa at                                             22

<210> SEQ ID NO 240
<211> LENGTH: 32
<212> TYPE: DNA
<213> ORGANISM: Artificial Sequence
<220> FEATURE:
<223> OTHER INFORMATION: PCR primer

<400> SEQUENCE: 240
gttgcagctg gacctcggag tggacacctg tg                                  32

<210> SEQ ID NO 241
<211> LENGTH: 30
<212> TYPE: DNA
<213> ORGANISM: Artificial Sequence
<220> FEATURE:
<223> OTHER INFORMATION: PCR primer

<400> SEQUENCE: 241
ggtcatcaca atgtcggagt ggacacctgt                                     30

<210> SEQ ID NO 242
<211> LENGTH: 31
```

```
<212> TYPE: DNA
<213> ORGANISM: Artificial Sequence
<220> FEATURE:
<223> OTHER INFORMATION: PCR primer

<400> SEQUENCE: 242
gtcactgtct ctgcaggtga gtccttacaa c                            31

<210> SEQ ID NO 243
<211> LENGTH: 20
<212> TYPE: DNA
<213> ORGANISM: Artificial Sequence
<220> FEATURE:
<223> OTHER INFORMATION: PCR primer

<400> SEQUENCE: 243
gcggatccta taaatctctg                                         20

<210> SEQ ID NO 244
<211> LENGTH: 117
<212> TYPE: PRT
<213> ORGANISM: Artificial Sequence
<220> FEATURE:
<223> OTHER INFORMATION: Humanized monoclonal antibody segmenet

<400> SEQUENCE: 244
```

Glu Val Gln Leu Leu Glu Ser Gly Gly Gly Leu Val Gln Pro Gly Gly
 1               5                  10                  15

Ser Leu Arg Leu Ser Cys Ala Ala Ser Gly Phe Ala Phe Ser Thr Tyr
            20                  25                  30

Asp Met Ser Trp Val Arg Gln Ala Pro Gly Lys Gly Leu Glu Trp Val
        35                  40                  45

Ala Thr Ile Ser Ser Gly Gly Ser Tyr Thr Tyr Tyr Leu Asp Ser Val
    50                  55                  60

Lys Gly Arg Phe Thr Ile Ser Arg Asp Ser Ser Lys Asn Thr Leu Tyr
65                  70                  75                  80

Leu Gln Met Asn Ser Leu Gln Ala Glu Asp Ser Ala Ile Tyr Tyr Cys
                85                  90                  95

Ala Pro Thr Thr Val Val Pro Phe Ala Tyr Trp Gly Gln Gly Thr Leu
            100                 105                 110

Val Thr Val Ser Ser
        115

```
<210> SEQ ID NO 245
<211> LENGTH: 107
<212> TYPE: PRT
<213> ORGANISM: Artificial Sequence
<220> FEATURE:
<223> OTHER INFORMATION: Humanized monoclonal antibody segmenet

<400> SEQUENCE: 245
```

Asp Ile Gln Met Thr Gln Ser Pro Ser Ser Leu Ser Val Ser Val Gly
 1               5                  10                  15

Asp Arg Val Thr Ile Thr Cys Lys Ala Ser Gln Asn Val Arg Thr Val
            20                  25                  30

Val Ala Trp Tyr Gln Gln Lys Pro Gly Leu Ala Pro Lys Thr Leu Ile
        35                  40                  45

Tyr Leu Ala Ser Asn Arg His Thr Gly Val Pro Ser Arg Phe Ser Gly
    50                  55                  60

Ser Gly Ser Gly Thr Asp Phe Thr Phe Thr Ile Ser Ser Leu Gln Pro
65                  70                  75                  80

```
Glu Asp Ile Ala Thr Tyr Phe Cys Gln Gln His Trp Ser Tyr Pro Leu
                85                  90                  95
Thr Phe Gly Gln Gly Thr Lys Val Glu Val Lys
            100                 105

<210> SEQ ID NO 246
<211> LENGTH: 117
<212> TYPE: PRT
<213> ORGANISM: Artificial Sequence
<220> FEATURE:
<223> OTHER INFORMATION: humanized monoclonal antibody segment

<400> SEQUENCE: 246

Glu Val Gln Leu Leu Glu Ser Gly Gly Gly Leu Val Gln Pro Gly Gly
 1               5                  10                  15
Ser Leu Arg Leu Ser Cys Ala Ala Ser Gly Phe Thr Phe Ser Thr Tyr
            20                  25                  30
Asp Met Ser Trp Val Arg Gln Ala Pro Gly Lys Gly Leu Glu Trp Val
        35                  40                  45
Ala Thr Ile Ser Ser Gly Gly Ser Tyr Thr Tyr Tyr Leu Asp Ser Val
    50                  55                  60
Lys Gly Arg Phe Thr Ile Ser Arg Asp Ser Ser Lys Asn Thr Leu Tyr
65                  70                  75                  80
Leu Gln Met Asn Ser Leu Gln Ala Glu Asp Thr Ala Leu Tyr Phe Cys
                85                  90                  95
Ala Pro Thr Thr Val Val Pro Phe Ala Tyr Trp Gly Gln Gly Thr Leu
            100                 105                 110
Val Thr Val Ser Ser
            115

<210> SEQ ID NO 247
<211> LENGTH: 107
<212> TYPE: PRT
<213> ORGANISM: Artificial Sequence
<220> FEATURE:
<223> OTHER INFORMATION: humanized monoclonal antibody segment

<400> SEQUENCE: 247

Asp Ile Gln Met Thr Gln Ser Pro Ser Ser Leu Ser Val Ser Val Gly
 1               5                  10                  15
Asp Arg Val Thr Ile Thr Cys Lys Ala Ser Gln Asn Val Arg Thr Val
            20                  25                  30
Val Ala Trp Tyr Gln Gln Lys Pro Gly Leu Ala Pro Lys Ser Leu Ile
        35                  40                  45
Tyr Leu Ala Ser Asn Arg His Thr Gly Val Pro Ser Arg Phe Ser Gly
    50                  55                  60
Ser Gly Ser Gly Thr Asp Phe Thr Phe Thr Ile Ser Ser Leu Gln Pro
65                  70                  75                  80
Glu Asp Phe Ala Thr Tyr Tyr Cys Gln Gln His Trp Ser Tyr Pro Leu
                85                  90                  95
Thr Phe Gly Gly Gly Thr Lys Val Glu Val Lys
            100                 105

<210> SEQ ID NO 248
<211> LENGTH: 117
<212> TYPE: PRT
<213> ORGANISM: Mus musculus

<400> SEQUENCE: 248
```

```
Glu Val Lys Leu Val Glu Ser Gly Gly Leu Val Lys Pro Gly Gly
 1               5                  10                  15

Ser Leu Lys Leu Ser Cys Ala Ala Ser Gly Phe Ala Phe Ser Thr Tyr
                20                  25                  30

Asp Met Ser Trp Val Arg Gln Thr Pro Glu Lys Arg Leu Glu Trp Val
             35                  40                  45

Ala Thr Ile Ser Ser Gly Gly Ser Tyr Thr Tyr Tyr Leu Asp Ser Val
         50                  55                  60

Lys Gly Arg Phe Thr Ile Ser Arg Asp Ser Ala Arg Asn Thr Leu Tyr
 65                  70                  75                  80

Leu Gln Met Ser Ser Leu Arg Ser Glu Asp Thr Ala Leu Tyr Tyr Cys
                 85                  90                  95

Ala Pro Thr Thr Val Val Pro Phe Ala Tyr Trp Gly Gln Gly Thr Leu
                100                 105                 110

Val Thr Val Ser Ala
            115
```

<210> SEQ ID NO 249
<211> LENGTH: 107
<212> TYPE: PRT
<213> ORGANISM: Mus musculus

<400> SEQUENCE: 249

```
Asp Ile Val Met Thr Gln Ser Gln Lys Phe Met Ser Thr Ser Val Gly
 1               5                  10                  15

Asp Arg Val Ser Ile Thr Cys Lys Ala Ser Gln Asn Val Arg Thr Val
                20                  25                  30

Val Ala Trp Tyr Gln Gln Lys Pro Gly Gln Ser Pro Lys Thr Leu Ile
             35                  40                  45

Tyr Leu Ala Ser Asn Arg His Thr Gly Val Pro Asp Arg Phe Thr Gly
         50                  55                  60

Ser Gly Ser Gly Thr Asp Phe Thr Leu Thr Ile Ser Asn Val Gln Ser
 65                  70                  75                  80

Glu Asp Leu Ala Asp Tyr Phe Cys Leu Gln His Trp Ser Tyr Pro Leu
                 85                  90                  95

Thr Phe Gly Ser Gly Thr Lys Leu Glu Val Lys
                100                 105
```

<210> SEQ ID NO 250
<211> LENGTH: 117
<212> TYPE: PRT
<213> ORGANISM: Artificial Sequence
<220> FEATURE:
<223> OTHER INFORMATION: Modified murine protein

<400> SEQUENCE: 250

```
Glu Val Gln Leu Val Glu Ser Gly Gly Glu Val Lys Lys Pro Gly Ala
 1               5                  10                  15

Thr Leu Lys Leu Ser Cys Lys Ala Ser Gly Phe Thr Phe Thr Thr Tyr
                20                  25                  30

Asp Met Ser Trp Val Arg Gln Ala Pro Gly Lys Gly Leu Glu Trp Val
             35                  40                  45

Ala Thr Ile Ser Ser Gly Gly Ser Tyr Thr Tyr Tyr Leu Asp Ser Val
         50                  55                  60

Lys Gly Arg Phe Thr Ile Thr Arg Asp Ser Ser Thr Asn Thr Leu Tyr
 65                  70                  75                  80
```

```
Leu Glu Met Ser Ser Leu Arg Ser Glu Asp Thr Ala Leu Tyr Phe Cys
                85                  90                  95

Ala Pro Thr Thr Val Val Pro Phe Ala Tyr Trp Gly Gln Gly Thr Leu
            100                 105                 110

Val Thr Val Ser Ser
        115

<210> SEQ ID NO 251
<211> LENGTH: 107
<212> TYPE: PRT
<213> ORGANISM: Artificial Sequence
<220> FEATURE:
<223> OTHER INFORMATION: Modified murine protein

<400> SEQUENCE: 251

Asp Ile Gln Met Thr Gln Ser Pro Ser Ser Met Ser Thr Ser Val Gly
 1               5                  10                  15

Asp Arg Val Ser Ile Thr Cys Lys Ala Ser Gln Asn Val Arg Thr Val
            20                  25                  30

Val Ala Trp Tyr Gln Gln Lys Pro Gly Lys Ser Pro Lys Ser Leu Ile
        35                  40                  45

Tyr Leu Ala Ser Asn Arg His Thr Gly Val Pro Ser Arg Phe Ser Gly
    50                  55                  60

Ser Gly Ser Gly Thr Asp Phe Thr Leu Thr Ile Ser Ser Val Gln Pro
65                  70                  75                  80

Glu Asp Phe Ala Asp Tyr Phe Cys Leu Gln His Trp Ser Tyr Pro Leu
                85                  90                  95

Thr Phe Gly Gly Gly Thr Lys Leu Glu Val Lys
            100                 105

<210> SEQ ID NO 252
<211> LENGTH: 414
<212> TYPE: PRT
<213> ORGANISM: Streptococcus equisimilis

<400> SEQUENCE: 252

Ile Ala Gly Pro Glu Trp Leu Leu Asp Arg Pro Ser Val Asn Asn Ser
 1               5                  10                  15

Gln Leu Val Val Ser Val Ala Gly Thr Val Glu Gly Thr Asn Gln Asp
            20                  25                  30

Ile Ser Leu Lys Phe Phe Glu Ile Asp Leu Thr Ser Arg Pro Ala His
            35                  40                  45

Gly Gly Lys Thr Glu Gln Gly Leu Ser Pro Lys Ser Lys Pro Phe Ala
    50                  55                  60

Thr Asp Ser Gly Ala Met Pro His Lys Leu Glu Lys Ala Asp Leu Leu
65                  70                  75                  80

Lys Ala Ile Gln Glu Gln Leu Ile Ala Asn Val His Ser Asn Asp Asp
                85                  90                  95

Tyr Phe Glu Val Ile Asp Phe Ala Ser Asp Ala Thr Ile Thr Asp Arg
                100                 105                 110

Asn Gly Lys Val Tyr Phe Ala Asp Lys Asp Gly Ser Val Thr Leu Pro
            115                 120                 125

Thr Gln Pro Val Gln Glu Phe Leu Leu Ser Gly His Val Arg Val Arg
        130                 135                 140

Pro Tyr Lys Glu Lys Pro Ile Gln Asn Gln Ala Lys Ser Val Asp Val
145                 150                 155                 160

Glu Tyr Thr Val Gln Phe Thr Pro Leu Asn Pro Asp Asp Asp Phe Arg
```

```
                   165                 170                 175
Pro Gly Leu Lys Asp Thr Lys Leu Leu Lys Thr Leu Ala Ile Gly Asp
                180                 185                 190

Thr Ile Thr Ser Gln Glu Leu Leu Ala Gln Ala Gln Ser Ile Leu Asn
            195                 200                 205

Lys Thr His Pro Gly Tyr Thr Ile Tyr Glu Arg Asp Ser Ser Ile Val
        210                 215                 220

Thr His Asp Asn Asp Ile Phe Arg Thr Ile Leu Pro Met Asp Gln Glu
225                 230                 235                 240

Phe Thr Tyr His Val Lys Asn Arg Glu Gln Ala Tyr Glu Ile Asn Lys
                245                 250                 255

Lys Ser Gly Leu Asn Glu Glu Ile Asn Asn Thr Asp Leu Ile Ser Glu
            260                 265                 270

Lys Tyr Tyr Val Leu Lys Lys Gly Glu Lys Pro Tyr Asp Pro Phe Asp
        275                 280                 285

Arg Ser His Leu Lys Leu Phe Thr Ile Lys Tyr Val Asp Val Asn Thr
            290                 295                 300

Asn Glu Leu Leu Lys Ser Glu Gln Leu Leu Thr Ala Ser Glu Arg Asn
305                 310                 315                 320

Leu Asp Phe Arg Asp Leu Tyr Asp Pro Arg Asp Lys Ala Lys Leu Leu
                325                 330                 335

Tyr Asn Asn Leu Asp Ala Phe Gly Ile Met Asp Tyr Thr Leu Thr Gly
            340                 345                 350

Lys Val Glu Asp Asn His Asp Asp Thr Asn Arg Ile Ile Thr Val Tyr
        355                 360                 365

Met Gly Lys Arg Pro Glu Gly Glu Asn Ala Ser Tyr His Leu Ala Tyr
    370                 375                 380

Asp Lys Asp Arg Tyr Thr Glu Glu Arg Glu Val Tyr Ser Tyr Leu
385                 390                 395                 400

Arg Tyr Thr Gly Thr Pro Ile Pro Asp Asn Pro Asn Asp Lys
                405                 410

<210> SEQ ID NO 253
<211> LENGTH: 414
<212> TYPE: PRT
<213> ORGANISM: Artificial Sequence
<220> FEATURE:
<223> OTHER INFORMATION: Modified strep protein

<400> SEQUENCE: 253

Ile Ala Gly Pro Glu Trp Leu Leu Asp Arg Pro Ser Val Asn Asn Ser
1               5                   10                  15

Gln Leu Val Val Ser Val Ala Gly Thr Val Glu Gly Thr Asn Gln Asp
            20                  25                  30

Ile Ser Leu Lys Phe Phe Glu Ile Asp Leu Thr Ser Arg Pro Ala His
        35                  40                  45

Gly Gly Lys Thr Glu Gln Gly Leu Ser Pro Lys Ser Lys Pro Phe Ala
    50                  55                  60

Thr Asp Ser Gly Ala Met Pro His Lys Leu Glu Lys Ala Asp Leu Leu
65                  70                  75                  80

Lys Ala Lys Gln Glu Gln Leu Ile Ala Asn Val His Ser Asn Asp Asp
                85                  90                  95

Tyr Phe Glu Val Ile Asp Phe Ala Ser Asp Ala Thr Ile Thr Asp Arg
            100                 105                 110

Asn Gly Lys Val Tyr Phe Ala Asp Lys Asp Gly Ser Val Thr Leu Pro
```

-continued

```
            115                 120                 125
Thr Gln Pro Val Gln Glu Phe Leu Leu Ser Gly His Val Arg Val Arg
        130                 135                 140

Pro Tyr Lys Glu Lys Pro Ile Gln Asn Gln Ala Lys Ser Val Asp Val
145                 150                 155                 160

Glu Tyr Thr Val Gln Phe Thr Pro Leu Asn Pro Asp Asp Phe Arg
                165                 170                 175

Pro Gly Leu Lys Asp Thr Lys Leu Leu Lys Thr Leu Ala Ile Gly Asp
                180                 185                 190

Thr Ile Thr Ser Gln Glu Leu Leu Ala Gln Ala Gln Ser Ile Leu Asn
            195                 200                 205

Lys Thr His Pro Gly Tyr Thr Ile Tyr Glu Arg Asp Ser Ser Ile Val
        210                 215                 220

Thr His Asp Asn Asp Ile Phe Arg Thr Ile Leu Pro Met Asp Gln Glu
225                 230                 235                 240

Phe Thr Tyr His Val Lys Asn Arg Glu Gln Ala Tyr Glu Ile Asn Lys
                245                 250                 255

Lys Ser Gly Leu Asn Glu Glu Ile Asn Asn Thr Asp Leu Ile Ser Glu
                260                 265                 270

Lys Tyr Tyr Val Leu Lys Lys Gly Glu Lys Pro Tyr Asp Pro Phe Asp
            275                 280                 285

Arg Ser His Leu Lys Leu Phe Thr Ile Lys Phe Val Asp Val Asn Thr
        290                 295                 300

Asn Glu Leu Leu Lys Ser Glu Gln Leu Leu Thr Ala Ser Glu Arg Asn
305                 310                 315                 320

Leu Asp Phe Arg Asp Leu Tyr Asp Pro Arg Asp Lys Ala Lys Leu Leu
                325                 330                 335

Tyr Asn Asn Leu Asp Ala Phe Gly Ile Met Asp Tyr Thr Leu Thr Gly
                340                 345                 350

Lys Val Glu Asp Asn His Asp Asp Thr Asn Arg Ile Ile Thr Val Tyr
            355                 360                 365

Met Gly Lys Arg Pro Glu Gly Glu Asn Ala Ser Tyr His Leu Ala Tyr
        370                 375                 380

Asp Lys Asp Arg Tyr Thr Glu Glu Arg Glu Val Tyr Ser Tyr Leu
385                 390                 395                 400

Arg Tyr Thr Gly Thr Pro Ile Pro Asp Asn Pro Asn Asp Lys
                405                 410
```

```
<210> SEQ ID NO 254
<211> LENGTH: 10
<212> TYPE: PRT
<213> ORGANISM: Artificial Sequence
<220> FEATURE:
<223> OTHER INFORMATION: Consensus region
<220> FEATURE:
<221> NAME/KEY: VARIANT
<222> LOCATION: (1)...(10)
<223> OTHER INFORMATION: Xaa = any amino acid

<400> SEQUENCE: 254

Leu Xaa Xaa Xaa Ala Xaa Xaa Xaa Xaa Leu
1               5                   10
```